US012642817B2

(12) United States Patent
Quinones-Hinojosa et al.

(10) Patent No.: US 12,642,817 B2
(45) Date of Patent: *Jun. 2, 2026

(54) NANOPARTICLE MODIFICATION OF HUMAN ADIPOSE-DERIVED MESENCHYMAL STEM CELLS FOR TREATING BRAIN CANCER AND OTHER NEUROLOGICAL DISEASES

(71) Applicant: THE JOHNS HOPKINS UNIVERSITY, Baltimore, MD (US)

(72) Inventors: Alfredo Quinones-Hinojosa, Bel Air, MD (US); Jordan Green, Nottingham, MD (US)

(73) Assignee: The Johns Hopkins University, Baltimore, MD (US)

( * ) Notice: Subject to any disclaimer, the term of this patent is extended or adjusted under 35 U.S.C. 154(b) by 746 days.

This patent is subject to a terminal disclaimer.

(21) Appl. No.: 18/075,940

(22) Filed: Dec. 6, 2022

(65) Prior Publication Data

US 2023/0105186 A1     Apr. 6, 2023

Related U.S. Application Data

(60) Continuation of application No. 16/600,268, filed on Oct. 11, 2019, now Pat. No. 11,547,729, which is a division of application No. 15/500,655, filed as application No. PCT/US2015/044266 on Aug. 7, 2015, now abandoned.

(60) Provisional application No. 62/034,592, filed on Aug. 7, 2014.

(51) Int. Cl.
| | |
|---|---|
| *A61K 35/28* | (2015.01) |
| *A61K 9/51* | (2006.01) |
| *A61K 31/711* | (2006.01) |
| *A61K 35/761* | (2015.01) |
| *A61K 38/17* | (2006.01) |
| *A61K 38/18* | (2006.01) |
| *A61K 38/20* | (2006.01) |
| *A61K 38/21* | (2006.01) |
| *A61K 38/45* | (2006.01) |
| *A61K 45/06* | (2006.01) |
| *C12N 5/0775* | (2010.01) |

(52) U.S. Cl.
CPC ............ *A61K 35/28* (2013.01); *A61K 9/5146* (2013.01); *A61K 9/5153* (2013.01); *A61K 9/5176* (2013.01); *A61K 31/711* (2013.01); *A61K 35/761* (2013.01); *A61K 38/1709* (2013.01); *A61K 38/1875* (2013.01); *A61K 38/20* (2013.01); *A61K 38/2013* (2013.01); *A61K 38/208* (2013.01); *A61K 38/212* (2013.01); *A61K 38/215* (2013.01); *A61K 38/45* (2013.01); *A61K 45/06* (2013.01); *C12N 5/0667* (2013.01); *C12Y 207/01021* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 6,506,559 | B1 | 1/2003 | Fire et al. |
| 6,573,099 | B2 | 6/2003 | Graham |
| 6,919,208 | B2 | 7/2005 | Levy et al. |
| 9,683,233 | B2 | 6/2017 | Thess |
| 11,547,729 | B2 | 1/2023 | Quinones-Hinojosa et al. |
| 2003/0153519 | A1 | 8/2003 | Kay et al. |
| 2003/0167490 | A1 | 9/2003 | Hunter et al. |
| 2012/0114759 | A1 | 5/2012 | Green et al. |
| 2012/0128782 | A1 | 5/2012 | Green et al. |
| 2017/0216363 | A1 | 8/2017 | Quinones-Hinojosa et al. |
| 2020/0038452 | A1 | 2/2020 | Quinones-Hinojosa et al. |

FOREIGN PATENT DOCUMENTS

| | | | |
|---|---|---|---|
| CN | 103451152 A | * | 12/2013 |
| WO | WO 2010/132879 | | 11/2010 |
| WO | WO 2014/066811 | | 5/2014 |
| WO | WO 2014/197892 | | 12/2014 |

OTHER PUBLICATIONS

Sage, et al. (2016) "Genetically modified mesenchymal stem cells in cancer therapy", Cytotherapy, 18: 1438-45. (Year: 2016).*
Tang, et al. (2024) "The role of mesenchymal stem cells in cancer and prospects for their use in cancer therapeutics", MedComm, 5: e663 (24 pages as printed). (Year: 2024).*
Sohni, et al. (2013) "Mesenchymal Stem Cell Migration Homing and Tracking", Stem Cells International, 2013: 130763, 8 pages long. (Year: 2013).*
Sung Yong Ahn (2020) "The Role of MSCs in the Tumor Microenvironment and Tumor Progression" Anticancer Research, 40(6): 3039-47, p. 3039, col. 2. (Year: 2020).*
Papa, et al. (2014) "Cancer-associated PTEN mutants act in a dominant negative manner to suppress PTEN protein function" Cell, 157(3): 595-610. (Year: 2014).*
Koehler, et al. (2001) "Challenges and Strategies for Cystic Fibrosis Lung Gene Therapy", Molecular Therapy, 4(2): 84-91. (Year: 2011).*

(Continued)

*Primary Examiner* — Robert M Kelly
(74) *Attorney, Agent, or Firm* — Fish & Richardson P.C.

(57) ABSTRACT

The presently disclosed subject matter provides compositions, methods, and kits for transfecting adipose-derived mesenchymal stem cells (AMSCs) in freshly extracted adipose tissue using nanoparticles comprising biodegradable polymers self-assembled with nucleic acid molecules. The presently disclosed subject matter also provides methods for treating a neurological disease in a patient in need thereof, the method comprising administering the AMSCs transfected with the nucleic acid molecules to the patient, wherein the nucleic acid molecules encode one or more bioactive molecules functional in the treatment of a neurological disease, particularly wherein the neurological disease is a brain tumor.

14 Claims, 25 Drawing Sheets

(56)     References Cited

OTHER PUBLICATIONS

Gruner, et al. (2021) "Examining the evidence for extracellular RNA function in mammals", Nature Reviews Genetics, 22: 448-58. (Year: 2021).*

Dunn (1994) "Autophagy and related mechanisms of lysosome-mediated protein degradation", Trends in Cell Biology, 4(4): 139-43, Abstract Only, 3 pages long. (Year: 1994).*

Haddad, et al. (2021) "Mouse models of glioblastoma for the evaluation of novel therapeutic strategies" Neuro-Oncology Advances, 3(1): 1-16. (Year: 2021).*

Abbadi et al., "Glucose-6-phosphatase is a key metabolic regulator of glioblastoma invasion," Mol. Cancer Res., 12(11):1547-59, Nov. 2014.

Aboody et al., "Neural stem cell-mediated enzyme/prodrug therapy for glioma: Preclinical studies," Sci.Transl. Med., 5(184):184ra59, May 2013.

Achanta et al., "Subventricular zone localized irradiation affects the generation of proliferating neural precursor cells and the migration of neuroblasts," Stem Cells, 30(11):2548-60, Nov. 2012.

Ahmed et al., "Neural stem cell-based cell carriers enhance therapeutic efficacy of an oncolytic adenovirus in an orthotopic mouse model of human glioblastoma," Mol Ther. 2011; 19(9): 1714-26.

Ahmed et al., "Neural stem cell-based cell carriers enhance therapeutic efficacy of an oncolytic adenovirus in an orthotopic mouse model of human glioblastoma," Molecular Therapy, 19(9):1714-26, Sep. 2011.

Attenello et al., "Use of Gliadel (BCNU) wafer in the surgical treatment of malignant glioma: a 10-year institutional experience," Annals of surgical oncology, 15(10):2887-93, Oct. 2008.

Bao et al., "Glioma stem cells promote radioresistance by preferential activation of the DNA damage response," Nature, 444(7120):756-60, Dec. 2006.

Bertassoli, et al. (2013) "Mesenchymal Stem Cells—Emphasis in Adipose Tissue", Brazilian Archives of Biology and Technology, 56(4): 607-17. (Year: 2013).

Bhise et al., "A novel assay for quantifying the No. of plasmids encapsulated by polymer nanoparticles," Small, 8(3):367-73, Feb. 2012.

Bhise et al., "Evaluating the potential of poly (beta-amino ester) nanoparticles for reprogramming human fibroblasts to become induced pluripotent stem cells," International journal of nanomedicine, 8:4641-58, Dec. 2013.

Bhise et al., "The relationship between terminal functionalization and molecular weight of a gene delivery polymer and transfection efficacy in mammary epithelial 2-D cultures and 3-D organotypic cultures," Biomaterials, 31(31):8088-96, Nov. 2010.

Bleau et al., "PTEN/PI3K/Akt pathway regulates the side population phenotype and ABCG2 activity in glioma tumor stem-like cells," Cell Stem Cell, 4(3):226-35, Mar. 2009.

Capilla-Gonzalez et al., "The Subventricular Zone Is Able to Respond to a Demyelinating Lesion After Localized Radiation," Stem Cells, 32(1):59-69, Jan. 2014.

Chaichana et al., "A Establishing percent resection and residual volume thresholds affecting survival and recurrence for patients with newly diagnosed intracranial glioblastoma," Neuro. Oneal., 16(1):113-22, Nov. 2013.

Chaichana et al., "A Multiple resections for patients with glioblastoma: prolonging survival," J. Neurosurg., 118(4):812-20, Apr. 2013.

Chaichana et al., "Intra-operatively obtained human tissue: protocols and techniques for the study of neural stem cells," J. Neurosci. Methods., 180(1):116-25, May 2009.

Chaichana et al., "Intra-operatively obtained human tissue: protocols and techniques for the study of neural stem cells," Journal of neuroscience methods, 180(1):116-25, May 2009.

Chaichana et al., "Neuro-oncology: Paediatric brain tumours-when to operate?" Nat. Rev. Neural., 9(7):362-4, Jul. 2013.

Chaichana et al., "Neurosphere assays: growth factors and hormone differences in tumor and nontumor studies," Stem Cells., 24(12):2851-7, Dec. 2006.

Chaichana et al., "Recurrence and malignant degeneration after resection of adult hemispheric lowgrade gliomas," J. Neurosurg, 112(1):10-7, Jan. 2010.

Chaichana et al., "Supratentorial glioblastoma multiforme: the role of surgical resection versus biopsy among older patients," Ann. Surg. Oneal., 18(1):239-45, Jan. 2011.

Check, "Gene therapy put on hold as third child develops cancer," Nature, 433:561, Feb. 2005.

Chen et al., Increased Subventricular Zone Radiation Dose Correlates With Survival in Glioblastoma Patients After Gross Total Resection. Int. J. Radiat. Oneal. Biol. Phys., 86(4):616-22, Jul. 2013.

Chesler et al., "The potential origin of glioblastoma initiating cells," Front Biosci. (Schol Ed), 4:190-205, Jan. 2012,.

Choi et al., "Human adipose tissue-derived mesenchymal stem cells: characteristics and therapeutic potential as cellular vehicles for prodrug gene therapy against brainstem gliomas," Eur. J. Cancer, 48(1):129-37, Jan. 2012.

Choi et al., "Therapeutic efficacy and safety of TRAIL-producing human adipose tissue-derived mesenchymal stem cells against experimental brainstem glioma," Neuro. Oncol., 13(1):61-9, Nov. 2010.

Choi, et al. (Jun. 15, 2015) "Human Adipose Tissue-Derived Mesenchymal Stem Cells Target Brain Tumor-Initiating Cells", PLoS One, 10(6): e0129292, 15 pages as printed. (Year: 2015).

clinicaltrials.gov [online], "Genetically Modified Neural Stem Cells, Flucytosine, and Leucovorin for Treating Patients With Recurrent High-Grade Gliomas," Dec. 2013, [retrieved on Oct. 11, 2019], retrieved from: URL<https://clinicaltrials.gov/ct2/show/NCT02015819>, 11 pages.

Coburn and Cullen, "Potent and specific inhibition of human immunodeficiency virus type 1 replication by RNA interference," Journal of virology, 76(18):9225-31, Sep. 2002.

Dolecek et al., "CBTRUS (Central Brain Tumor Registry of the United States) statistical report: primary brain and central nervous system tumors diagnosed in the United States in 2005-2009," Neuro Oncol., 14(S5):v1-49, 2012.

Dominici et al., "Minimal criteria for defining multipotent mesenchymal stromal cells," The International Society for Cellular Therapy position statement Cytotherapy, 8(4):315-7, Jan. 2006.

Eramo et al., "Chemotherapy resistance of glioblastoma stem cells," Cell Death Differ., 13(7):1238-41, Jul. 2006.

Feng et al., "Hypoxia-cultured human adipose-derived mesenchymal stem cells are non-oncogenic and have enhanced viability, motility, and tropism to brain cancer," Cell death & disease, 5(12):e1567, Dec. 2014.

Ford et al., "Localized CT-Guided Irradiation Inhibits Neurogenesis in Specific Regions of the Adult Mouse Brain," Radiat. Res., 175(6):774-83, Mar. 2011.

Frank et al., "Concise review: stem cells as an emerging platform for antibody therapy of cancer," Stem Cells, 28(11):2084-7, Nov. 2010.

Galli et al., "Isolation and characterization of tumorigenic, stem-like neural precursors from human glioblastoma," Cancer research, 64(19):7011-21, Oct. 2004.

Garzon-Muvdi and Quinones-Hinojosa, "Neural Stem Cell Niches and Homing: Recruitment and Integration into Functional Tissues," ILAR J., 51(1):3-23, Jan. 2010.

Garzon-Muvdi et al., "Regulation of brain tumor dispersal by NKCC1 through a novel role in focal adhesion regulation," PLoS Biol., 10(5):e1001320, May 2012.

Green et al., "Biodegradable polymeric vectors for gene delivery to human endothelial cells," Bioconjugate chemistry, 17(5):1162-9, Sep. 2006.

Green et al., "Combinatorial modification of degradable polymers enables transfection of human cells comparable to adenovirus," Advanced Materials, 19(19):2836-42, Oct. 2007.

Green et al., "Electrostatic ligand coatings of nanoparticles enable ligand-specific gene delivery to human primary cells," Nano letters, 7(4):874-9, Apr. 2007.

Green et al., "Nanoparticles for gene transfer to human embryonic stem cell colonies," Nano letters, 8(10):3126-30, Aug. 2008.

(56)            References Cited

OTHER PUBLICATIONS

Green et al., "Poly (β-amino esters): Procedures for Synthesis and Gene Delivery," Methods Mol. Biol., 480:53-63, 2009.

Green, "2011 Rita Schaffer Lecture: Nanoparticles for Intracellular Nucleic Acid Delivery," Annals of biomedical engineering, 40(7):1408-18, Jul. 2012.

Guerrero-Cázares et al., "Biodegradable polymeric nanoparticles show high efficacy and specificity at DNA delivery to human glioblastoma in vitro and in vivo," ACS nano, 8(5):5141-53, Apr. 2014.

Guerrero-Cázares et al., "Glioblastoma heterogeneity and more accurate representation in research models," World neurosurgery, 78(6):594, Dec. 2012.

Guerrero-Cázares et al., "Neurosphere culture and human organotypic model to evaluate brain tumor stem cells," Cancer Stem Cells, 73-83, 2009.

Harris et al., "Tissue-specific gene delivery via nanoparticle coating," Biomaterials, 31(5):998-1006, Feb. 2010.

Hollon, "Researchers and regulators reflect on first gene therapy death," Nat. Med., 6(1):6, Jan. 2000.

Huang et al., "Nanoparticle-delivered suicide gene therapy effectively reduces ovarian tumor burden in mice.," Cancer Res., 69(15):6184-91, Aug. 2009.

Javan et al., "New Insights Into Implementation of Mesenchymal Stem Cells in Cancer Therapy: Prospects for Anti-angiogenesis Treatment," Frontiers in oncology, 9:840, Aug. 2019.

Jiang et al., "Nanoparticle engineered TRAIL-overexpressing adipose-derived stem cells target and eradicate glioblastoma via intracranial delivery," Proc. Natl. Acad. Sci. U. S. A., 113(48):13857-13862, Nov. 2016.

Kim et al., "Differential polymer structure tunes mechanism of cellular uptake and transfection routes of poly (β-amino ester) polyplexes in human breast cancer cells," Bioconjugate chemistry, 25(1):43-51, Dec. 2013.

Kim et al., "Irradiation enhances the tumor tropism and therapeutic potential of tumor necrosis factor-related apoptosis-inducing ligand-secreting human umbilical cord blood-derived mesenchymal stem cells in glioma therapy," Stem cells, 28(12):2217-28, Dec. 2010.

Kim et al., "Mesoporous silica-coated hollow manganese oxide nanoparticles as positive T 1 contrast agents for labeling and MRI tracking of adipose-derived mesenchymal stem cells," Journal of the American Chemical Society, 133(9):2955-61, Feb. 2011.

Kosztowski, "Applications of neural and mesenchymal stem cells in the treatment of gliomas," Expert review of anticancer therapy, 9(5):597-612, May 2009.

Kozielski et al., "Bioengineered nanoparticles for siRNA delivery," Wiley Interdiscip Rev Nanomed Nanobiotechnol., 5(5):449-68, Sep. 2013.

Kozielski et al., "Bioreducible cationic polymer-based nanoparticles for efficient and environmentally triggered cytoplasmic siRNA delivery to primary human brain cancer cells," ACS nano, 8(4):3232-41, Apr. 2014.

Kucerova et al., "Tumor cell behaviour modulation by mesenchymal stromal cells," Mol. Cancer., 9(1):129, Dec. 2010.

Kwon et al., "Mesenchymal stem cell therapy assisted by nano-technology: a possible combinational treatment for brain tumor and central nerve regeneration," Int. J. Nanomedicine., 14:5925-5942, Jul. 2019.

Lee et al., "Gold, poly (β-amino ester) nanoparticles for small interfering RNA delivery," Nano letters, 9(6):2402-6, May 2009.

Lee et al., "Tumor stem cells derived from glioblastomas cultured in bFGF and EGF more closely mirror the phenotype and genotype of primary tumors than do serum-cultured cell lines," Cancer Cell, 9(5):391-403, May 2006.

Li et al., "c-Met signaling induces a reprogramming network and supports the glioblastoma stem-like phenotype," Proceedings of the National Academy of Sciences, 108(24):9951-6, Jun. 2011.

Li et al., "Mesenchymal stem cells from human fat engineered to secrete BMP4 are nononcogenic, suppress brain cancer, and prolong survival," Clin. Cancer Res., 20(9):2375-87, May 2014.

Mangraviti et al., "Polymeric nanoparticles for nonviral gene therapy extend brain tumor survival in vivo," ACS nano, 9(2):1236-49, Feb. 2015.

Mangraviti et al., BMP4-Secreting hAdMSCs Engineered with Nanoparticles: A Non-Viral MSC-Based Therapy for Brain Cancer. Submitted.

Mangraviti et al.,"SC-17 BMP4-Secreting hAdMSCs Engineered With Nanoparticles: a Non-Viral MSC-Based Therapy for Glioblastoma," Neuro-oncology, 16(suppl_5):v200-1, Nov. 2014.

Matuskova et al., "HSV-tk expressing mesenchymal stem cells exert bystander effect on human glioblastoma cells," Cancer letters, 290(1):58-67, Apr. 2010.

McGirt et al., "A Association of surgically acquired motor and language deficits on overall surcical after resetion of glioblastoma multiforme," Neurosurgely, 65(3):463-70, Sep. 2009.

McGirt et al., "A Extent of surgical resection is independently associated with survival in patients with hemispheric infiltrating lowgrade gliomas," Neurosurgery, 63(4):700-7, Oct. 2008.

McGirt et al., "A Independent association of extent of resection with survival in patients with malignant brain astrocytoma," J. Neurosurg., 110(1):156-62, Jan. 2009.

McGirt et al., "Gliadel (BCNU) wafer plus concomitant temozolomide therapy after primary resection of glioblastoma multiforme," Journal of neurosurgery, 110(3):583-8, Mar. 2009.

Menon et al., "Human bone marrow-derived mesenchymal stromal cells expressing S-TRAIL as a cellular delivery vehicle for human glioma therapy," Stem Cells, 27(9):2320-30, Sep. 2009.

Momin et al., "Mesenchymal stem cells: new approaches for the treatment of neurological diseases," Current stem cell research & therapy, 5(4):326-44, Dec. 2010.

Murat et al., "Stem cell-related "self-renewal" signature and high epidermal growth factor receptor expression associated with resistance to concomitant chemoradiotherapy in glioblastoma," Journal of clinical oncology, 26(18):3015-24, Jun. 2008.

Nakamizo et al., "Human bone marrow-derived mesenchymal stem cells in the treatment of gliomas," Cancer Res., 65(8):3307-18, Apr. 2005.

Nakamura et al., "Antitumor effect of genetically engineered mesenchymal stem cells in a rat glioma model," Gene Ther., 11(14):1155-64, Jul. 2004.

Neiss et al., "Treatment of advanced gastrointestinal tumors with genetically modified autologous mesenchymal stromal cells (TREAT-ME1): study protocol of a phase I/II clinical trial," BMC Cancer, 15:237, Dec. 2015.

Nguyen et al., "Polymeric materials for gene delivery and DNA vaccination," Advanced Materials, 21(8):847-67, Feb. 2009.

Pendleton et al., "Mesenchymal stem cells derived from adipose tissue vs bone marrow: in vitro comparison of their tropism towards gliomas," PloS one, 8(3):e58198, Mar. 2013.

Piccirillo et al., "Bone morphogenetic proteins inhibit the tumorigenic potential of human brain tumour-initiating cells," Nature, 444(7120):761, Dec. 2006.

Quiñones-Hinojosa and Chaichana "The human subventricular zone: a source of new cells and a potential source of brain tumors," Experimental neurology, 205(2):313-24, Jun. 2007.

Redmond et al., "A radiotherapy technique to limit dose to neural progenitor cell niches without compromising tumor coverage," Journal of neuro-oncology, 104(2):579-87, Sep. 2011.

Rich, "Cancer stem cells in radiation resistance," Cancer research, 67(19):8980-4, Oct. 2007.

Sakariassen et al., "Cancer stem cells as mediators of treatment resistance in brain tumors: status and controversies," Neoplasia, 9(11):882-92, Nov. 2007.

Sanai et al., "Unique astrocyte ribbon in adult human brain contains neural stem cells but lacks chain migration," Nature, 427(6976):740-4, Feb. 2004.

Sasportas et al., "Assessment of therapeutic efficacy and fate of engineered human mesenchymal stem cells for cancer therapy," Proc. Natl. Acad. Sci. U. S. A., 106(12):4822-7, Mar. 2009.

Schweizer et al., "A phase I study to assess the safety and cancer-homing ability of allogeneic bone marrow-derived mesenchymal stem cells in men with localized prostate cancer," Stem cells translational medicine, 8(5):441-9, May 2019.

(56)        References Cited

OTHER PUBLICATIONS

Shapiro et al., "Randomized trial of three chemotherapy regimens and two radiotherapy regimens in postoperative treatment of malignant glioma," J. Neurosurg., 71(1):1-9, Jul. 1989.

Shmueli et al., "Gene delivery nanoparticles specific for human microvasculature and macrovasculature," Nanomedicine: Nanotechnology, Biology and Medicine, 8(7):1200-7, Oct. 2012.

Shmueli et al.,"Long-term suppression of ocular neovascularization by intraocular injection of biodegradable polymeric particles containing a serpin-derived peptide," Biomaterials, 34(30):7544-51, Oct. 2013.

Showalter et al., "Nanoparticulate delivery of diphtheria toxin DNA effectively kills Mesothelin expressing pancreatic cancer cells," Cancer biology & therapy, 7(10):1584-90, Oct. 2008.

Siegel et al., "Cancer statistics, 2013," CA: a cancer journal for clinicians, 63(1):11-30, Jan. 2013.

Singh et al., "Identification of human brain tumour initiating cells," Nature, 432(7015):396-401, Nov. 2004.

Smith et al., Prime Time for Mesenchymal Stem Cell Therapy: Enhancing their Homing to Brain Tumors. Submitted.

Stupp et al., "Radiotherapy plus concomitant and adjuvant temozolomide for glioblastoma," New England Journal of Medicine, 352(10):987-96, Mar. 2005.

Sun et al., "DNER, an epigenetically modulated gene, regulates glioblastoma-derived neurosphere cell differentiation and tumor propagation," Stem Cells., 27(7):1473-86, Jul. 2009.

Sunshine et al., "Effects of base polymer hydrophobicity and end-group modification on polymeric gene delivery," Biomacromolecules, 12(10):3592-600, Sep. 2011.

Sunshine et al., "Degradable polymers for gene delivery," Conf. Proc. IEEE Eng. Med. Biol. Soc., 2009:2412-5, 2009.

Thomas et al., "Progress and problems with the use of viral vectors for gene therapy," Nature Reviews Genetics, 4(5):346, May 2003.

Tilghman et al., "HMMR maintains the stemness and tumorigenicity of glioblastoma stem-like cells," Cancer Res., 74(11):3168-79, Jun. 2014.

Tuli et al., "Development of a Novel Preclinical Pancreatic Cancer Research Model: Bioluminescence Image-Guided Focal Irradiation and Tumor Monitoring of Orthotopic Xenografts," Transl. Oneal., 5(2):77-84, Apr. 2012.

Tuli et al., "Radiosensitization of Pancreatic Cancer Cells In Vitro and In Vivo through Poly (ADP-ribose) Polymerase Inhibition with ABT-888," Transl. Oneal., Epub ahead of print, Jun. 2014.

Tzeng and Green, "Therapeutic nanomedicine for brain cancer," Ther Deliv., 4(6):687-704, Jun. 2013.

Tzeng et al., "Subtle changes to polymer structure and degradation mechanism enable highly effective nanoparticles for siRNA and DNA delivery to human brain cancer," Advanced healthcare materials, 2(3):468-80, Mar. 2013.

Tzeng et al., "Cystamine-terminated poly (beta-amino ester) s for siRNA delivery to human mesenchymal stem cells and enhancement of osteogenic differentiation," Biomaterials, 33(32):8142-51, Nov. 2012.

Tzeng et al., "Non-viral gene delivery nanoparticles based on poly (ß-amino esters) for treatment of glioblastoma," Biomaterials, 32(23):5402-10, Aug. 2011.

Tzeng et al., "Synthetic poly (ester amine) and poly (amido amine) nanoparticles for efficient DNA and siRNA delivery to human endothelial cells," International journal of nanomedicine, 6:3309, Dec. 2011.

Tzeng et al.,"Student award winner in the Ph. D. category for the 2013 society for biomaterials annual meeting and exposition, Apr. 10-13, 2013, Boston, Massachusetts: Biomaterial-mediated cancer-specific DNA delivery to liver cell cultures using synthetic poly (beta-amino ester) s," Journal of biomedical materials research Part A, 101(7):1837-45, Jul. 2013.

Van Valen et al., "Regulation of the release of tumour necrosis factor (TNF) α and soluble TNF Receptor by γ irradiation and interferon γ in Ewing's sarcoma/peripheral primitive neuroectodermal tumour cells," Journal of cancer research and clinical oncology, 123(5):245-52, May 1997.

Verhaak et al., "Integrated genomic analysis identifies clinically relevant subtypes of glioblastoma characterized by abnormalities in PDGFRA, IDH1, EGFR, and NF1," Cancer Cell, 17(1):98-110, Jan. 2010.

Vieira de Castro et al., "Impact of mesenchymal stem cells' secretome on glioblastoma pathophysiology," J. Transl. Med., 15:200, Oct. 2017.

Vilalta et al., "Biodistribution, long-term survival, and safety of human adipose tissue derived mesenchymal stem cells transplanted in nude mice by high sensitivity non- invasive bioluminescence imaging," Stem Cells Dev., 17(5):993-1003, Oct. 2008.

Vilalta et al., "Biodistribution, long-term survival, and safety of human adipose tissue-derived mesenchymal stem cells transplanted in nude mice by high sensitivity non-invasive bioluminescence imaging," Stem cells and development, 17(5):993-1004, Oct. 2008.

Wada et al., "Combined treatment effects of radiation and immunotherapy: studies in an autochthonous prostate cancer model," International Journal of Radiation Oncology* Biology* Physics, 87(4):769-76, Nov. 2013.

Wei et al., "Glioma-associated cancer-initiating cells induce immunosuppression," Clin. Cancer Res., 16(2):461-73, Jan. 2010.

Xie et al., "Aberrant NF-κB activity is critical in focal necrosis formation of human glioblastoma by regulation of the expression of tissue factor," International journal of oncology, 33(1):5-15, Jul. 2008.

Yang et al., "Gene delivery to human adult and embryonic cell-derived stem cells using biodegradable nanoparticulate polymeric vectors," Gene Ther., 16(4):533-46, Apr. 2009.

Yang et al., "Genetic engineering of human stem cells for enhanced angiogenesis using biodegradable polymeric nanoparticles," Proc. Natl. Acad. Sci. USA, 107(8):3317-22, Feb. 2010.

Ying et al., "Krüppel-Like Family of Transcription Factor 9, a Differentiation-Associated Transcription Factor, Suppresses Notch1 Signaling and Inhibits Glioblastoma-Initiating Stem Cells," Stem Cells, 29(1):20-31, Jan. 2011.

Ying et al., "Regulation of glioblastoma stem cells by retinoic acid: role for Notch pathway inhibition," Oncogene, 30(31):3454, Aug. 2011.

Yong et al., "Human bone marrow-derived mesenchymal stem cells for intravascular delivery of oncolytic adenovirus Delta24-RGD to human gliomas," Cancer Res., 69(23):8932-40, Dec. 2009.

Zaidi et al., "Origins and clinical implications of the brain tumor stem cell hypothesis," Journal of neuro-oncology, 93(1):49-60, May 2009.

Zeng et al., "Anti-PD-1 blockade and stereotactic radiation produce long-term survival in mice with intracranial gliomas," International Journal of Radiation Oncology* Biology* Physics, 86(2):343-9, Jun. 2013.

Zeng et al., "Hedgehog pathway inhibition radiosensitizes non-small cell lung cancers," International Journal of Radiation Oncology* Biology* Physics, 86(1):143-9, May 2013.

Zeng et al., "Nelfinavir induces radiation sensitization in pituitary adenoma cells," Cancer Biol. Ther., 12(7):657-63, Oct. 2011.

Zhu et al., "Human cerebrospinal fluid regulates proliferation and migration of stem cells through insulin-like growth factor-1," Stem cells and development, 24(2):160-71, Sep. 2014.

Zielske et al., "Radiation increases invasion of gene-modified mesenchymal stem cells into tumors, "Int J Radiat Oncol Biol Phys., 75(3):843-53, Nov. 2009.

* cited by examiner

*FIG. 7*

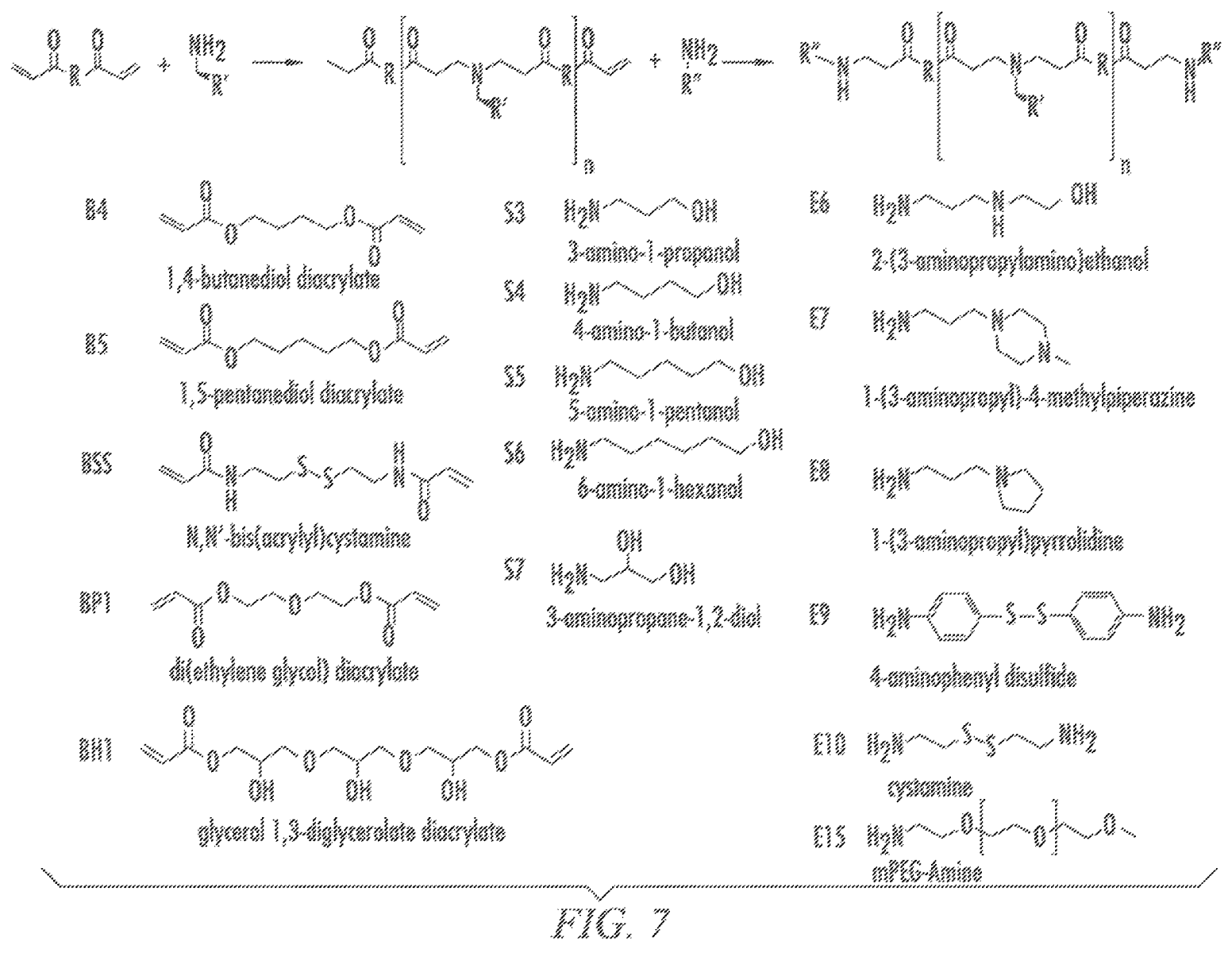

B454E7, Day 1 GFP and DsRed together
in same particle, same day (Day 3, 6ug DNA)

B454E7, Day 1 GFP and DsRed in separate
particles, same day (Day 3, 12 ug DNA)

Flow cytometry for nanoparticle-modified GFP-labeled hAMSCs in the brain
after systemic injection
(GFP expression ipsilateral and contralateral to the tumor are shown)

Bioluminescence after systemic
injection of nanoparticle-modified
Luciferase-expressing hAMSCs AIM 3 LAYOUT: In vivo brain tumor migration, proliferation, differentiation, and survival studies after treatment with BMP4-secreting nanoparticle-modified hAMSCs PBAE/BMP4 Nanoparticles Nanoparticle-modified BMP4-secreting hAMSCs Isolated hAMSCs Extraction of F.A.T. in the OR Confirm tumor with MRI Survival analysis (up to 40 weeks)

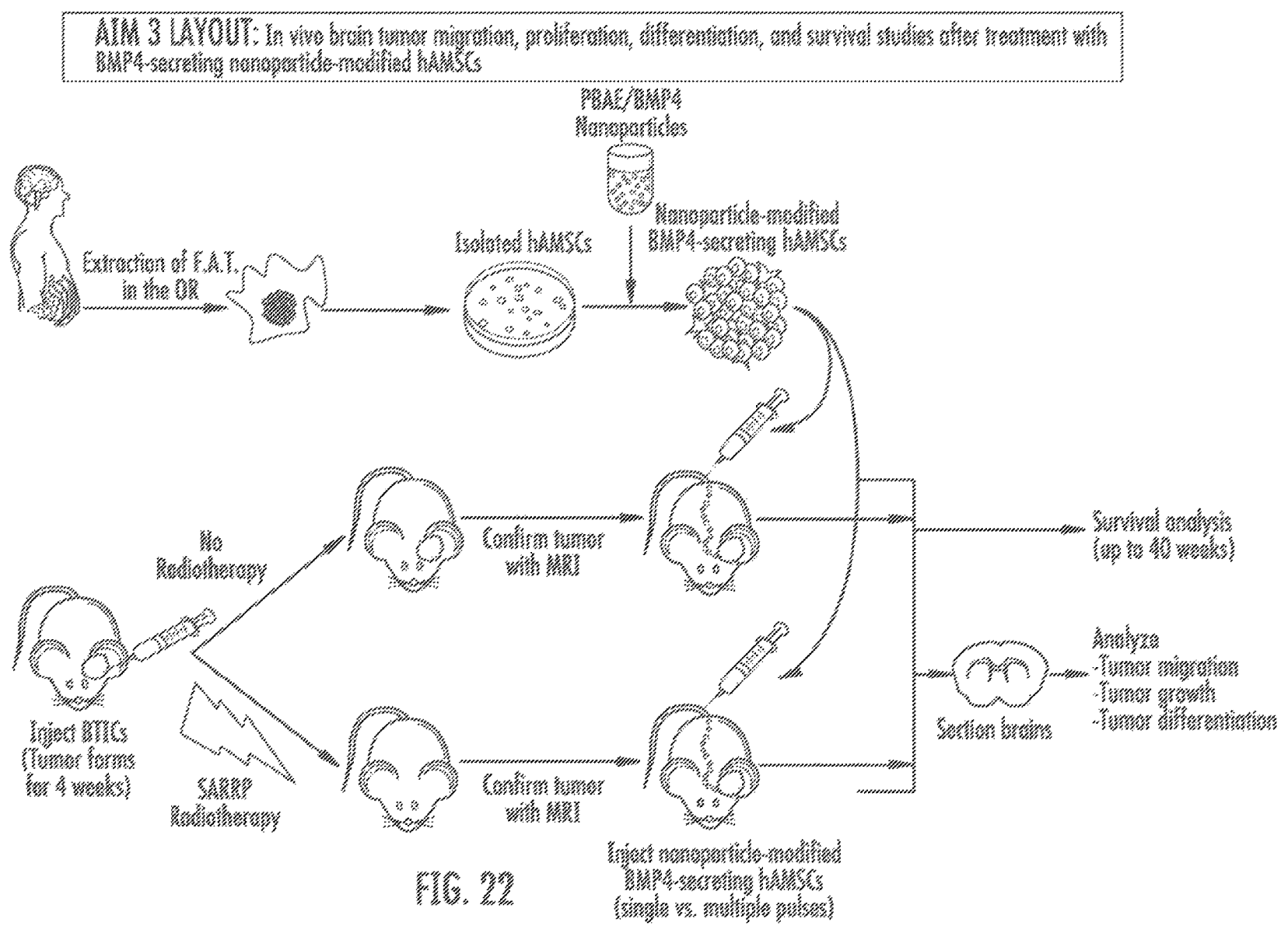

Section brains

Analyze:
- Tumor migration
- Tumor growth
- Tumor differentiation

Confirm tumor with MRI

Inject nanoparticle-modified BMP4-secreting hAMSCs (single vs. multiple pulses)

No Radiotherapy

SARRP Radiotherapy

Inject BTICs (Tumor forms for 4 weeks)

FIG. 22

NANOPARTICLE MODIFICATION OF HUMAN ADIPOSE-DERIVED MESENCHYMAL STEM CELLS FOR TREATING BRAIN CANCER AND OTHER NEUROLOGICAL DISEASES

CROSS-REFERENCE TO RELATED APPLICATIONS

This application is a continuation of U.S. application Ser. No. 16/600,268, filed Oct. 11, 2019, which is a divisional of U.S. application Ser. No. 15/500,655, filed Jan. 31, 2017, which is a 35 U.S.C. § 371 U.S. National Phase Entry of International Application PCT/US2015/044266, having an international filing date of Aug. 7, 2015, which claims the benefit of U.S. Provisional Application No. 62/034,592, filed Aug. 7, 2014, the content of each of the aforementioned applications is herein incorporated by reference in their entirety.

FEDERALLY SPONSORED RESEARCH OR DEVELOPMENT

This invention was made with government support under R01NS070024 and RO1EBO16721 awarded by the National Institutes of Health (NIH). The government has certain rights in the invention.

BACKGROUND

There are approximately 26,000 new cases of glioblastoma (GBM) each year and more than 15,000 people die from this devastating disease annually (Siegel et al, 2013; Li et al, 2014; Stupp et al, 2004). The median survival is approximately 14.6 months despite combined surgery, temozolomide chemotherapy, and radiation, and has not significantly changed for several years despite advancements in medical and surgical therapies (McGirt et al, 2008; McGirt et al, 2009; Chaichana et al, 2013; Chaichana et al, 2010; Chaichana et al, 2011). There is increasing evidence of a small subset of cells, brain tumor initiating cells (BTICs) that are responsible for the disease's treatment resistance (Singh et al, 2004; Galli et al, 2004). As a result, there is an increased impetus to find novel therapies aimed at eradicating BTICs.

The therapeutic capacity of mesenchymal stem cells (MSCs) to treat a wide spectrum of diseases in clinical and preclinical applications has often been attributed to their potential to differentiate into many different reparative cell types. However. MSCs are also an attractive potential drug carrier because they can bypass the blood-brain barrier, possess the ability to migrate long distances within the brain, and selectively locate and target migrating brain cancer cells. More importantly, MSCs serve as vehicles to deliver anti-cancer agents, including bone morphogenic protein 4 (BMP4), which has shown to be able to selectively suppress BTICs (Piccirillo et al, 2006).

MSCs can be obtained from bone marrow (BM-MSCs) and adipose tissue (AMSCs). BM-MSCs are difficult to obtain, have limited ex vivo proliferation capacity, and decrease in effectiveness with donor age. Unlike BM-MSCs, AMSCs are more abundant in supply, easier to obtain from fat tissue, express higher levels of surface markers implicated in cell migration, and have been shown to resist oncogenic transformation.

Primary human adipose-derived MSCs (hAMSCs), as compared to bone marrow-derived MSCs, have comparable GBM cell tropism, are more abundant in supply, express higher levels of surface markers implicated in cell migration, and have been shown to resist transformation (Li et al, 2014; Pendleton et al, 2013). Viral gene delivery has been used to modify MSCs to deliver therapeutic proteins for brain cancer (Li et al, 2014). However, this method of gene delivery is associated with insertional mutagenesis and immunogenicity, and, therefore, has potentially limited translational ability for use in human patients.

SUMMARY

The presently disclosed subject matter generally provides compositions and methods for nonviral engineering of freshly extracted adipose tissue (comprising human adipose-derived mesenchymal stem cells (AMSCs)) to synthesize, display, and/or release therapeutic bioactive molecules (e.g., anti-tumor proteins) involving the use of biodegradable polymeric nanoparticles combined with freshly-extracted adipose tissue from a patient. The AMSCs maintain their ability to migrate toward tumor cells, where the bioactive molecules exert their effects.

Accordingly, in one aspect, the presently disclosed subject matter provides a nanoparticle formulation comprising biodegradable polymers self-assembled with nucleic acid molecules (DNA and/or RNA). The biodegradable polymer may comprise, for example, biodegradable poly-p-amino-esters (PBAEs), poly(amido amines), polyesters including PLGA, polyanhydrides, bioreducible polymers, and other biodegradable polymers. The biodegradable polymer may be selected from the group consisting of 2-(3-aminopropylamino)ethanol end-modified poly(1,4-butanediol diacrylate-co-4-amino-1-butanol) (446), (1-(3-aminopropyl)-4-methylpiperazine end-modified poly(1,4-butanediol diacrylate-co-4-amino-1-butanol) (447), 2-(3-aminopropylamino)ethanol end-modified poly(1,4-butanediol diacrylate-co-5-amino-1-pentanol) (456). (1-(3-aminopropyl)-4-methylpiperazine end-modified poly(1,4-butanediol diacrylate-co-5-amino-1-pentanol) (457), 2-(3-aminopropylamino)ethanol end-modified poly(1,5 pentanediol diacrylate-co-3-amino-1-propanol) (536), and (1-(3-aminopropyl)-4-methylpiperazine-end-modified poly(1,5 pentanediol diacrylate-co-3-amino-1-propanol) (537). In some embodiments, the freshly extracted adipose tissue cell comprises an adipose-derived mesenchymal stem cells (AMSC).

The nucleic acid molecules may encode one or more bioactive molecules functional in the treatment of a neurological disease. The one or more bioactive molecules may be selected from the group consisting of proteins, polypeptides, peptides, drugs, enzymes, hormones. RNA, and metabolites. In a particular aspect, the neurological disease is a brain tumor, and the one or more bioactive molecules comprise one or more anti-cancer agents, particularly wherein the one or more anti-cancer agents are selected from the group consisting of bone morphogenic protein 4 (BMP4), TNF-related apoptosis-inducing ligand (TRAIL), HSV-thymidine kinase, an oncolytic adenovirus, interleukin-2 (IL-2), interleukin-12 (IL-12), interleukin-18 (IL-18), interleukin-2 3 (IL-23). Interferon-a, and Interferon-β. The nanoparticle formulation may also be lyophilized.

In another aspect, the presently disclosed subject matter provides a freshly extracted adipose tissue cell comprising at least one nanoparticle, wherein the nanoparticle comprises a biodegradable polymer self-assembled with a nucleic acid molecule. The freshly extracted adipose tissue cell may comprise an adipose-derived mesenchymal stem cell (AMSC). The biodegradable polymer may comprise, for example, biodegradable poly-p-amino-esters (PBAEs), poly (amido amines), polyesters including PLGA, polyanhydrides, bioreducible polymers, and other biodegradable polymers. The biodegradable polymer may be selected from the group consisting of 2-(3-aminopropylamino)ethanol end-modified poly(1,4-butanediol diacrylate-co-4-amino-1-butanol) (446). (1-(3-aminopropyl)-4-methylpiperazine end-modified poly(1,4-butanediol diacrylate-co-4-amino-1-butanol) (447), 2-(3-aminopropylamino)ethanol end-modified poly(1,4-butanediol diacrylate-co-5-amino-1-pentanol) (456), (1-(3-aminopropyl)-4-methylpipemzine end-modified poly(1,4-butanediol diacrylate-co-5-amino-1-pentanol) (457), 2-(3-aminopmpylamino)ethanol end-modified poly (1,5 pentanediol diacrylate-co-3-amino-1-propanol) (536), and (1-(3-aminopropyl)-4-methylpiperazine-end-modified poly(1,5 pentanediol diacrylate-co-3-amino-1-propanol) (537). In some embodiments, the freshly extracted adipose tissue cell comprises an adipose-derived mesenchymal stem cells (AMSC). The nucleic acid molecule may encode one or more bioactive molecules functional in the treatment of a neurological disease. The one or more bioactive molecules may be selected from the group consisting of proteins, polypeptides, peptides, drugs, enzymes, hormones, RNA, and metabolites. In a particular aspect, the neurological disease is a brain tumor, and the one or more bioactive molecules comprise one or more anti-cancer agents, particularly wherein the one or more anti-cancer agents are selected from the group consisting of bone morphogenic protein 4 (BMP4), TNF-related apoptosis-inducing ligand (TRAIL), HSV-thymidine kinase, an oncolytic adenovirus, interleukin-2 (IL-2), interleukin-12 (IL-12), interleukin-18 (IL-18), interleukin-23 (IL-23), Interferon-a, and Interferon-β.

The freshly extracted adipose tissue cells may be transfected during a surgery on the patient such that the nanoparticles are combined with freshly-extracted adipose tissue to form a suspension, a cellular fraction comprising freshly extracted adipose tissue cells transfected with the nucleic acid molecules is extracted from the suspension, and the freshly extracted adipose tissue cells transfected with the nucleic acid molecules are administered to the patient undergoing surgery without the cells being processed. Accordingly, in a further aspect, the presently disclosed subject matter provides a method for treating a neurological disease in a patient in need thereof, the method comprising: a) obtaining freshly extracted adipose tissue from the patient; b) transfecting cells in the freshly extracted adipose tissue, wherein transfecting comprises combining the freshly extracted adipose tissue with a nanoparticle formulation to form a suspension, wherein the nanoparticle formulation comprises biodegradable polymers self-assembled with nucleic acid molecules, and wherein the nucleic acid molecules encode one or more bioactive molecules functional in the treatment of a neurological disease; c) extracting a cellular fraction from the suspension, wherein the cellular fraction comprises freshly extracted adipose tissue cells transfected with the nucleic acid molecules, and d) administering the freshly extracted adipose tissue cells transfected with the nucleic acid molecules to the patient. The freshly extracted adipose tissue cells may comprise adipose-derived mesenchymal stem cells (AMSCs). The freshly extracted adipose tissue cells transfected with the nucleic acid molecules transfected with the nucleic acid molecules may be administered to the patient systemically or intracranially. The nanoparticle formulation may also be lyophilized prior to combining with the freshly extracted adipose tissue to form a suspension.

The nanoparticles may also be added to processed AMSCs from freshly extracted adipose tissue (i.e., AMSCs that have been isolated, purified, and cultured). Accordingly, in yet another aspect, the presently disclosed subject matter provides a method for treating a neurological disease in a patient in need thereof, the method comprising: a) obtaining freshly extracted adipose tissue from the patient, wherein the freshly extracted adipose tissue comprises adipose-derived mesenchymal stem cells (AMSCs); b) isolating and purifying the AMSCs; c) culturing the AMSCs under conditions allowing for proliferation of the AMSCs; d) transfecting the AMSCs, wherein transfecting comprises combining the freshly extracted adipose tissue with a nanoparticle formulation, wherein the nanoparticle formulation comprises biodegradable polymers self-assembled with nucleic acid molecules, and wherein the nucleic acid molecules encode one or more bioactive molecules functional in the treatment of a neurological disease; and e) administering the AMSCs transfected with the nucleic acid molecules to the patient. The AMSCs transfected with the nucleic acid molecules may be administered to the patient systemically. The AMSCs transfected with the nucleic acid molecules may also be administered to the patient in combination with an additional therapeutic agent or treatment, particularly radiotherapy when the neurological disease is a brain tumor.

In another aspect, the presently disclosed subject matter provides a kit for transfecting freshly extracted adipose tissue cells comprising: a) a lyophilized nanoparticle formulation comprising biodegradable polymers self-assembled with nucleic acid molecules; and b) instructions for combining the freshly extracted adipose tissue cells with the nanoparticle formulation to form a suspension. The freshly extracted adipose tissue cells may comprise adipose-derived mesenchymal stem cells (AMSCs). The biodegradable polymer may comprise, for example, biodegradable poly-p-amino-esters (PBAEs), poly(amido amines), polyesters including PLGA, polyanhydrides, bioreducible polymers, and other biodegradable polymers. The biodegradable polymer may be selected from the group consisting of 2-(3-aminopropylamino)ethanol end-modified poly(1,4-butanediol diacrylate-co-4-amino-1-butanol) (446), (1-(3-aminopropyl)-4-methylpiperazine end-modified poly(1,4-butanediol diacrylate-co-4-amino-1-butanol) (447), 2-(3-aminopropylamino)ethanol end-modified poly(1,4-butanediol diacrylate-co-5-amino-1-pentanol) (456), (1-(3-aminopropyl)-4-methylpiperazine end-modified poly(1,4-butanediol diacrylate-co-5-amino-1-pentanol) (457), 2-(3-aminopropylamino)ethanol end-modified poly(1,5 pentanediol diacrylate-co-3-amino-1-propanol) (536), and (1-(3-aminopropyl)-4-methylpiperazine-end-modified poly (1,5 pentanediol diacrylate-co-3-amino-1-propanol) (537). In some embodiments, the freshly extracted adipose tissue cell comprises an adipose-derived mesenchymal stem cells (AMSC). The nucleic acid molecule may encode one or more bioactive molecules functional in the treatment of a neurological disease. The one or more bioactive molecules may be selected from the group consisting of proteins, polypeptides, peptides, drugs, enzymes, hormones, RNA, and metabolites. In a particular aspect, the neurological disease is a brain tumor, and the one or more bioactive molecules comprise one or more anti-cancer agents, particularly wherein the one or more anti-cancer agents are selected from the group consisting of bone morphogenic protein 4 (BMP4), TNF-related apoptosis-inducing ligand (TRAIL). HSV-thymidine kinase, an oncolytic adenovirus, interleukin-2 (IL-2), interleukin-12 (IL-12), interleukin-18 (IL-18), interleukin-23 (IL-23). Interferon-a, and Interferon-β.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
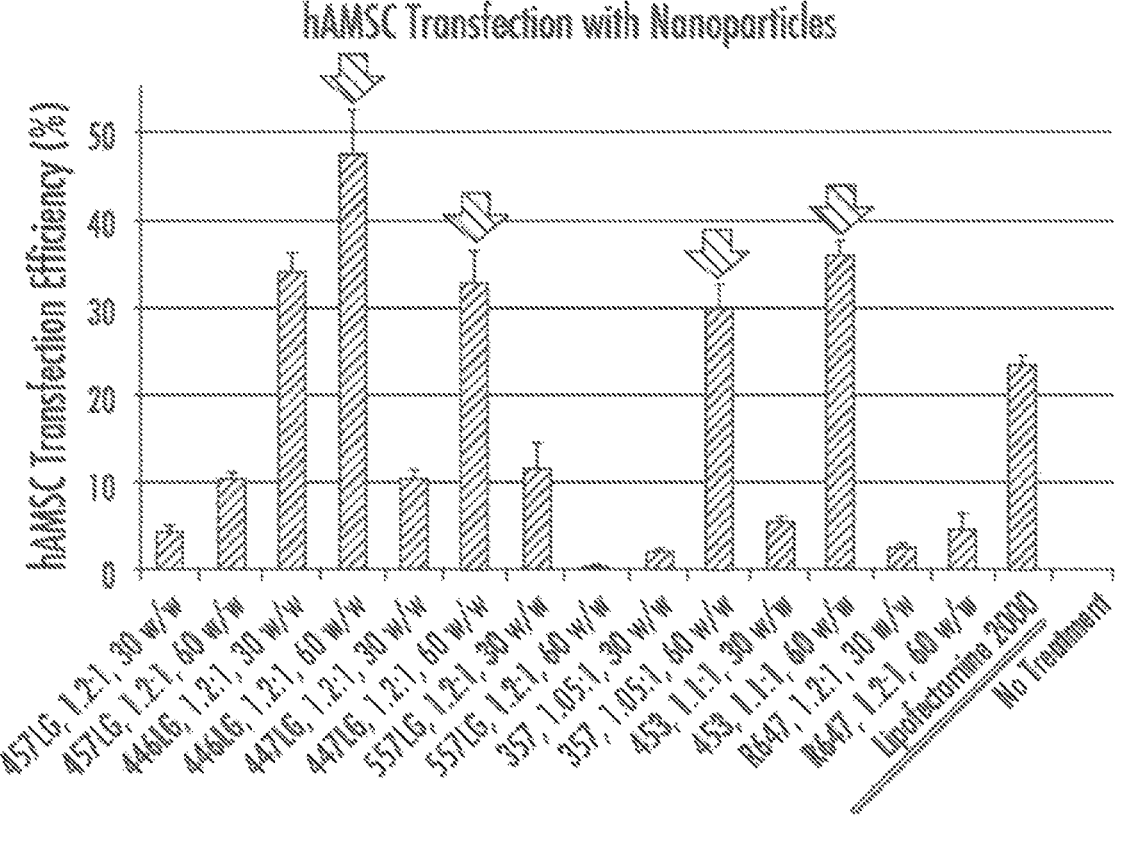
Figure 2A:
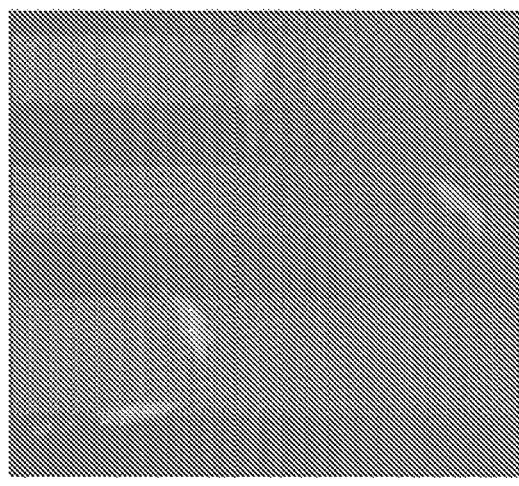
Figure 2B:
Figure 3:
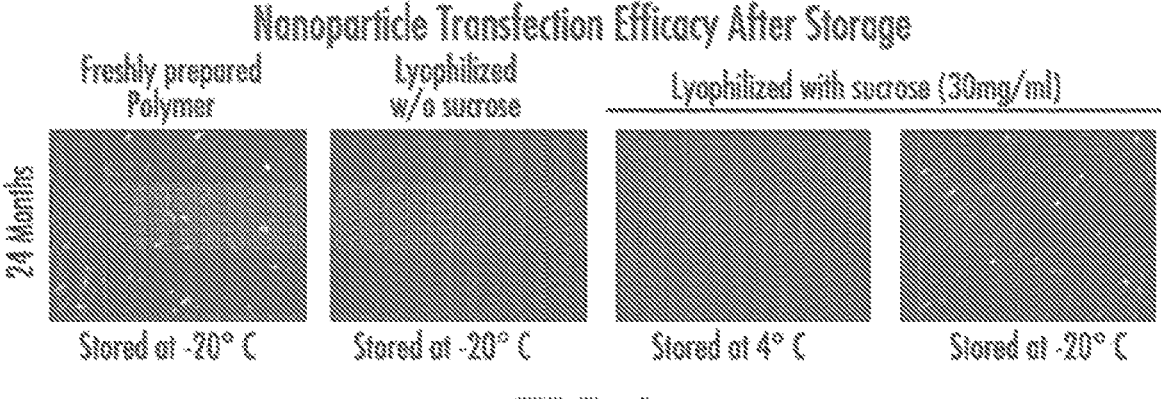
Figure 4A:
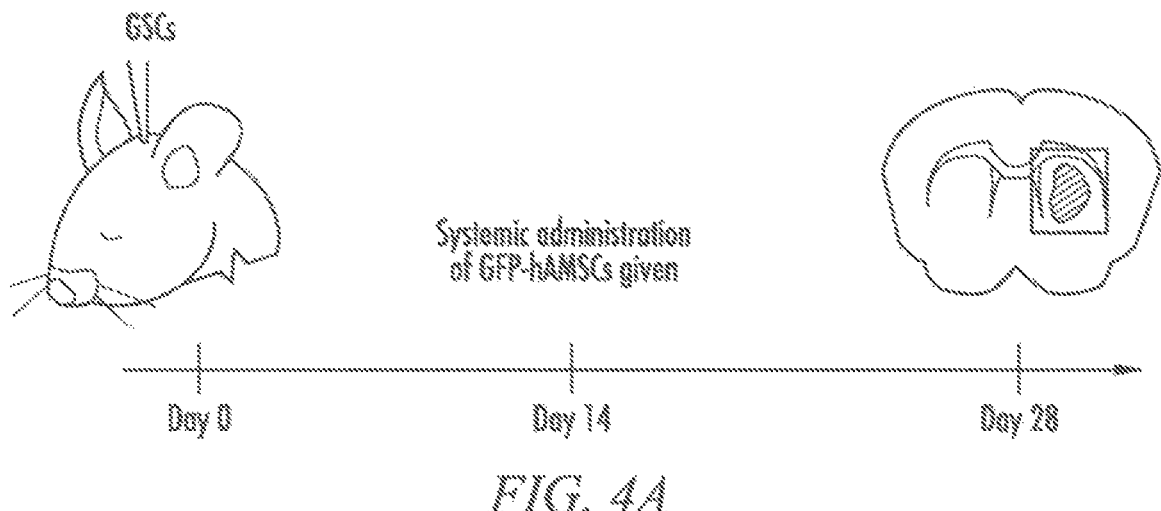
Figure 4B:
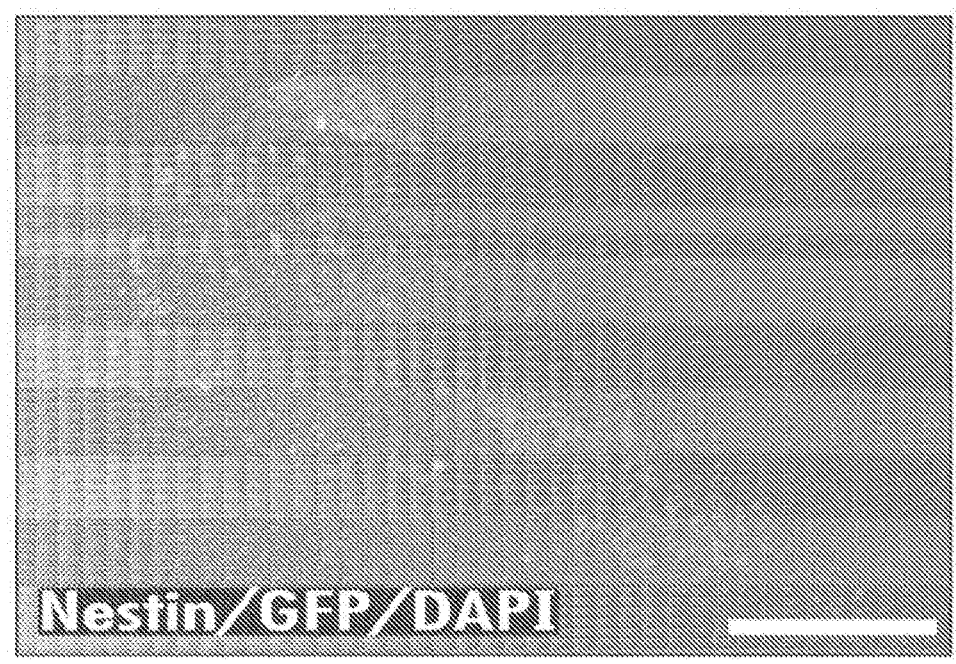
Figure 5:
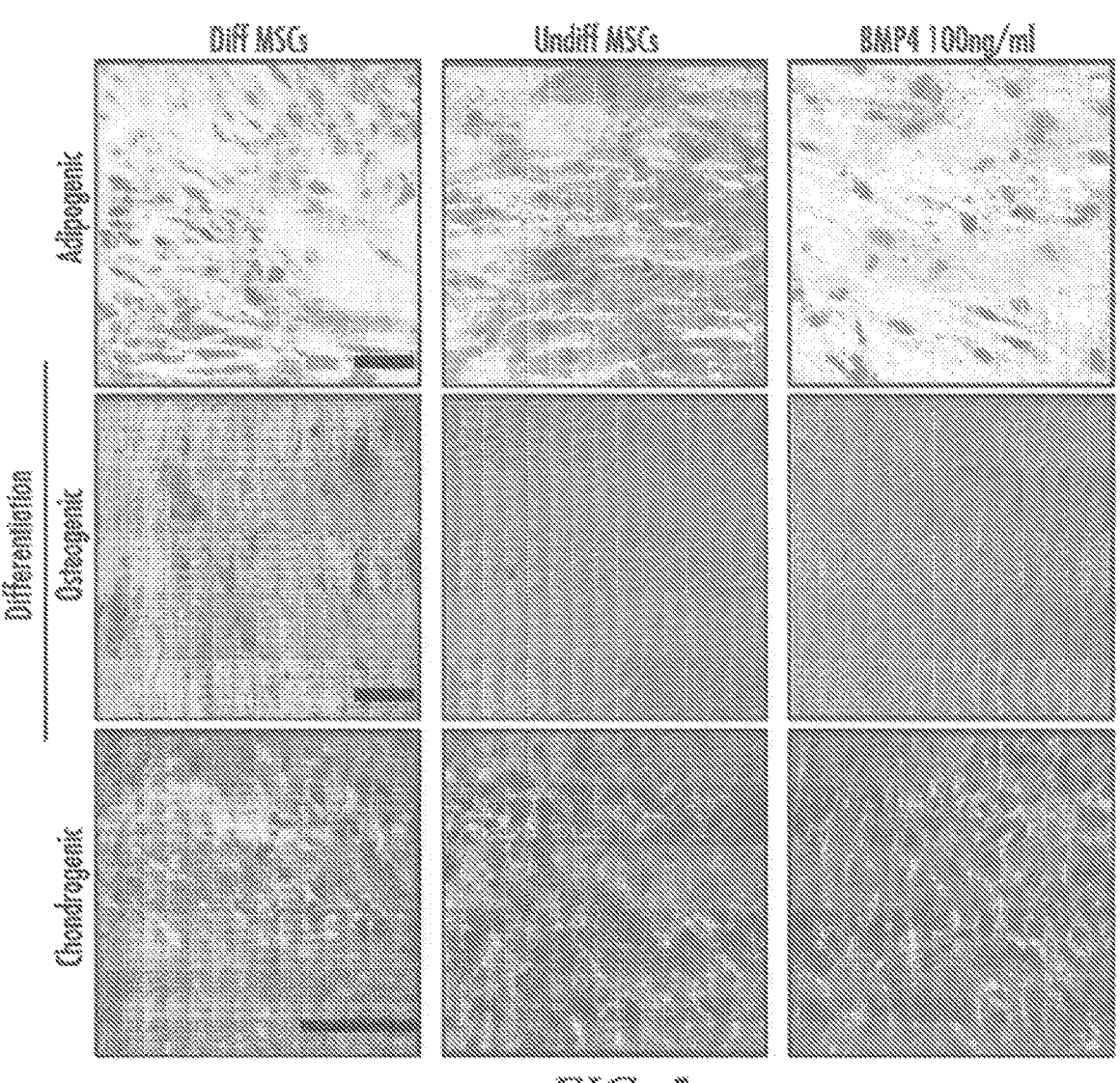
Figure 6:
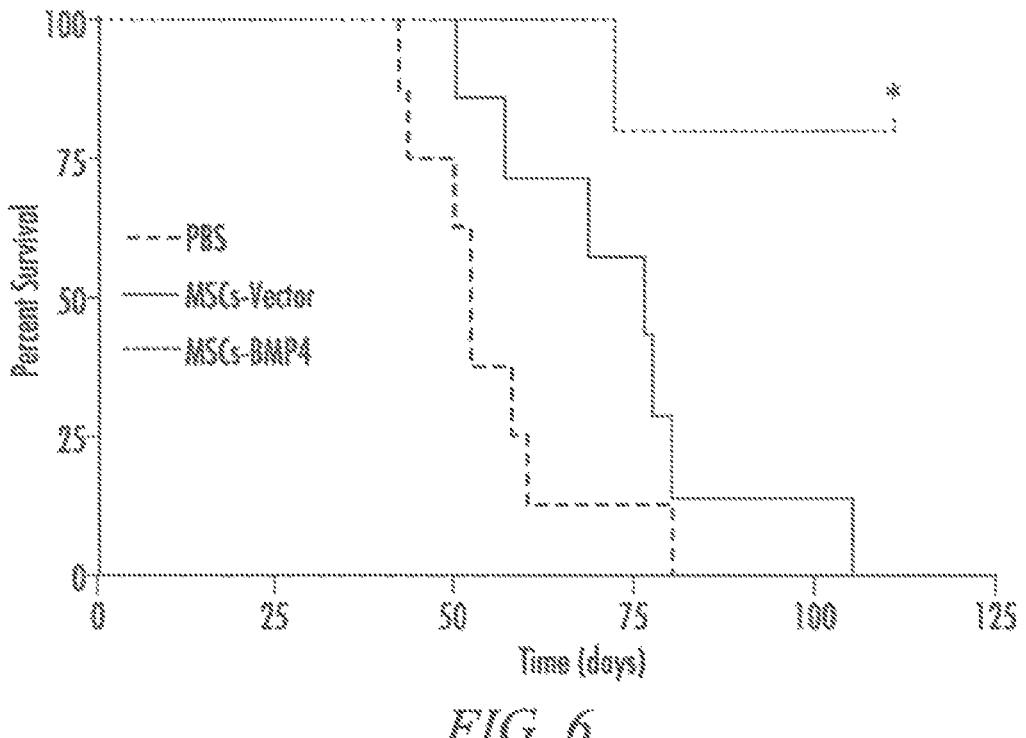
Figure 8A:
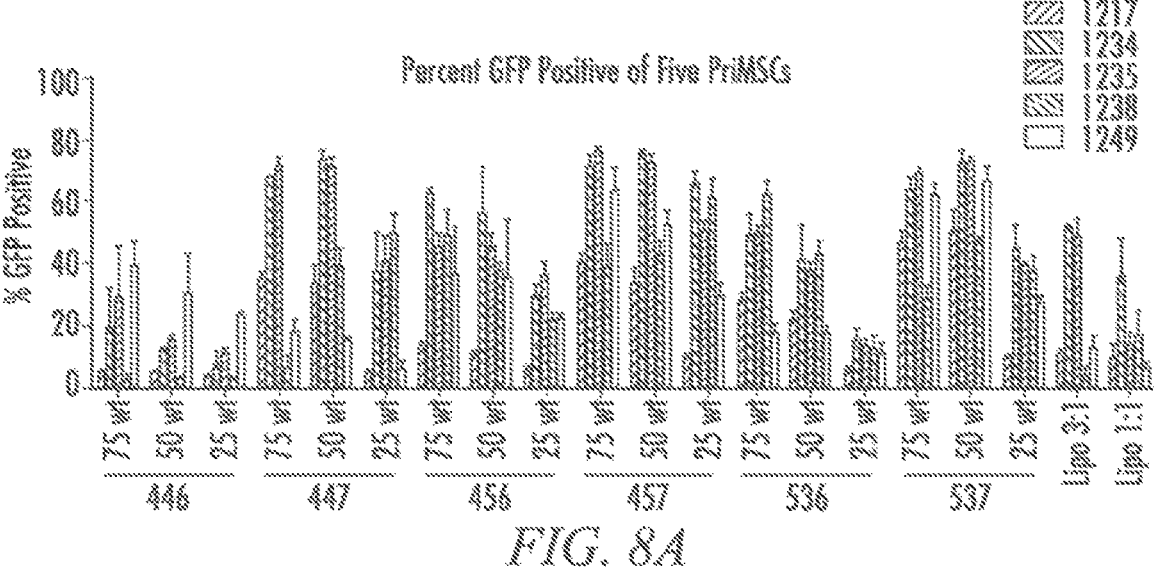
Figure 8B:
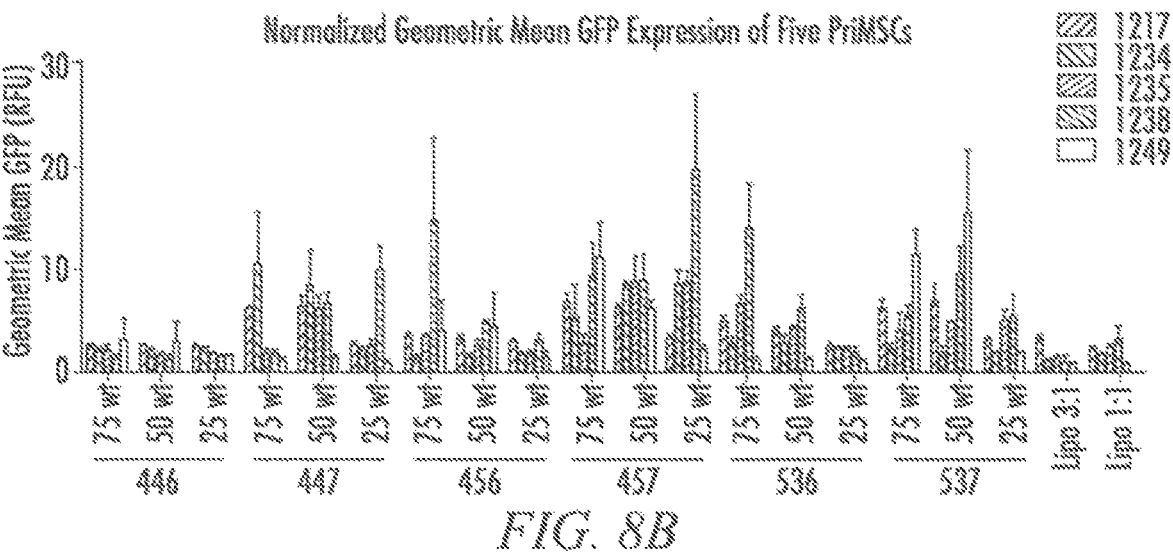
Figure 9A:
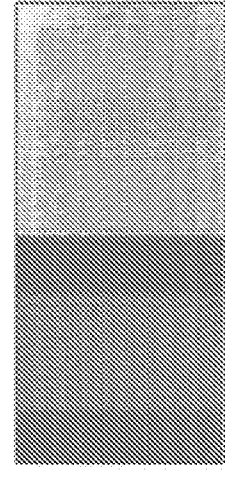
Figure 9B:
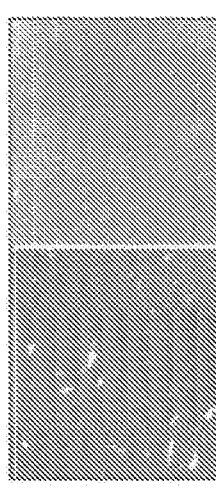
Figure 9C:
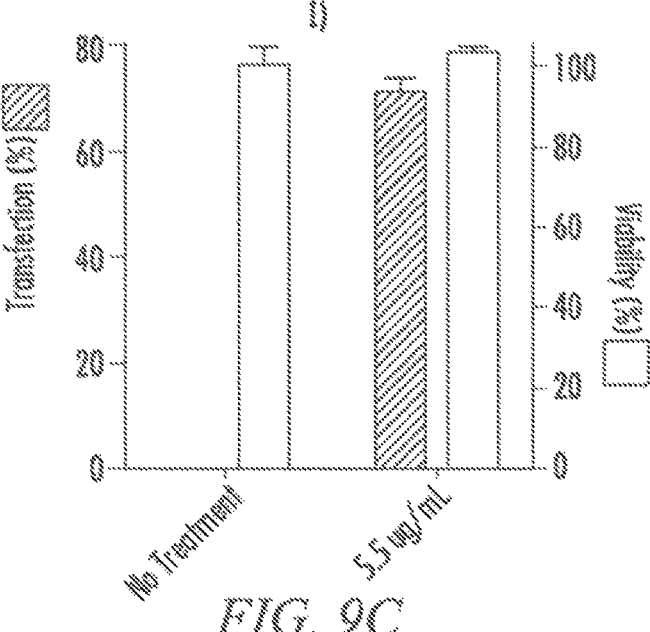
Figure 10A:
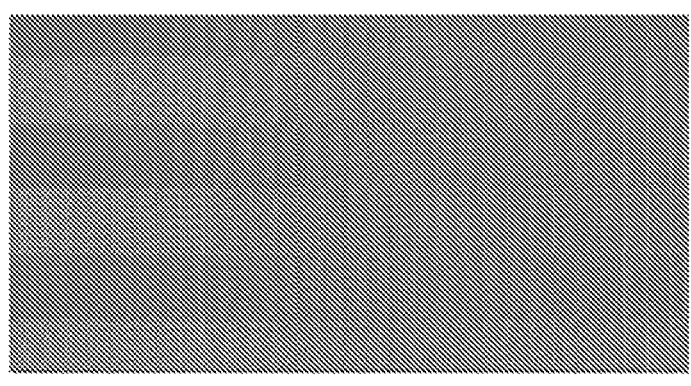
Figure 10B:
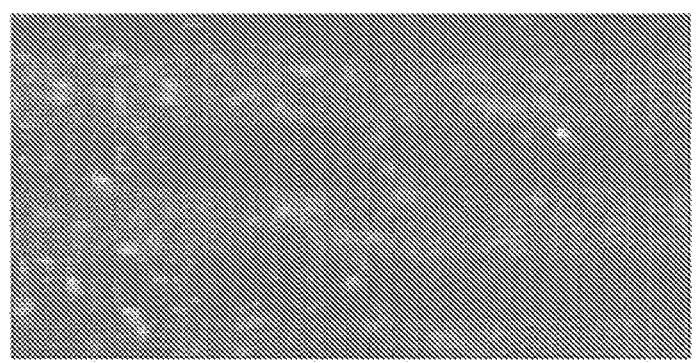
Figure 10C:
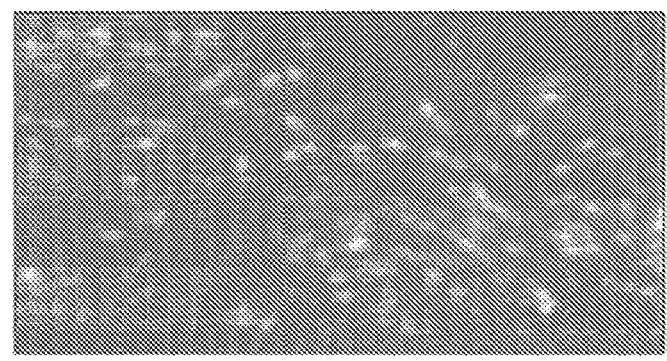
Figure 11A:
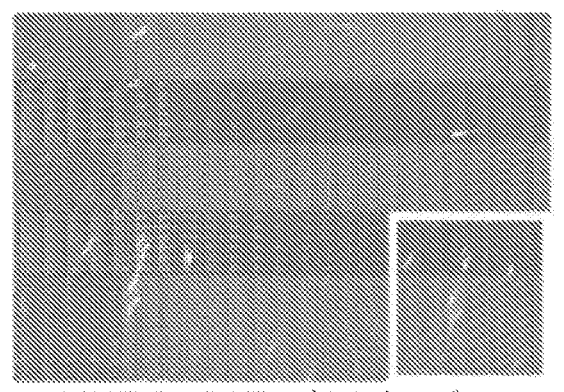
Figure 11B:
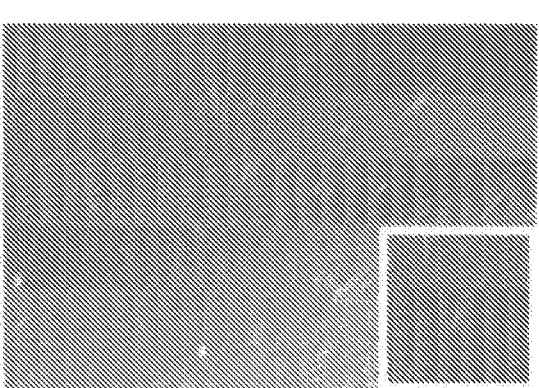
Figure 12:
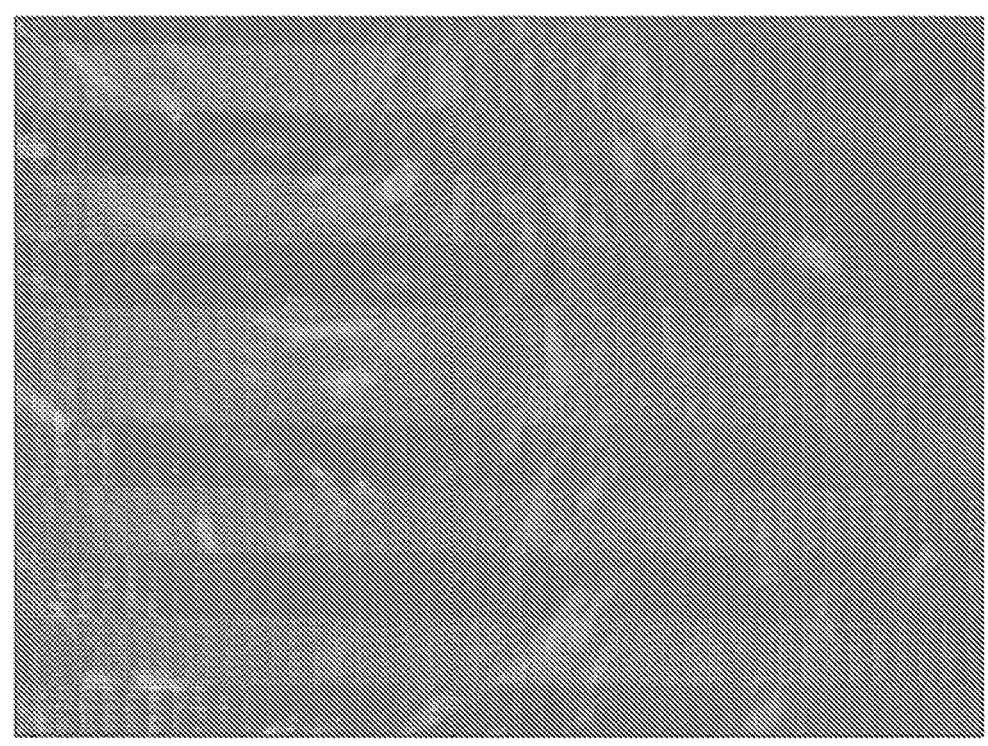
Figure 13:
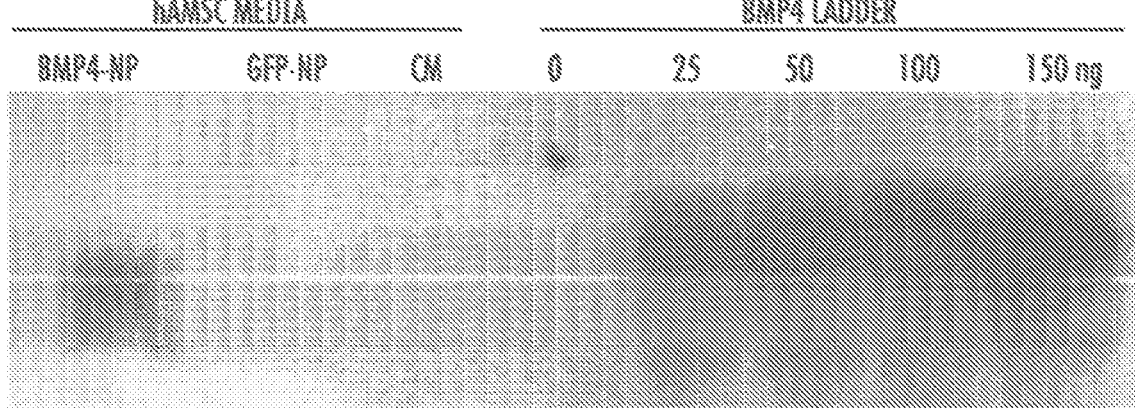
Figure 14A:
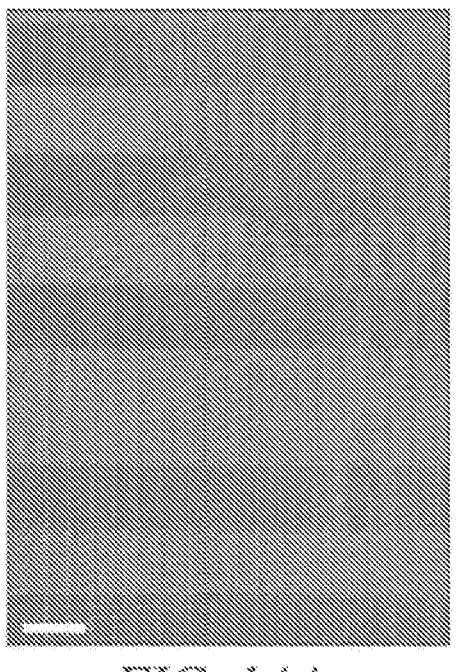
Figure 14B:
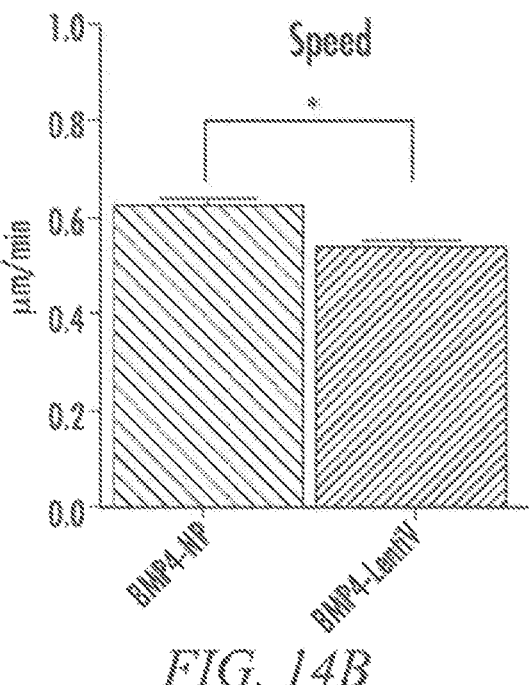
Figure 15A:
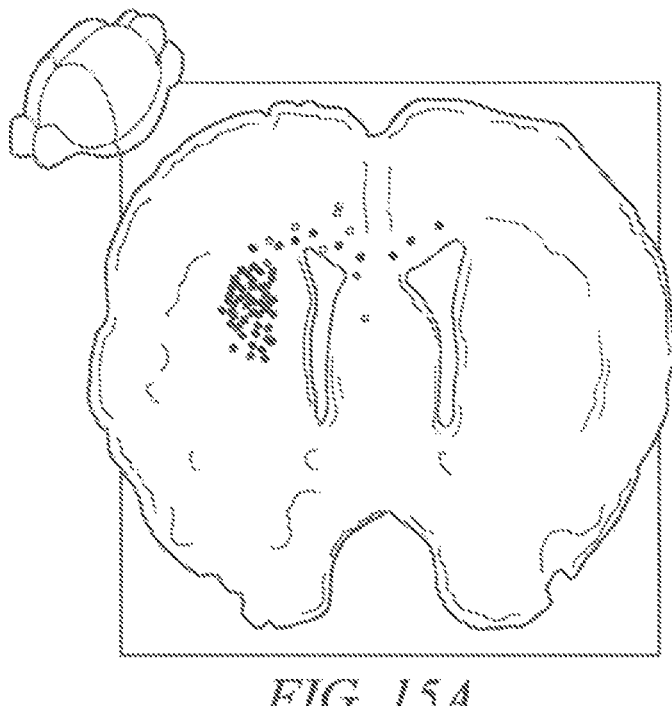
Figure 15B:
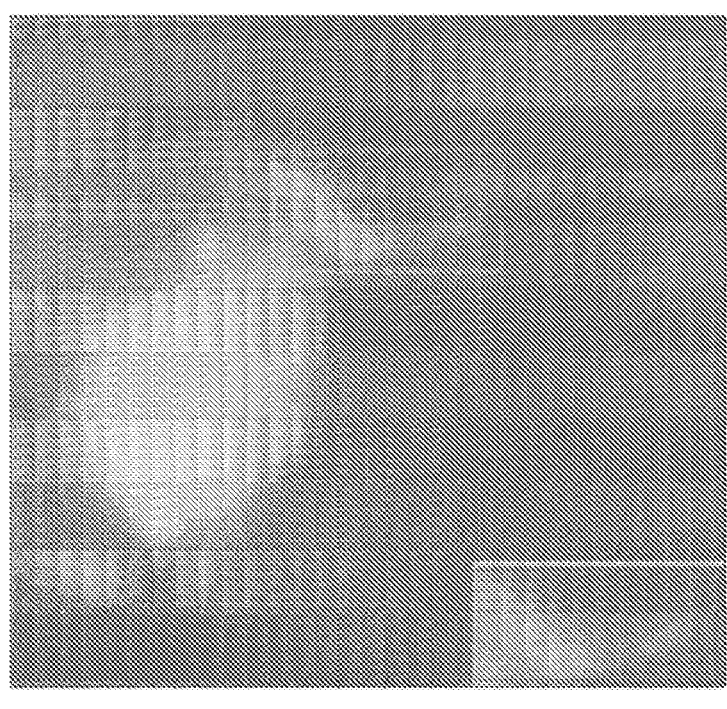
Figure 16A:
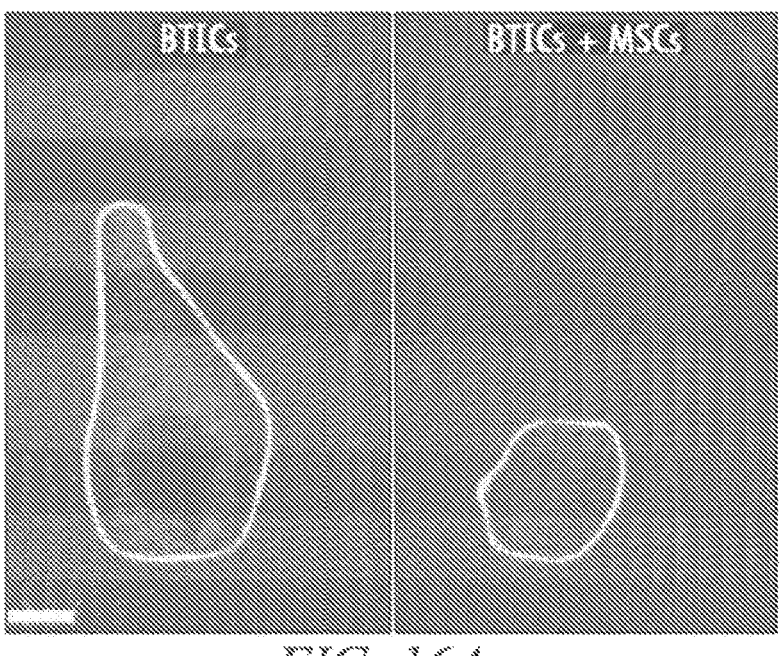
Figure 16B:
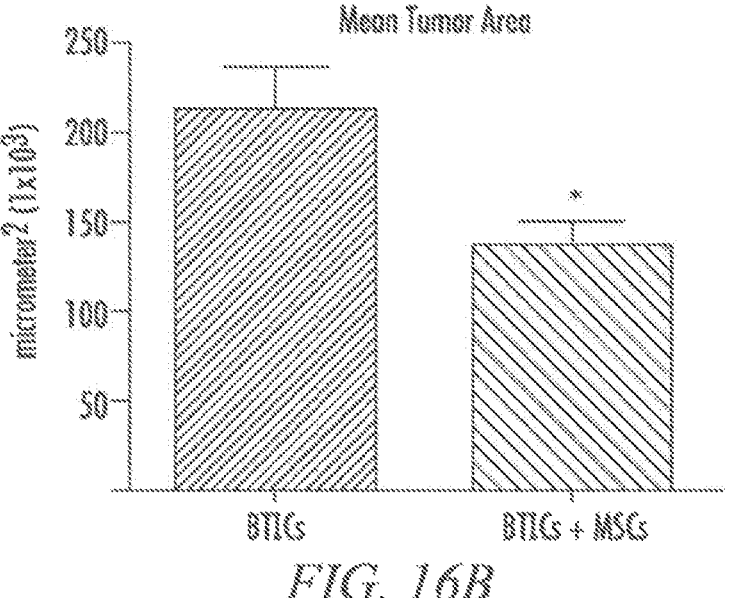
Figure 17A:
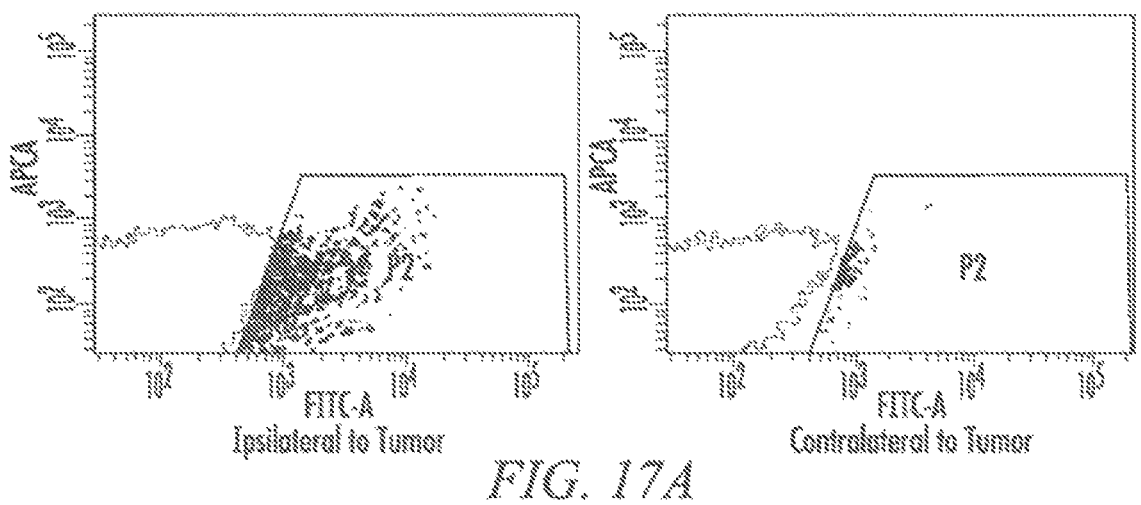
Figure 17B:
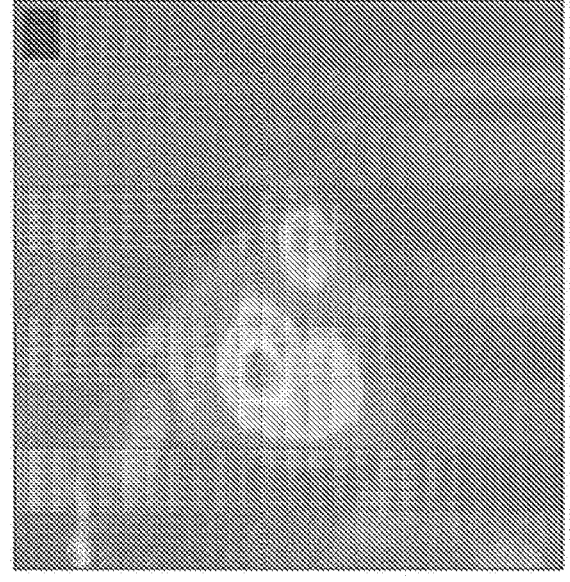
Figure 18A:
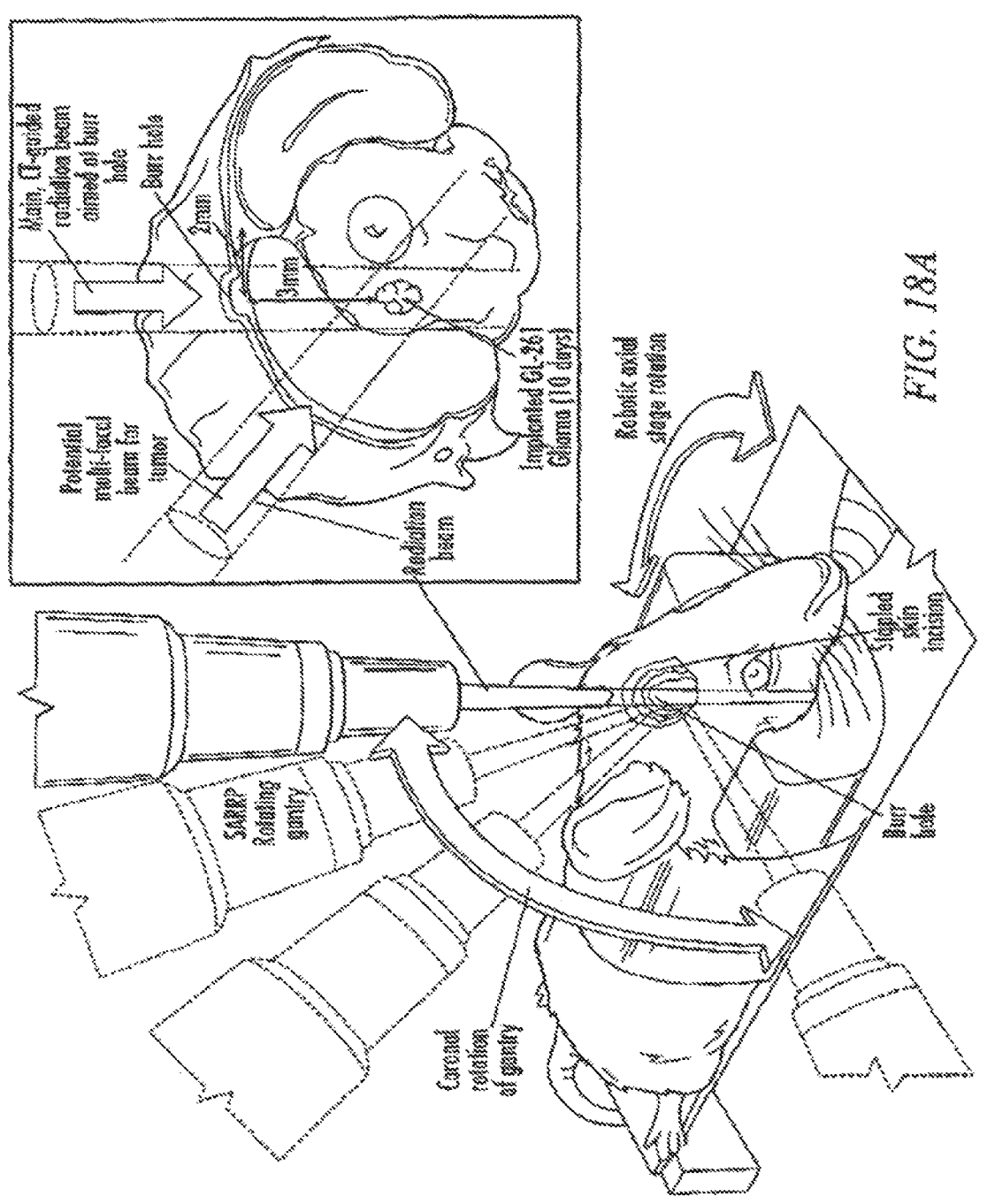
Figure 18B:
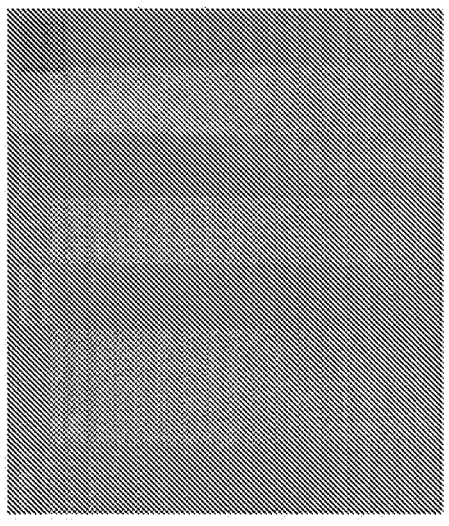
Figure 18C:
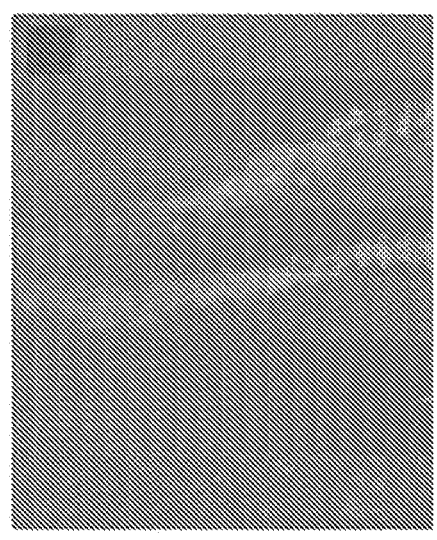
Figure 18D:
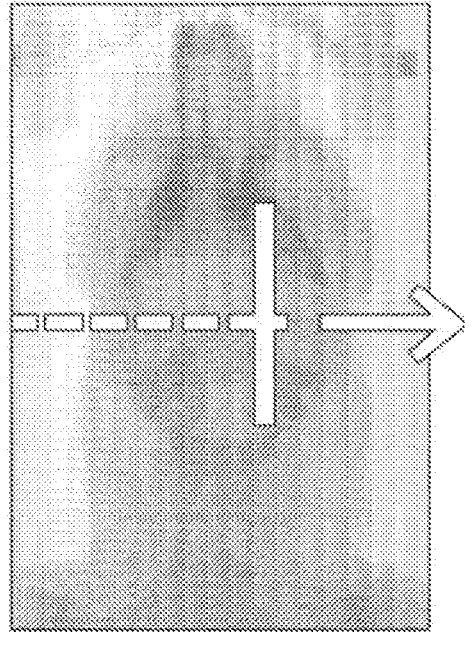
Figure 18E:
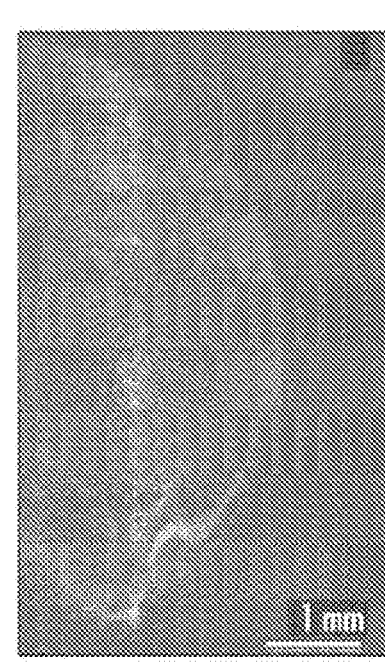
Figure 19:
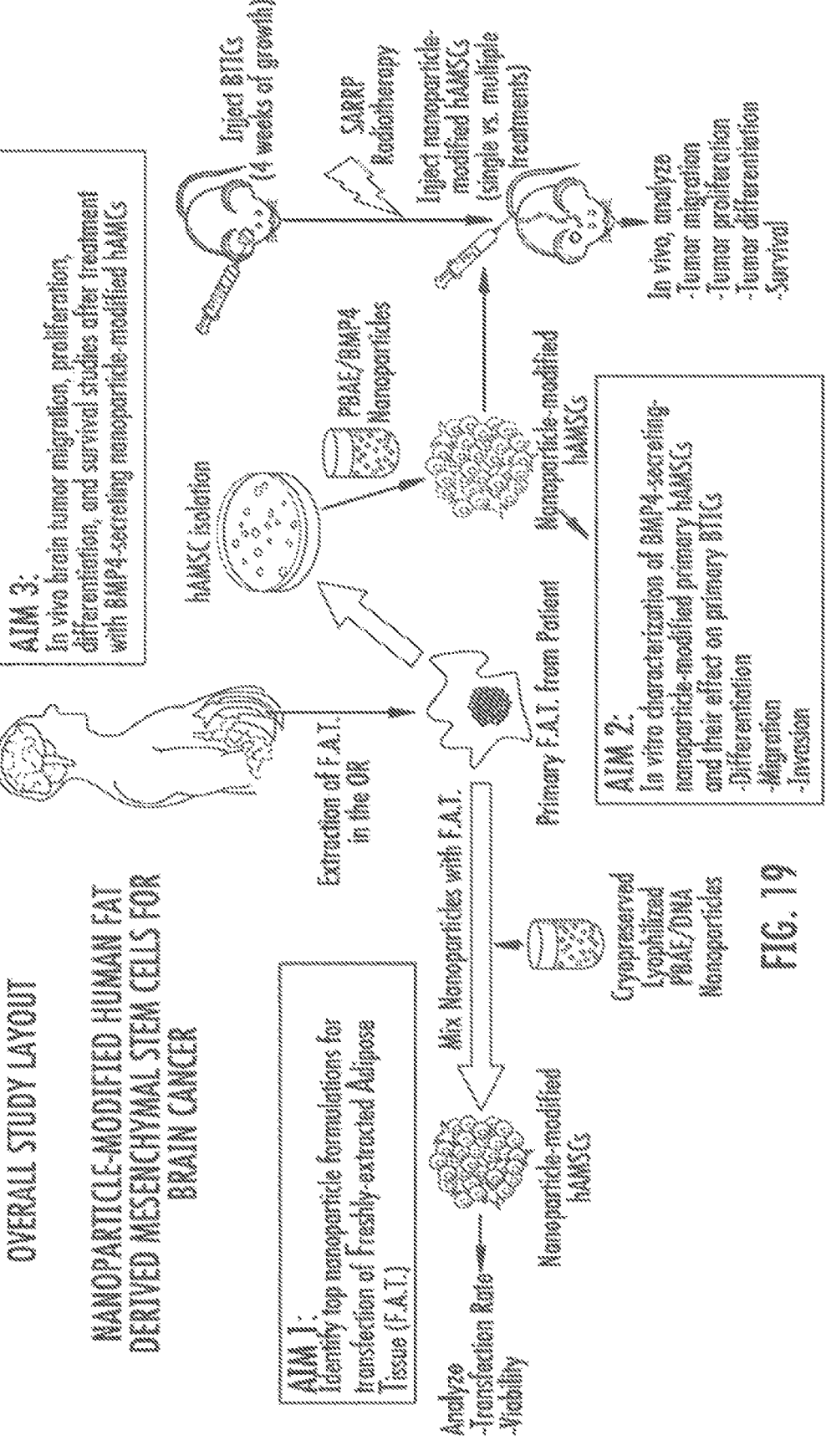
Figure 20:
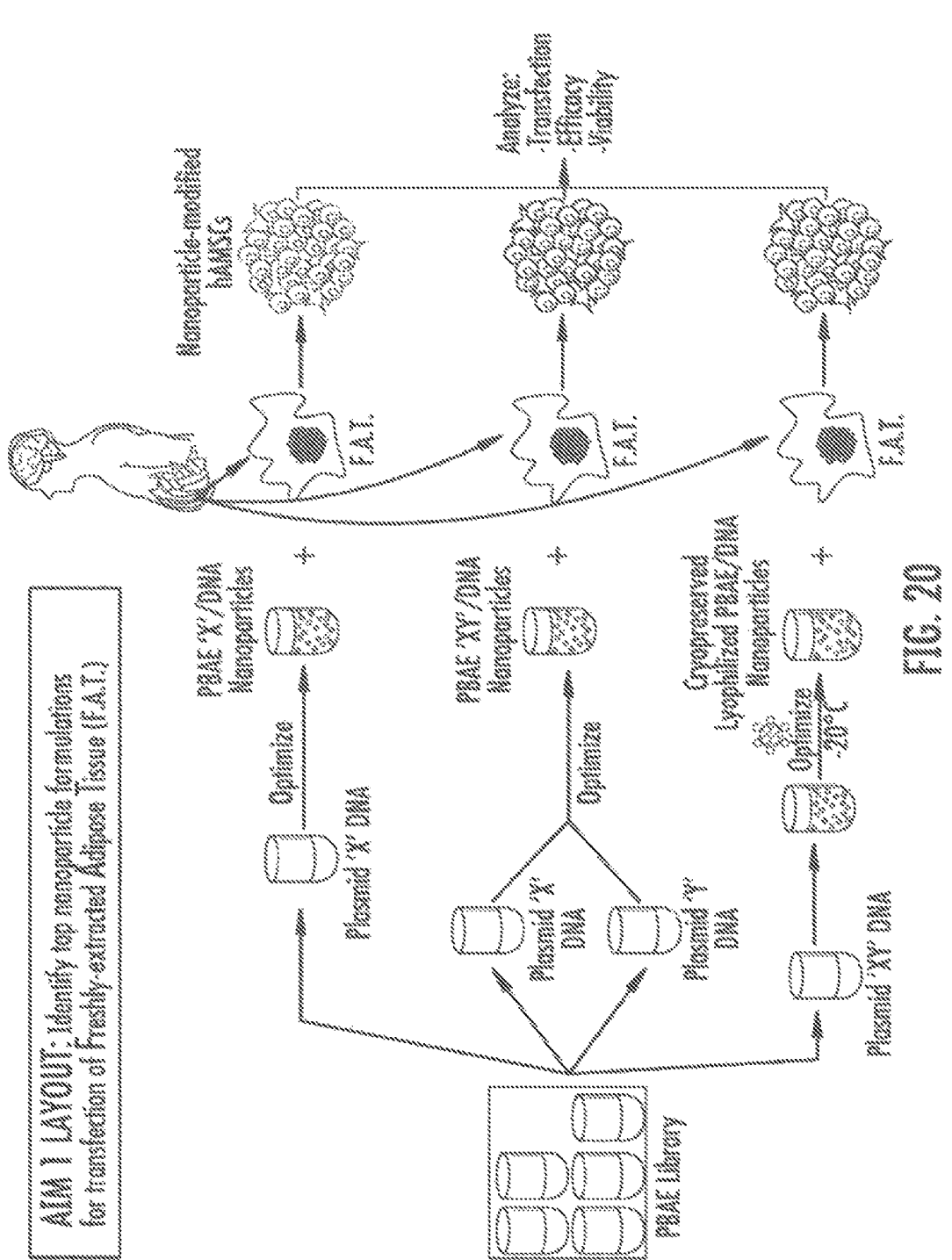
Figure 21:
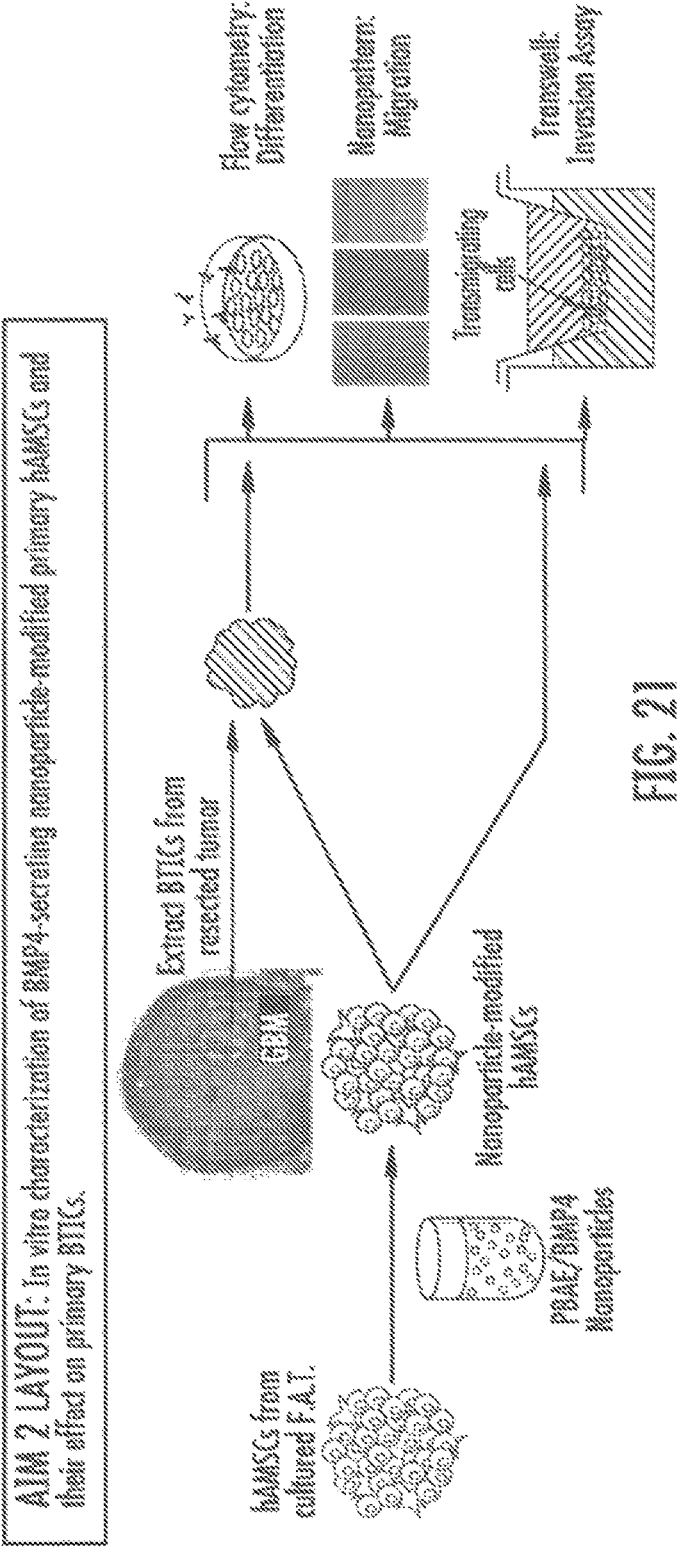
Figure 23A:
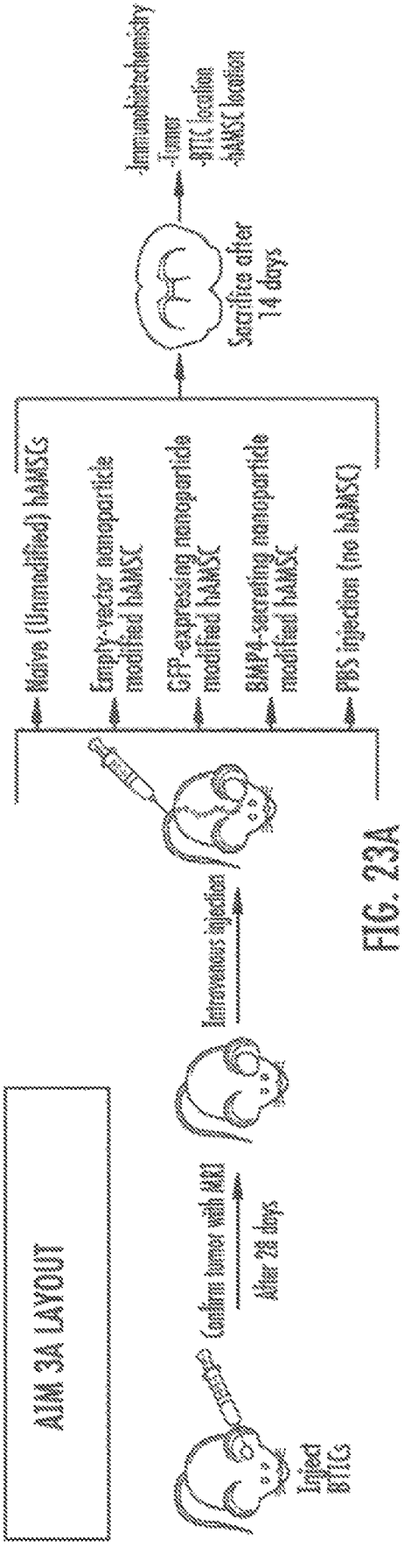
Figure 23B:
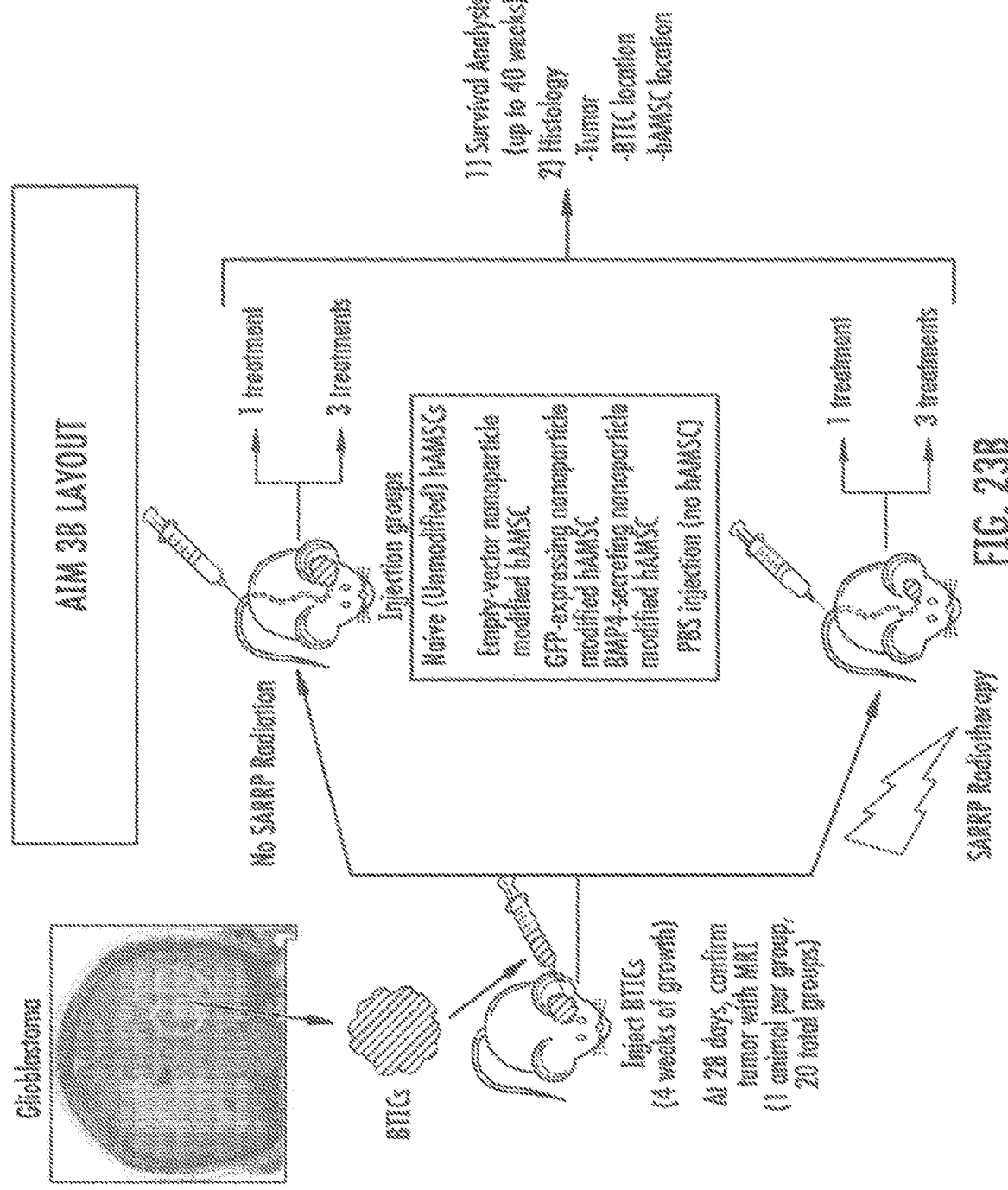

Having thus described the presently disclosed subject matter in general terms, reference will now be made to the accompanying Figures, which are not necessarily drawn to scale, and wherein:

FIG. 1 shows transfection of hAMSCs with an initial library of poly-p-amino-esters (PBAEs). Certain polymers (e.g. 446, 447, 357, and 453) compared favorably to leading commercial reagent Lipofectamine 2000 for transfection efficacy and cell viability;

FIG. 2A and FIG. 2B show: freshly-extracted adipose tissue (F.A.T) after transfection with 20 μL of 536-40 w/w GFP/PBAE nanoparticles (0.6 μg DNA) (FIG. 2A); and primary hAMSCs from F.A.T. in culture after transfection as stated in FIG. 2A (FIG. 2B);

FIG. 3 shows transfection efficacy of 447-based DNA nanoparticles lyophilized with sucrose after storage at −20° C. Particles showed the same efficacy as freshly prepared particles even after 2 years of storage. (Modified from Guerrero-Cazares et al, 2014);

FIG. 4A and FIG. 4B show hAMSCs home to BTIC-derived tumor mass in vivo: BTICs (AQH276) were intracranially administered to nude mice. Four weeks post-administration. GFP-hAMSCs (Invitrogen) were administered systemically. Mice were sacrificed 2 weeks later (FIG. 4A); and brain sections were stained for GFP (hAMSCs) and nestin (BTICs). DAPI was used to identify tumor mass (FIG. 4B). Scale bars 200 μm. (Modified from Li et al, 2014);

FIG. 5 shows that exogenous BMP4 does not induce the differentiation of hAMSCs, hAMSCs were cultured in control media, differentiation media, or treated with BMP4 (100 ng/niL) for 3 weeks. Lineage stains were performed to assess differentiation ability. Scale bar, 100 μm. (Modified from Li et al., 2014);

FIG. 6 shows that treatment with BMP4-secreting hAMSCs increases survival in a mouse model of human GBM. Mice were implanted with U87 GBM cells and 10 days after injection were treated with a single systemic injection of PBS, naïve hAMSCs, or virally-modified BMP4-secreting hAMSCs. Mice treated with virally-modified BMP4-secreting hAMSCs had significantly increased survival times compared to mice treated with PBS (p=0.002) or naïve hAMSCs (p=0.01). *p<0.05 (Modified from Li et al., 2014);

FIG. 7 shows a representative polymer synthesis scheme. Conjugate addition of amines to acrylates or acrylamides in two steps. The three R groups allow modifications to the polymer backbone (R), side chain (R'), and end groups (R"). Each monomer composes either the backbone (B), side chain (S), or end-group (E). Through this procedure, up to 150 novel biodegradable polymers can be evaluated. Polymers directly self-assemble with DNA to form nanoparticles and are added to cells following a high-throughput 96-well plate protocol;

FIG. 8A and FIG. 8B show particular polymer formulations effective for the presently disclosed subject matter (x-axis) and non-viral transfection of adipose-derived human primary mesenchymal stem cells (5 different primary cell samples as indicated in the legend). Data indicates robustness of the presently disclosed subject matter. Transfection is significantly higher, both as the percentage of cells positively transfected and average transfection amount per cell, than a leading commercially available reagent, Lipofectanine 2000. All measurements were conducted by flow cytometry for quantification. Polymer stnictures correspond to the chemical structures key shown FIG. 7;

FIG. 9A. FIG. 9B and FIG. 9C show primary hAMSCs (1082 cells) four days after transfection with 536 40 w/w PBAE/GFP nanoparticles (images above show phase contrast and images below show GFP fluorescence); no treatment (FIG. 9A); 40 uL dosage (FIG. 9B); and graph showing viability and % transfection of primary AMSCs four days after transfection (FIG. 9C);

FIG. 10A, FIG. 10B and FIG. 10C show hAMSCs two days after transfection with: control (no treatment) (FIG. 10A); conventional GFP plasmid (FIG. 10B; and CpG free GFP plasmid (FIG. 10C). All images show fluorescence on the GFP channel;

FIG. 11A and FIG. 11B show co-transfection of human fibroblasts with GFP and DsRed plasmids: FIG. 11A demonstrates that within the same PBAE nanoparticle shows coexpression; and FIG. 11B demonstrates that separate particles do not show coexpression;

FIG. 12 shows that exogenous GFP expression to hAMSCs with PBAEs lasts at least 7 days;

FIG. 13 shows that hAMSC engineered with nanoparticle-delivery C1 BMP 4 plasmid secrete BMP4 extracellularly as shown by Western blot for BMP4 protein (25 kDa) in nanoparticle-engineered hAMSC conditioned media;

FIG. 14A and FIG. 14B show: electron microscope image of hAMSCs migrating on 3D nanopattern model (FIG. 14A); and quantification of migration speed of nanoparticle-modified BMP4-secreting hAMSCs and lentivirally-modified BMP4-secreting hAMSCs showed that nanoparticle-modified hAMSCs had greater motility than lentivirally-modified hAMSCs (FIG. 14B). Quantification was performed on a 3D nanopattern model by 15 hr timelapse. *p<0.05. (Modified from Mangraviti et al. 2014 and Smith et al, 2013);

FIG. 15A and FIG. 15B show migration of gliomas in vivo: schematic of transcallosal spread of human brain tumor initiating cells (BTICs) after implantation into right striatum of a nude mouse (FIG. 15A); and coronal section demonstrating transcallosal (dashed box and inset) spread of a GFP-BTIC established in previous efforts (FIG. 15B; modified from Garzon-Muvdi et al, 2009);

FIG. 16A and FIG. 16B show that treatment with BMP4-secreting hAMSCs decreased tumor size in a mouse model of human GBM. Mice were injected with either BTICs alone or co-injected with BTICs and hAMSCs and sacrificed 4 weeks later; representative image (FIG. 16A); and quantification of mean tumor area. Co-injection with BTICs and hAMSCs resulted in a smaller mean tumor area *p=0.019. (FIG. 16B; modified from Li et al, 2014);

FIG. 17A and FIG. 17B show that systemically administered nanoparticle-modified hAMSCs localize to intracranial tumor. Mice with human gliomas were administered nanoparticle-modified GFP-labeled or nanoparticle-modified luciferase-expressing hAMSCs to determine their ability to localize to brain tumors; flow cytometry for nanoparticle-modified GFP-expressing hAMSCs showed increased presence of nanoparticle-modified GFP-expressing hAMSCs in the brain ipsilateral to the tumor (FIG. 17A); and bioluminescence live-animal imaging after systemic administration of nanoparticle-modified luciferase-expressing hAMSCs demonstrated localization of hAMSCs to the brain, with preferential migration of hAMSCs ipsilateral to the tumor, hAMSCs can be used as "Trojan horses" to deliver genes of interest to brain tumors. (FIG. 17B; modified from Mangraviti et al., 2014);

FIG. 18A, FIG. 18B. FIG. 18C, FIG. 18D and FIG. 18E show precise delivery of radiation using the small animal radiation research platform (SARRP); image of SAARP with mouse (FIG. 18A); γH2Aχ ICC demonstrating radiation-related changes following 10 Gy delivery to left hippocampus (FIG. 18B and FIG. 18C); compared with non-irradiated, contralateral hippocampus (FIG. 18C); precision planar irradiation planning with 10 Gy radiation through a 1-mm diameter beam (FIG. 18D; red bar); and γH2Aχ iCC from the section of radiated brain illustrated in FIG. 18D (FIG. 18E). (Modified from Ford et al., 2011 and Zeng et al, 2013);

FIG. 19 shows a representative overall layout for studying nanoparticle-modified human fat derived mesenchymal stem cells for brain cancer;

FIG. 20 shows a representative layout for Aim 1 to identify top nanoparticle formulations for transfection of Freshly-extracted Adipose Tissue (F.A.T.);

FIG. 21 shows a representative layout for Aim 2 for in vitro characterization of BMP4-secreting nanoparticle-modified primary hAMSCs and their effect on primary BTICs;

FIG. 22 shows a representative layout for Aim 3 for in vivo brain tumor migration, proliferation, differentiation, and survival studies after treatment with BMP4-secreting nanoparticle-modified hAMSCs; and FIG. 23A and FIG. 23B show representative layouts for Aim 3A, to determine the effect of nanoparticle-modified BMP4-secreting primary hAMSCs on tumor progression and survival in a murine human GBM model in vivo (FIG. 23A); and Aim 3B, to determine if multiple treatments of nanoparticle modified primary hAMSCs in combination with precise radiotherapy maximizes antiglioma effect in vivo, including survival (FIG. 23B).

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications; Ausubel. F., et al, (eds.), *Current*

*Protocols in Molecular Biology, Current Protocols in Immunology, Current Protocols in Protein Science,* and *Current Protocols in Cell Biology,* all John Wiley & Sons. N.Y., edition as of December 2008; Sambrook, Russell, and Sambrook, *Molecular Cloning. A Laboratory Manual.* $3^{rd}$ ed., Cold Spring Harbor Laboratory Press, Cold Spring Harbor, 2001; Harlow, E, and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung. B. (ed.) Basic and Clinical Pharmacology, McGraw-Hill/Appleton & Lange $10^{th}$ ed. (2006) or 11th edition (July 2009). Non-limiting information regarding genes and genetic disorders is found in McKusick, V. A.; Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine. Johns Hopkins University (Baltimore, Md.) and National Center for Biotechnology Information, National Library of Medicine (Bethesda, Md.), as of May 1, 2010. World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact-.shtml.

Glioblastoma (GBM) is the most common primary brain tumor in adults, and accounts for 20% of all primary brain tumors. GBM has a median survival rate of only 14.6 months despite current best treatment practices including surgery and chemoradiation. A significant reason for this morbidity and mortality is the ability of GBM to invade normal brain parenchyma, making localized treatment ineffective.

There is increasing evidence that a small subset of brain tumor initiating cells (BTICs) is responsible for GBM's treatment resistance. In order for treatment to be effective, these invading cells need to be targeted. One promising approach involves the use of mesenchymal stem cells (MSCs), which have been found to migrate preferentially to and home in on cancer cells. Moreover, MSCs can be engineered to synthesize and release anti-tumor proteins, like bone morphogenic protein 4 (BMP4), which affects BTICs.

MSCs can be obtained from bone marrow (BM-MSCs) and adipose tissue (AMSCs). BM-MSCs are difficult to obtain, have limited ex vivo proliferation capacity, and decrease in effectiveness with donor age. Unlike BM-MSCs, AMSCs are more abundant in supply, easier to obtain from fat tissue, express higher levels of surface markers implicated in cell migration, and have been shown to resist oncogenic transformation.

Primary human adipose-derived MSCs (hAMSCs), as compared to bone marrow-derived MSCs, have comparable GBM cell tropism, are more abundant in supply, express higher levels of surface markers implicated in cell migration, and have been shown to resist transformation (Li et al, 2014; Pendleton et al, 2013). Viral gene delivery has been used to modify MSCs to deliver therapeutic proteins for brain cancer (Li et al, 2014). However, this method of gene delivery is associated with insertional mutagenesis and immunogenicity, and, therefore, has potentially limited translational ability for use in human patients.

The presently disclosed subject matter relates to the discovery that human adipose-derived Mesenchymal Stem Cells (hAMSCs) can be engineered to synthesize and release anti-tumor proteins and therefore can be used as "Trojan Horses". As described more fully below, a novel technology has been created comprising the use of biodegradable polymeric nanoparticles combined with Freshly-extracted Adipose Tissue (F.A.T.) from a patient (autologous cells). This technology non-virally engineers the F.A.T., including the primary hAMSCs contained within the F.A.T to secrete anti-cancer (anti-tumor) compounds, such as proteins, while maintaining the cells' ability to migrate toward tumor cells. Nanoparticle-modified hAMSCs can provide a treatment that is safe and effective for not only patients with primary brain cancer, but many types of metastatic brain cancers and other neurological diseases where cell therapy can enhance the delivery of a protein or a gene for treatment.

In one clinical application, the nanoparticle solution may be added to F.A.T, while the patient is undergoing surgery, with the resulting transfected hAMSCs administered to the patient during surgery, without the cells being processed. This technology is more easily translatable than cell therapy approaches that require cell culturing and numerous FDA regulations. However, in additional clinical applications, the nanoparticles may be added ex vivo to hAMSCs obtained from patient F.A.T, after culturing the hAMSCs (e.g., for a few days) and then the autologous cells administered to the patient as a treatment (e.g, intravenously).

Accordingly, the presently disclosed subject matter provides a revolutionary new way of facilitating personalized medicine for the treatment of patients with brain cancer and other neurological diseases.

I. Nanoparticle Formulations

In one embodiment, the presently disclosed subject matter provides a nanoparticle formulation comprising biodegradable polymers self-assembled with nucleic acid molecules. The biodegradable polymer may comprise, for example, biodegradable poly-p-amino-esters (PBAEs), poly(amido amines), polyesters including PLGA, polyanhydrides, bioreducible polymers, and other biodegradable polymers. In some embodiments, the biodegradable polymer is selected from the group consisting of 2-(3-aminopropylamino)ethanol end-modified poly(1,4-butanediol diacrylate-co-4-amino-1-butanol) (446), (1-(3-aminopropyl)-4-methylpiperazine end-modified poly(1,4-butanediol diacrylate-co-4-amino-1-butanol) (447), 2-(3-aminopropylamino)ethanol end-modified poly(1,4-butanediol diacrylate-co-5-amino-1-pentanol) (456), (1-(3-aminopropyl)-4-methylpiperazine end-modified poly(1,4-butanediol diacrylate-co-5-amino-1-pentanol) (457), 2-(3-aminopropylamino)ethanol end-modified poly(1,5 pentanediol diacrylate-co-3-amino-1-propanol) (536), and (1-(3-aminopropyl)-4-methylpiperazine-end-modified poly(1,5 pentanediol diacrylate-co-3-amino-1-propanol) (537).

As described more fully in the Examples below, biodegradable cationic PBAE polymers have been developed as novel systems for non-viral gene delivery (Tzeng, Guerrero-Cazares et al, 2011; Green et al, 2006; Green et al, 2009; Bhise et al., 2012; Shmueli et al, 2012; Sunshine et al, 2011; Lee et al, 2009; Tzeng, Yang et al, 2011; Green, Chiu et al, 2007; Harris et al, 2010). Polymers for use in the presently disclosed subject matter may be synthesized and characterized as previously described (Green, 2012; Tzeng, Guerrero- Cazares et al., 2011; Sunshine et al, 2011; Tzeng, Yang et al, 2011). For example, a two-step procedure may be used (FIG. 7). First, acrylate-terminated base polymers is synthesized through the conjugate addition of 3-amino-1-propanol (S3), 4-amino-1-butanol (S4), and 5-amino-1-pentanol (S5) to 1,3-propanediol diacrylate (B3) and 1,4-butanediol diacrylate (B4), and 1,5-pentanediol diacrylate (B5). Second, small amine-containing molecules (E3, E5, E6, E7, E8) are individually added as end-capping groups to each linear base polymer. Polymer structures and molecular weight may be carefully determined by $^1$H-NMR and gel permeation chromatography (GPC) as previously described (Sunshine et al, 2011). Preparative GPC may be used to control molecular weight. Synthesis takes place using a 1.1:1 acrylate to amine monomer molar ratio during the base polymer synthesis step and 10 kDa polymers will be selected through preparative GPC. Additional information on polymers of use herein can be found in WIPO Patent Application Publication Nos. WO/2010/132879, WO/2014/06681 t. WO/2014/197892, and U.S. Patent Application Publication Nos. US2012/0128782 and US2012/0114759, each of which is incorporated herein by reference in its entirety for the teachings therein.

The nanoparticle formulations can be provided with a polymer to nucleic acid mass ratio, for example, to optimize transfection of nucleic acid. The polymer to nucleic acid ratio may vary from 1 to 99 weight polymer:weight nucleic acid to 50 to 50 weight polymer:weight nucleic acid. In some embodiments, the polymer to nucleic acid ratio may be 5 to 95 weight polymer:weight nucleic acid, 10 to 90 weight polymer:weight nucleic acid, 15 to 85 weight polymer:weight nucleic acid, 20 to 80 weight polymer:weight nucleic acid, 25 to 75 weight polymer:weight nucleic acid, 30 to 70 weight polymer:weight nucleic acid, 35 to 65 weight polymer weight nucleic acid, 40 to 60 weight polymer:weight nucleic acid, 45 to 55 weight polymer:weight nucleic acid, and 50 to 50 weight polymer:weight nucleic acid, In some embodiments, the nanoparticle formulation has a polymer to nucleic acid mass ratio of 25 to 75 weight polymer:weight nucleic acid.

Also as described more fully in the Examples below, nanoparticles of the presently disclosed subject matter may be formed from plasmids and polymers by self-assembly and incubation (e.g., in 25 mM aqueous sodium acetate at pH 5 for 10 min). Up to approximately 100 plasmids can be encapsulated in each polymeric nanoparticle (Bhise et al, 2012). Multiple plasmids can be co-delivered into the same cells, such as GFP and DsRed plasmids to human IMR90 fibroblasts (FIG. 11A and FIG. 11B).

As used herein, a "nucleic acid molecule" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA. DNA-RNA and RNA-RNA helices are possible. The term "nucleic acid molecule," and in particular DNA or RNA molecule, can refer only to the primary and secondary structure of the molecule, and does not limit it to any particular tertiary forms. Thus, this term includes double-stranded DNA found, inter alia, in linear or circular DNA molecules e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" can be a DNA molecule that has undergone a molecular biological manipulation.

A "plasmid" is a circular double stranded DNA loop into which additional DNA segments can be inserted, such as by standard molecular cloning techniques. A plasmid is a type of "vector", which is a nucleic acid molecule capable of transporting another nucleic acid to which it has been linked. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host ceil upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the presently disclosed subject matter in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

Within a recombinant expression vector, "operabiy linked" is intended to mean that the nucleotide sequence of interest is linked to the regulatory element(s) in a manner that allows for expression of the nucleotide sequence (e.g, in an in vitro transcription/translation system or in a host cell when the vector is introduced into the host ceil).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel (1990) Gene Expression Technology: Methods in Enzymology 185. Academic Press, San Diego, Calif. Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulator) elements may also direct expression in a temporal-dependent manner, such as in a cell-cycle dependent or developmental stage-dependent manner, which may or may not also be tissue or cell-type specific.

The nucleic acid molecules for use in the nanoparticle formulations of the presently disclosed subject matter encode one or more bioactive molecules functional in the treatment of a neurological disease. The one or more bioactive molecules may be selected from the group consisting of proteins, polypeptides, peptides, drugs, enzymes, hormones, RNA, and metabolites. In a particular embodiment, the neurological disease is a brain tumor, and the one or more bioactive molecules comprise one or more anti-cancer agents, particularly wherein the one or more anti-cancer agents are selected from the group consisting of bone morphogenic protein 4 (BMP4), TNF-related apoptosis-inducing ligand (TRAIL), HSV-thymidine kinase, an oncolytic adenovirus, interleukin-2 (IL-2), interieukin-12 (IL-12), interleukin-18 (IL-18), interleukin-2 3 (IL-23), Interferon-a, and Interferon-β.

In certain embodiments, the one or more bioactive molecules for use in the compositions and methods of the presently disclosed subject matter include RNA interfering agents. An "RNA interfering agent" as used herein, is defined as any agent which interferes with or inhibits expression of a target gene, e.g., a marker of the presently disclosed subject matter, by RNA interference (RNAi). Such RNA interfering agents include, but are not limited to, nucleic acid molecules including RNA molecules which are homologous to the target gene, e.g., a marker of the presently disclosed subject matter, or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn & Cullen (2002) J. Virol. 76:9225), thereby inhibiting expression of the target gene (see, e.g., U.S. Patent Application Nos: 20030153519A1; 20030167490A1; and U.S. Pat. Nos. 6,506,559; 6,573,099). In one embodiment, the RNA is double stranded RNA (dsRNA). This process has been described in plants, invertebrates, and mammalian cells. In nature. RNAi is initiated by the dsRNA-specific endonuclease Dicer, which promotes processive cleavage of long dsRNA into double-stranded fragments termed siRNAs, siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes.

The presently disclosed subject matter also contemplates "short interfering RNA" (siRNA), also referred to herein as "small interfering RNA." Such a molecule is defined as an agent which functions to inhibit expression of a target gene, e.g., by RNAi. As used herein, the term siRNA is intended to be equivalent to any term in the art defined as a molecule capable of mediating sequence-specific RNAi. Such equivalents include, for example, double-stranded RNA (dsRNA), microRNA (mRNA), short hairpin RNA (shRNA), short interfering oligonucleotide, and post-transcriptional gene silencing RNA (ptgsRNA). An siRNA may be chemically synthesized, may be produced by in vitro transcription, or may be produced within a host cell. In one embodiment, siRNA is a double stranded RNA (dsRNA) molecule of about 15 to about 40 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter.

The nanoparticle formulation may be lyophilized. Lyophilization, also known as freeze-drying, is a process which consists of removing water from a frozen sample by sublimation and desorption under vacuum. When taking into account physical, chemical and engineering principles, freeze-drying of colloidal systems can be controlled in order to reach a shelf life of several years. However, this process can generate various stresses during freezing and drying steps so protectants are usually added to the formulation to protect the nanoparticles from freezing and desiccation stresses. For example, in the presently disclosed subject matter, lyoprotectants such as sucrose may also be utilized (Guerrero-Cazares et al., 2014; Tzeng. Guerrero-Cazares et al, 2011).

II. Freshly Extracted Adipose Tissue Cells

In another embodiment, the presently disclosed subject matter provides a freshly extracted adipose tissue cell comprising at least one nanoparticle, wherein the nanoparticle comprises a biodegradable polymer self-assembled with a nucleic acid molecule. The biodegradable polymer may comprise, for example, biodegradable poly-p-amino-esters (PBAEs), poly(amido amines), polyesters including PLGA, polyanhydrides, bioreducible polymers, and other biodegradable polymers. In some embodiments, the biodegradable polymer is selected from the group consisting of 2-(3-aminopropylamino)ethanol end-modified poly(1,4-butanediol diacrylate-co-4-amino-1-butanol) (446), (1-(3-aminopropyl)-4-methylpiperazine end-modified poly(1,4-butanediol diacrylate-co-4-amino-1-butanol) (447), 2-(3-aminopropylamino)ethanol end-modified poly(1,4-butanediol diacrylate-co-5-amino-1-pentanol) (456), (1-(3-aminopropyl)-4-methylpiperazine end-modified poly(1,4-butanediol diacrylate-co-5-amino-1-pentanol) (457), 2-(3-aminopropylamino)ethanol end-modified poly(1,5 pentanediol diacrylate-co-3-amino-1-propanol) (536), and (1-(3-aminopropyl)-4-methylpiperazine-end-modified poly(1,5 pentanediol diacrylate-co-3-amino-1-propanol) (537). In some embodiments, the freshly extracted adipose tissue cell comprises an adipose-derived mesenchymal stem cells (AMSC).

By "adipose tissue" is meant any fat tissue. The adipose tissue may be brown or white adipose tissue, derived from subcutaneous, omental/visceral, mammary, gonadal, or other adipose tissue site, e.g., the adipose tissue is subcutaneous white adipose tissue.

The term "adipose-derived mesenchymal cells" or "AMSCs", as used herein, refers to cells that originate from adipose tissue and are phenotypically characterized in that they are (i) negative for at least one, two, three, four, five, six, seven, eight, nine, ten or preferably all of the following markers CD3, CD11b, CD14, CD19, CD31, CD34, CD45, CD62L, CD95L, CD117, and HLA-DR cell surface markers, and (ii) positive for at least one, two, three, four, five, six, seven, eight or preferably all of the following markers CD13, CD29, CD44, CD49e, CD73, CD90, CD105, CD166, and HLA-ABC cell surface markers.

The nucleic acid molecules for use in the freshly extracted adipose tissue cell s of the presently disclosed subject matter encode one or more bioactive molecules functional in the treatment of a neurological disease. The one or more bioactive molecules may be selected from the group consisting of proteins, polypeptides, peptides, drugs, enzymes, hormones, RNA, and metabolites. In a particular embodiment, the neurological disease is a brain tumor, and the one or more bioactive molecules comprise one or more anti-cancer agents, particularly wherein the one or more anti-cancer agents are selected from the group consisting of bone morphogenic protein 4 (BMP4), TNF-related apoptosis-inducing ligand (TRAIL). HSV-thymidine kinase, an oncolytic adenovirus, interleukin-2 (IL-2), interleukin-12 (IL-12), interleukin-18 (IL-18), interleukin-23 (IL-23), Interferon-a, and Interferon-β.

III. Methods for Treating Neurological Diseases

The freshly extracted adipose tissue cells may be transfected during a surgery on the patient such that the nanoparticles are combined with freshly-extracted adipose tissue to form a suspension, a cellular fraction comprising freshly extracted adipose tissue cells transfected with the nucleic acid molecules is extracted from the suspension, and the freshly extracted adipose tissue cells transfected with the nucleic acid molecules are administered to the patient undergoing surgery without the cells being processed. The nanoparticles may also be added to processed AMSCs from freshly extracted adipose tissue (i.e., AMSCs that have been isolated, purified, and cultured).

Accordingly, in one embodiment, the presently disclosed subject matter provides a method for treating a neurological disease in a patient in need thereof, the method comprising: a) obtaining freshly extracted adipose tissue from the patient; b) transfecting cells in the freshly extracted adipose tissue, wherein transfecting comprises combining the freshly extracted adipose tissue with a nanoparticle formulation to form a suspension, wherein the nanoparticle formulation comprises biodegradable polymers self-assembled with nucleic acid molecules, and wherein the nucleic acid molecules encode one or more bioactive molecules functional in the treatment of a neurological disease; c) extracting a cellular fraction from the suspension, wherein the cellular fraction comprises freshly extracted adipose tissue cells transfected with the nucleic acid molecules; and d) administering the freshly extracted adipose tissue cells transfected with the nucleic acid molecules to the patient. In some embodiments, the freshly extracted adipose tissue cells transfected with the nucleic acid molecules comprise adipose-derived mesenchymal stem cells (AMSCs). The freshly extracted adipose tissue cells transfected with the nucleic acid molecules may be administered to the patient systemically or intracranially. The nanoparticle formulation may also be lyophilized prior to combining with the freshly extracted adipose tissue to form a suspension.

In another embodiment, the presently disclosed subject matter provides a method for treating a neurological disease in a patient in need thereof, the method comprising: a) obtaining freshly extracted adipose tissue from the patient, wherein the freshly extracted adipose tissue comprises adipose-derived mesenchymal stem cells (AMSCs); b) isolating and purifying the AMSCs; c) culturing the AMSCs under conditions allowing for proliferation of the AMSCs; d) transfecting the AMSCs, wherein transfecting comprises combining the freshly extracted adipose tissue with a nanoparticle formulation, wherein the nanoparticle formulation comprises biodegradable polymers self-assembled with nucleic acid molecules, and wherein the nucleic acid molecules encode one or more bioactive molecules functional in the treatment of a neurological disease; and e) administering the AMSCs transfected with the nucleic acid molecules to the patient. The AMSCs transfected with the nucleic acid molecules may be administered to the patient systemically.

The biodegradable polymer may comprise, for example, biodegradable poly-p-amino-esters (PBAEs), poly(amido amines), polyesters including PLGA, polyanhydrides, bioreducible polymers, and other biodegradable polymers. In some embodiments, the biodegradable polymer is selected from the group consisting of 2-(3-aminopropylamino)ethanol end-modified poly(1,4-butanediol diacrylate-co-4-amino-1-butanol) (446), (1-(3-aminopropyl)-4-methylpiperazine end-modified poly(1,4-butanediol diacrylate-co-4-amino-1-butanol) (447), 2-(3-aminopropylamino)ethanol end-modified poly(1,4-butanediol diacrylate-co-5-amino-1-pentanol) (456), (1-(3-aminopropyl)-4-methylpiperazine end-modified poly(1,4-butanediol diacrylate-co-5-amino-1-pentanol) (457), 2-(3-aminopropylamino)ethanol end-modified poly(1,5 pentanediol diacrylate-co-3-amino-1-propanol) (536), and (1-(3-aminopropyl)-4-methylpiperazine-end-modified poly(1,5 pentanediol diacrylate-co-3-amino-1-propanol) (537). In some embodiments, the freshly extracted adipose tissue cell comprises an adipose-derived mesenchymal stem cells (AMSC).

As used herein, the term "treating" can include reversing, alleviating, inhibiting the progression of, preventing or reducing the likelihood of the disease, disorder, or condition to which such term applies, or one or more symptoms or manifestations of such disease, disorder or condition. In some embodiments, "treating" means prolonging survival of patients, such as those having neurological diseases or neurodegenerative diseases, e.g., prolonging survival of a patient having a brain tumor, such as a GBM patient.

Administration of the AMSCs transfected with the nucleic acid molecules of the presently disclosed subject matter to the patient can be carried out by, for example, intravenous infusion; injection by intravenous, intraperitoneal, intracerebral, intramuscular, intraocular, intra-arterial or intralesional routes; or intracranial (intracerebral) application.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracranial or intracerebral use. AMSCs transfected with the nucleic acid molecules of the presently disclosed subject matter can be administered by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease.

In some embodiments, the presently disclosed subject matter provides compositions and methods for treating a neurological disease in a patient in need thereof. Such diseases, disorders, or conditions include, but are not limited to, glaucoma, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease. Parkinson's disease, Parkinson's-plus diseases, multiple system atrophy, progressive supranuclear palsy, corticobasal degeneration, dementia with Lewy bodies, frontotemporal dementia, demyelinating diseases. Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, and AIDS demential complex.

Other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoff s disease, Schilder's disease, subacute combined degeneration of spinal cord secondary to pernicious anemia. Spielmeyer-Vogt-Sjogren-Batten disease (also known as Batten disease), spinocerebellar ataxia (multiple types with varying characteristics), Steele-Richardson-Olszewski disease, and tabes *dorsalis*.

In a particular embodiment, the neurological disease within the compositions and methods of the presently disclosed subject matter is a brain tumor. A "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor, such cells may exist locally or circulate in the blood stream as independent cells. A "tumor," as used herein, refers to all neoplastic cell growth and proliferation, whether malignant or benign, and all precancerous and cancerous cells and tissues. A "solid tumor", as used herein, is an abnormal mass of tissue that generally does not contain cysts or liquid areas. In some embodiments, the solid tumor regresses or its growth is slowed or arrested after the solid tumor is treated with the presently disclosed methods. In other embodiments, the solid tumor is malignant.

The AMSCs transfected with the nucleic acid molecules may also be administered to the patient in combination with an additional therapeutic agent or treatment, particularly radiotherapy when the neurological disease is a brain tumor. Additional therapeutic agents may also include, but are not limited to, chemotherapeutic agents such as adriamycin, dexamethasone, vincristine, cyclophosphamide, fluorouracil, topotecan, taxol, interferons, and platinum derivatives. Other examples of agents with which the disclosed AMSCs transfected with the nucleic acid molecules may also be administered include, without limitation, anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors, such as acetylcholinesterase inhibitors. MAO inhibitors, interferons, anticonvulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders, such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as pan of a multiple dosage regimen, from the inhibitor-containing composition. Alternatively, these agents may be part of a single dosage form, mixed together with the inhibitor in a single composition.

The nucleic acid molecule for use in the methods of the presently disclosed subject matter may encode one or more bioactive molecules functional in the treatment of a neurological disease. The one or more bioactive molecules may be selected from the group consisting of proteins, polypeptides, peptides, drugs, enzymes, hormones, RNA, and metabolites. In a particular embodiment, the neurological disease is a brain tumor, and the one or more bioactive molecules comprise one or more anti-cancer agents, particularly wherein the one or more anti-cancer agents are selected from the group consisting of bone morphogenic protein 4 (BMP4), TNF-related apoptosis-inducing ligand (TRAIL), HSV-thymidine kinase, an oncolytic adenovirus, interleukin-2 (IL-2), interleukin-12 (IL-12), interleukin-18 (IL-18), interleukin-2 3 (IL-23), Interferon-a, and Interferon-β.

IV. Kits

In another embodiment, the presently disclosed subject matter provides a kit for transfecting freshly extracted adipose tissue cells comprising: a) a lyophilized nanoparticle formulation comprising biodegradable polymers self-assembled with nucleic acid molecules; and b) instructions for combining the freshly extracted adipose tissue cells with the nanoparticle formulation to form a suspension. In some embodiments, the freshly extracted adipose tissue cells transfected with the nucleic acid molecules comprise adipose-derived mesenchymal stem cells (AMSCs).

In general, a presently disclosed kit contains some or all of the components, reagents, supplies, and the like to practice a method according to the presently disclosed subject matter. In some embodiments, the term "kit" refers to any intended article of manufacture (e.g., a package or a container) comprising a lyophilized nanoparticle formulation comprising biodegradable polymers self-assembled with nucleic acid molecules and a set of particular instructions for transfecting AMSCs in freshly extracted adipose tissue. The kit can be packaged in a divided or undivided container, such as a carton, bottle, ampule, tube, etc. The presently disclosed compositions can be packaged in dried, lyophilized, or liquid form. Additional components provided can include vehicles for reconstitution of dried components. Preferably all such vehicles are sterile and apyrogenic so that they are suitable for injection into a patient without causing adverse reactions.

The biodegradable polymer for use in the kits of the presently disclosed subject matter may comprise, for example, biodegradable poly-p-amino-esters (PBAEs), poly (amido amines), polyesters including PLGA, polyanhydrides, bioreducible polymers, and other biodegradable polymers. In particular embodiments, the biodegradable polymer is selected from the group consisting of 2-(3-aminopropylamino)ethanol end-modified poly(1,4-butanediol diacrylate-co-4-amino-1-butanol) (446), (1-(3-aminopropyl)-4-methylpiperazine end-modified poly(1,4-butanediol diacrylate-co-4-amino-1-butanol) (447), 2-(3-aminopropylamino)ethanol end-modified poly(1,4-butanediol diacrylate-co-5-amino-1-pentanol) (456), (1-(3-aminopropyl)-4-methylpiperazine end-modified poly(1,4-butanediol diacrylate-co-5-amino-1-pentanol) (457), 2-(3-aminopropylamino)ethanol end-modified poly(1,5 pentanediol diacrylate-co-3-amino-1-propanol) (536), and (1-(3-aminopropyl)-4-methylpiperazine-end-modified poly (1,5 pentanediol diacrylate-co-3-amino-1-propanol) (537). In some embodiments, the nanoparticle formulation has a polymer to nucleic acid mass ratio of 25 to 75 weight polymer:weight nucleic acid.

The nucleic acid molecule for use in the kits of the presently disclosed subject matter may encode one or more bioactive molecules functional in the treatment of a neurological disease. The one or more bioactive molecules may be selected from the group consisting of proteins, polypeptides, peptides, drugs, enzymes, hormones, RNA, and metabolites. In a particular embodiment, the neurological disease is a brain tumor, and the one or more bioactive molecules comprise one or more anti-cancer agents, particularly wherein the one or more anti-cancer agents are selected from the group consisting of bone morphogenic protein 4 (BMP4), TNF-related apoptosis-inducing ligand (TRAIL), HSV-thymidine kinase, an oncolytic adenovirus, interleukin-2 (IL-2), interleukin-12 (IL-12), interleukin-18 (IL-18), interleukin-23 (IL-23), Interferon-a, and Interferon-β.

V. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Representative Overall Layout for Studying
Nanoparticle-Modified Human Fat-Derived
Mesenchymal Stem Cells for Brain Cancer Previous efforts have shown that primary human adipose-derived MSCs (hAMSCs), as compared to bone marrow-derived MSCs, have comparable GBM cell tropism, are more abundant in supply, express higher levels of surface markers implicated in cell migration, and have been shown to resist transformation (Li et al, 2014; Pendleton et al, 2013). Viral gene delivery has been used to modify MSCs to deliver therapeutic proteins for brain cancer (Li et al, 2014). However, this method of gene delivery is associated with insertional mutagenesis and immunogenicity, and, therefore, has potentially limited translational ability for use in human (Chaichana et al, 2011) patients. Biodegradable, polymeric nanoparticles enable effective non-viral gene delivery to multiple cell types, including hMSCs, while avoiding the problems typical of viruses (Mangraviti et al, submitted; Guerrero-Cazares et al, 2014; Bhise et al, 2013; Kozielski et al, 2013; Shmueli et al, 2013; Green, 2012; Kozielski et al, 2014; Hollon, 2000; Check, 2005). The presently disclosed subject matter uses nanoparticles to non-virally engineer hAMSCs to secrete anti-cancer proteins while maintaining the cells' ability to migrate toward tumor cells. These nanoparticle-engineered hAMSCs are effective, minimally invasive, and translatable therapy. The overall layout of the study includes further optimization of the nanoparticles for effective non-viral gene delivery to primary hAMSCs in a convenient, clinically relevant way that minimizes ex vivo cell culture, demonstration that nanoparticle-modified hAMSCs retain their original phenotype and continue to secrete therapeutic molecules to suppress GBM, and determination of the safety and efficacy of nanoparticle-modified hAMSCs against primary GBM tumors. Therefore, the overall hypothesis that nanoparticle-engineered hAMSCs constitute an effective treatment against intracranial GBM will be tested (FIG. 19).

To this end, previous efforts have established several human BTIC lines validated through sphere assay and xenograft transplants from intraoperatively-obtained GBM (Chaichana et al, 2009; Chaichana et al, 2006; Guerrero-Cazares et al, 2009; Garzon-Muvdi et al, 2012; Chesler et al, 2012; Guerrero-Cazares et al, 2012; Li et al, 2011; Tzeng et al, 2011; Ying, Wang et al, 2011; Ying, Sang et al, 2011; Sun et al, 2009; Sanai et al, 2004). Cellular therapy, namely stem cell therapy, may be an effective treatment option because of its ability to home to cancer cells (Li et al, 2014; Ahmed et al, 2011; Frank et al, 2010; Aboody et al, 2013), hAMSCs are a novel therapeutic delivery vehicle and previous efforts have shown that hAMSCs (both commercial cell lines and primary-established cultures from intraoperative samples) have comparable glioma cell tropism (Pendleton et al, 2013); but, unlike Bone Marrow-MSCs, hAMSCs are more abundant, easier to obtain, express higher levels of surface markers implicated in cell migration, and have been shown to resist oncogenic transformation (Li et al, 2014; Vilalta et al, 2008). Previous efforts have shown that in vivo, hAMSCs show tropism to human orthotopic gliomas in mice serving as "Trojan horses" to deliver BMP4 and reduce GBM proliferation and migration by targeting BTICs (Li et al, 2014). Conventional modification of the hAMSCs occurs through viral methods (Li et al, 2014), but viral modification raises concerns in clinical applications such as insertional mutagenesis (Check, 2005) and life-threatening immune reactions (Hollon, 2000). To avoid these issues, hAMSCs from F.A.T. (Li et al, 2014; Mangraviti et al, submitted; Pendleton et al, 2013) will be modified using non-viral nanoparticles comprising a polymer PBAE and the DNA plasmid required to express gene(s) of interest. In preliminary studies, hAMSCs have been successfully modified to express BMP4 via viral transduction. These BMP4-releasing hAMSCs are able to target BTICs, reduce tumor burden, and increase survival in a human rodent brain tumor model (Li et al, 2014; Guerrero-Cazares et al, 2014) via BTIC differentiation (Piccirillo et al, 2006). Subsequently, hAMSCs have been non-virally engineered to express GFP and BMP4 with positive results (Mangraviti et al, submitted). It is now hypothesized that not only F.A.T. but also hAMSCs F.A.T. can be modified using these PBAE/DNA nanoparticles to express BMP4 and be used as delivery vehicles. Furthermore, to understand the behavior of hAMSCs in the context of more clinically relevant radiation therapy, a Small Animal Radiation Research Platform (SARRP) has been developed with the ability to deliver precise radiation to mammalian brains for our studies in stem cells (Ford et al., 2011, Redmond et al, 2011; Capilla-Gonzalez et al, 2014; Achanta et al, 2012) and in brain tumors (Zeng et al, 2013). Radiation causes cells to release cytokines which recruits macrophages and attracts MSCs (Zielske et al, 2009; van Valen et al, 1997; Monje et al., 2003). The findings obtained through this research will be crucial for stem cell-based therapies for brain cancers in human patients. The combination of clinical-relevant radiation of a human brain tumor model with cellular therapy using hAMSCs offers a high potential for a co-adjuvant therapy for brain cancer in human patients.

Example 2

Nanoparticle-Assisted Non-Viral Gene Delivery of Human Neural Stem Cells, BTICs, and hAMSCs is Effective Biodegradable, cationic, PBAE polymers as novel systems for non-viral gene (Tzeng. Guerrero-Cazares et al, 2011; Green et al, 2006; Green et al, 2009; Bhise et al, 2012; Shmueli et al, 2012; Sunshine et al, 2011) and siRNA (Lee et al, 2009; Taeng, Yang et alt 2011) delivery along with ways to coat these nanoparticles for cell type-specific targeted delivery (Green, Chiu et al, 2007; Harris et al, 2010) were developed. It was demonstrated that combinatorial modifications to polymers leads to the creation of polymeric nanoparticles that achieve virus-like efficacy in human primary cells (Green, Zugates et al, 2007) and enhanced efficacy in human stem cells (Green et al, 2008; Yang et al., 2009). These particles are promising in vivo as cancer therapeutics (Huang et al, 2009; Showalter et al., 2008), pro-angiogenic factors (Yang et al, 2010), and genetic vaccines (Nguyen et al, 2009). Previous efforts have resulted in highly effective biomaterials for non-viral gene delivery to hard-to-transfect human neural stem cells and BTICs (Guerrero-Cazares et al, 2014; Tzeng, Guerrero-Cazares et al, 2011; Shmueli et al, 2012). A library of polymers of gene delivery has been synthesized and characterized (Green, 2012; Tzeng, Guerrero-Cazares et al, 2011. Sunshine et al, 2011; Tzeng, Yang et al, 2011). From this library, excellent nanoparticles have been identified that transfect hAMSCs more efficiently than leading commercially available reagents and can deliver BMP4 (FIG. 1; Mangraviti et al, submitted). This advancement will be extended both in vitro and in vivo to newly established hAMSCs from the operating room (Table 1). Commercial hAMSCs have already been engineered to secrete BMP4 (Mangraviti et al, submitted) non-virally and the next step is to similarly modify primary cells from patients for personalized medicine. Polymeric nanoparticles will be further engineered for gene delivery to F.A.T. that has not seen culturing conditions and their transfection efficacy and effect on cell viability will be determined.

TABLE 1

| hAMSC lines from F.A.T. (n = 32, through 2013) | | |
|---|---|---|
| ID# | Age | Sex |
| AQH483 | 27 | M |
| AQH484 | 53 | M |
| AQH504 | 18 | M |
| AQH509 | 40 | F |
| AQH518 | 51 | F |
| AQH519 | 40 | F |
| AQH522 | 33 | F |
| AQH523 | 58 | M |
| AQH525 | 69 | F |
| AQH654 | 51 | M |
| AQH657 | 37 | F |
| AQH671 | 72 | F |
| AQH673 | 36 | M |
| AQH678 | 22 | F |
| AQH680 | 67 | F |
| AQH711 | 45 | M |
| AQH716 | 43 | M |
| AQH725 | 25 | M |
| AQH726 | 35 | M |
| AQH738 | 64 | F |
| AQH740 | 49 | M |
| AQH759 | 71 | M |
| AQH762 | 36 | F |
| AQH763 | 31 | F |
| AQH765 | 57 | F |
| AQH770 | 43 | F |
| AQH774 | 74 | M |
| AQH777 | 28 | M |
| AQH778 | 38 | F |
| AQH790 | 32 | F |

23

TABLE 1-continued

| hAMSC lines from F.A.T. (n = 32, through 2013) | | |
|---|---|---|
| ID# | Age | Sex |
| AQH794 | 11 | M |
| AQH799 | 49 | M |

Example 3

Nanoparticles Transfect Human Cells in Suspension

BTICs were transfected with DNA by suspension and incubation (Tzeng, Guerrero-Cazares et al, 2011) and hAM-SCs with siRNA using a similar method (Tzeng et al., 2012). This is important for clinical applicability, as F.A.T. can be taken from a patient, polymer-DNA nanoparticles added to the medium, and the suspension centrifuged to form a pellet where cells are in direct contact with nanoparticles (FIG. 2). In some embodiments, the presently disclosed subject matter provides methods to extract adipose tissue and directly mix it with nanoparticles to find the ideal formulation that will allow the maximization of the direct engineering of hAM-SCs derived from F.A.T. In other embodiments, these methods bypass culturing in the laboratory thereby allowing administration in the surgical cavity following brain surgery in a subject.

Example 4

Nanoparticles are Stored for Years and Sustain Gene Delivery

Long-term (>2 years) storage formulations were optimized for PBAE nanoparticles to further their clinical applicability (FIG. 3; Guerrero-Cazares et al. 2014). Sucrose was used as a lyoprotectant that needed only be reconstituted in water before use, reducing preparation time (Guerrero-Cazares et al, 2014; Tzeng, Guerrero-Cazares et al, 2011). However, although these lyophilized nanoparticles were created using only one of the several polymers available in the library and specifically to modify commercial hAMSCs, the presently disclosed methods provide methods for the lyophilization of other polymers and for other cell types. For example, the type of lyoprotectant (sugars) and the concentration of the lyoprotectant used can be varied. The transfection, viability and feasibility of mixing optimized lyophilized nanoparticles with primary hAMSCs contained within F.A.T from patients can be investigated.

Example 5 hAMSCs are Isolated and Characterized hAMSCs are isolated: hAMSCs have been isolated from intraoperative F.A.T. (Table 1; Pendleton et al, 2013; Smith et al, submitted; Feng et al, submitted). These cells express CD73, CD90, and CD105 (mesenchymal stem cell markers), but not CD31 (endothelial cell marker) or CD45 (hematopoietic cell marker) (Pendleton et al, 2013; Feng et al, submitted; Dominici et al, 2006) and are pluripotent (able to differentiate into adipocytes, chondrocytes, and osteocytes) (Li et al, 2014; Feng et al, submitted). No differences in growth or tropism to brain tumors between bone marrow-MSC and hAMSC lines were found (Pendleton et al., 2013), making adipose tissue attractive to study since they are easier to obtain and their sources are less limited.

hAMSCs migrate in vitro and in vivo in response to glioma: It was shown that hAMSCs migrate towards glioma (Li et al, 2014; Pendleton et al, 2013; Feng et al, submitted). Increased speed and persistence of hAMSC migration was found with glioma media on 3D-nanopattern surfaces (Li et al, 2011; Smith et al, submitted: Feng et al., submitted), hAMSCs were systemically delivered in a GBM mouse model and it was observed that GFP-labeled hAMSCs homed to human tumors including those derived from BTICs (FIGS. 4A and 4B; Li et al, 2014; Smith et al, submitted; Feng et al, submitted).

hAMSCs are non-tumorigenic: hAMSCs cultured with BTIC media do not transform into tumor associated fibroblasts (TAFs). Additionally, hAMSCs were delivered into mice with human tumors derived from the BTICs, and it was found that hAMSCs are nontumorigenic in vivo (Li et al, 2014; Feng et al, submitted) and indeed decrease tumor size (Li et al, 2014).

BMP4 does not Change the Multipotentiality or Tropism of hAASC:

The effect of BMP4 treatment on hAMSCs was assessed and it was found that it did not induce the differentiation of hAMSCs, which could negatively affect their tumor tropism (FIG. 5; Li et al., 2014). Additionally, the retroviral induction of BMP4 expression in hAMSC enhanced their tropism to GBM in vitro (Li et al, 2014). These findings suggest that hAMSCs remain pluripotent, keep their ability to migrate, and home to brain tumors in the presence of BMP4 even with viral engineering as seen in previous efforts.

Example 6

Human BTIC-Derived Murine Models

Human BTRC-derved murine models more accurately depict human cancer: BTIC-derived tumors, unlike commercially available GBM cell lines, accurately recapitulate the parent tumor both histologically and molecularly (Lee et al, 2006). BTIC lines are available that reliably produce intracranial GBMs that recapitulate the parent tumor and are able to migrate long distances in a murine xenotransplant model (Chaichana et al, 2009; Ying, Wang et al, 2011; Ying, Sang et al, 2011; Tilghman et al, 2014).

hAMSCs virally engineered to produce BMP4 prolong survival in a murine model with human brain cancer: hAMSCs were virally-modified to secrete BMP4 and it was found that they prolonged survival in a murine model of GBM (FIG. 6; Li et al, 2014). Additionally, hAMSCs virally-modified to secrete BMP4 targeted both GBM tumor bulk and BTICs (FIGS. 4A and 4B; Li et al, 2014). However, there are dangers to viral gene delivery, which includes insertional gene mutagenesis (Check, 2005) and life-threatening immune reactions (Hollon, 2000).

Example 7

Non-Viral Gene Delivery to Patient-Derived hAMSCs

To determine if non-viral gene delivery to patient-derived hAMSCs could be accomplished, poly(beta-amino ester) (PBAE) formulations were synthesized and tested for their feasibility for non-viral gene delivery to intraoperative patient-derived primary hAMSC cell cultures using previously described protocols (Tzeng, Yang et al. 2011; Tzeng et al, 2013). PBAEs were electrostatically complexed with enhanced green fluorescent protein (eGFP) DNA plasmid to assess transfection efficacy by flow cytometry and confirm low toxicity. In parallel, nanoparticles made of PBAE complexed with a GFP plasmid lacking CpG sequences were used to transfect hAMSCs to compare and contrast the efficacy of gene delivery between a conventional DNA plasmid and one containing minimal prokaryotic components.

As a first step, dose optimization studies were performed on intraoperative patient-derived primary hAMSCs (designated as 1082 hAMSCs) (FIG. 8). The transfection efficacy of a 7.8 μg/mL dose of PBAE/GFP 536-40 w/w nanoparticles was 61f0.6% with 98+7% viability (FIG. 9A, FIG. 9B and FIG. 9C). The same PBAE formulation proved efficacious on different intraoperative primary hAMSCs (cultures 1122, 1123). A comparison study between commercially available lipid-based transfection reagent Lipofectamine™ 2000 and PBAE-based nanoparticles on commercial hAM-SCs was performed, and higher transfection efficacy with the PBAE-based nanoparticles was observed, hAMSCs were transfected with GFP plasmid lacking CpG sequences, and the data suggested that CpG-free sequences resulted in brighter GFP signal in commercial hAMSCs (FIG. 10A. FIG. 10B and FIG. 10C), which may provide a strategy to further enhance trans gene expression.

These results showed that PBAE nanoparticles can be used for non-viral gene delivery to patient-derived hAM-SCs. Several PBAE/DNA formulations were used for dose optimization, and a biodegradable nanoparticle that is highly effective in transfecting hAMSC cell cultures with no statistically significant toxicity was obtained. Moreover, using plasmids that lack CpG sequences can further enhance the transfection efficacy in hAMSCs. The presently disclosed subject matter provides methods to modify primary hAM-SCs with nanoparticles to mitigate the dangers of viral gene delivery.

Example 8

Aim 1: To Effectively Deliver Exogenous Genes of Interest to F.A.T. from Patients Via Lyophilized Biodegradable Nanoparticles It is hypothesized that synthesized biodegradable polymers can be utilized to non-virally transfect MSCs contained in F.A.T. from patients. Here, the step of transfecting hAM-SCs in a dish over time can be bypassed and instead non-viral transfection can be optimized through direct mixing of lyophilized nanoparticles with F.A.T. It is further hypothesized that this approach will enable co-expression of multiple genes to enable secretion of multiple proteins from engineered F.A.T.

Preliminary data: Previous discoveries will be utilized to optimize the transfection of F.A.T. and hAMSCs from F.A.T. (Table 1), then assess its therapeutic anti-cancer use in vitro and in vivo, maximizing its translational nature. Some of these experiments are summarized as a representative overall study layout in FIG. 19.

The presently disclosed subject matter provides an opportunity to treat patients with brain cancer in the operating room immediately after surgery and before dural closure. Currently, the only FDA approved local intraoperative therapy is Gliadel (Attenello et al, 2008; McGirt et al, 2009) and no local cellular therapies exist. The presently disclosed subject matter provides new nanobiotechnology to enable non-viral gene-based therapeutics for brain cancer by using hAMSCs as targeting cellular therapies. Building on previous efforts (Example 11. Sunshine et al, 2011: Sunshine et al, 2009, Bhise et al, 2010), nanoparticles from leading polymer analogs will be fabricated that were discovered from screening a large polymer library on a variety of human cell types (Green et al, 2012; Tzeng, Guerrero-Cazares et al, 2011: Sunshine et al, 2011, Tzeng, Yang et al, 2011). Nanoparticle formulations have been obtained that showed higher transfection efficiency in cultured hAMSCs than the leading commercial reagent (FIG. 1). These nanoparticle formulations will be optimized for successful gene delivery to hAMSCs within primary human F.A.T. Ultimately, the goal is to transfect F.A.T, without prior cell culture or modification by directly transfecting F.A.T. within a suspension, purifying the suspension to extract the cell fraction, and readministering the engineered human cells directly to the patient during surgery, facilitating the use of this technology for personalized medicine. It is hypothesized that synthesized biodegradable polymers will be utilized to nonvirally transfect MSCs contained in F.A.T. from patients. Further, this approach will enable co-expression of multiple genes to enable secretion of multiple proteins from engineered F.A.T as indicated in FIG. 20.

In terms of preliminary data, biodegradable cationic polymers have been developed as novel systems for non-viral gene (Green et al, 2012; Tzeng, Guerrero-Cazares et al, 2011: Green et al., 2006; Green et al, 2009; Bhise et al, 2012; Shmueli et al, 2012; Sunshine et al, 2011) and siRNA delivery (Lee et al, 2009; Tzeng, Yang et al, 2011) Ways to coat these nanoparticles for targeted delivery also have been developed (Guerrero-Cazares et al, 2014; Tzeng, Guerrero-Cazares et al, 2011; Green, Chiu et al, 2007; Harris et al, 2010). It also has been demonstrated that combinatorial modifications to polymers can lead to the creation of polymeric nanoparticles that achieve virus-like efficacy in human primary cells (Green, Zugates et al, 2007) and enhanced efficacy inhuman stem cells (Green et al, 2008; Yang et al, 2009). It has been shown that these particles are promising in vivo as cancer therapeutics (Huang et al, 2009: Showalter et al, 2008), pro-angiogenic factors (Yang et al, 2010), and genetic vaccines (Guerrero-Cazares et al, 2014; Tzeng, Guerrero-Cazares et al, 2011: Nguyen et al, 2009). Candidate nanoparticle formulations from previous work commercial hAMSCs (Mangraviti et al, submitted) have been tested in commercial hAMSCs in culture and transfect commercial hAMSCs more efficiently than leading commercially available reagents (FIG. 1; Mangraviti et al, 2014). This will now be done in a direct suspension with F.A.T. Successful transfections have been performed by incubating cells with polymeric nanoparticles for 1-2 hours at 37° C., in suspension, aspirating the cells, and finally plating the cells (FIG. 2). Particles are available that retain full function with a shelf-life of at least 2 yrs at −20° C. by using sucrose as a lyoprotectant (FIG. 3; Guerrero-Cazares et al, 2014).

To Utilize a Library of Leading Biodegradable Polymers to Fabricate Nanoparticles for Optimized Gene Delivery to hAMSCs Contained within Patient F.A.T:

Leading polymers as members of the biomaterial array for use in this study have been selected after synthesizing and screening a large, structurally diverse library of 400 unique polymers, each with varying chemical properties including charge density and hydrophobicity. Polymers will be further synthesized using a two-step process and nanoparticles will be formed with plasmids of interest as previously described (Guerrero-Cazares et al, 2014; Tzeng, Guerrero-Cazares et al, 2011). The optimal formulation of the polymer will be assessed using high-throughput analysis of gene delivery nanoparticles encoding fluorescent protein (Tzeng and Green, 2013; Kim et al, 2013). The gene of interest contained within patient F.A.T. will be successfully delivered and efficiently expressed after optimization via high-throughput screening.

To synthesize different polymer structures: To synthesize different polymer structures, a two-step procedure will be used (FIG. 7). First, acrylate-terminated base polymers will be synthesized through the conjugate addition of 3-amino-1-propanol (S3), 4-amino-1-butanol (S4), and 5-amino-1-pentanol (S5) to 1,3-propanediol diacrylate (B3) and 1,4-butanediol diacrylate (B4), and 1,5-pentanediol diacrylate (B5). Second, small amine-containing molecules (E3, E5, E6, E7, E8) will be individually added as end-capping groups to each linear base polymer. Polymer structures and molecular weight will be carefully determined by $^1$H-NMR and gel permeation chromatography (GPC) as previously described (Sunshine et al, 2011). Preparative GPC will be used to control molecular weight. Synthesis will take place using a 1.1:1 acrylate to amine monomer molar ratio during the base polymer synthesis step and 10 kDa polymers will be selected through preparative GPC. The monomeric components we can choose from are shown in FIG. 7. Each of the backbone "B" numbers corresponds to the number of carbons between acrylate groups in the backbone monomer and each of the "S" numbers corresponds to the number of carbons between the amine group and alcohol group in the side-chain. For example, polymer "447" corresponds to backbone "B4", side-chain "S4", and end-group "E7." Each of these selected polymers shows convergence in structure and they are each analogs of each other, yet their differential efficacy is dramatically different.

To successfully form nanoparticles using plasmids of interest. Nanoparticles will be formed from plasmids and polymers by self-assembly and incubation in 25 mM aqueous sodium acetate (pH 5) for 10 min. All initial screening of potential PBAE nanoparticle candidates will be completed by delivering a GFP plasmid to primary hAMSCs donated from fifteen patients (Table 1). The optimal formulation for the nanoparticle will be determined and used to transfect primary hAMSCs contained with patient F.A.T from fifteen different patients. First, to obtain cells from F.A.T., blood vessels and fibrous tissue will be separated and the adipose tissue washed with a PBS and antibiotic solution. Collagenase will be added to dissolve the connective tissue and the digested tissue will be centrifuged. The pellet containing the stromal-vascular cellular fraction will be resuspended in MesenPro media (Invitrogen, Carlsbad, CA) and passed through a cell strainer to remove unwanted cell debris. The remaining solution will contain the cellular fraction to be used for the transfection experiments. Transfection efficiency of primary hAMSC and hAMSCs-containing F.A.T will be measured 2 days post-transfection via flow cytometry for hAMSC markers (CD105+, CD73+, CD90+, CD45-, CD31-) and GFP expression using an Accuri C6 flow cytometer equipped with an IntelliCyt 96-well plate reader and robotic loader (BD Biosciences, Franklin Lake, NJ). Additionally, the selectivity of transfection for mesenchymal stem cell (MSC) types will be assessed for each nanoparticle formulation for comparing the proportion of MSCs transfected versus other cell types present within the cell fraction such as endothelial or adipose cells. MSC viability will be assessed by using a 96-well plate CellTiter 96 MTS viability assay (Promega, Madison, WI).

Successful preliminary transfection of primary hAMSCs (three primary cell lines) using PBAE B4S5E6 (536) and an eGFP plasmid has been shown. FIG. 9A, FIG. 9B and FIG. 9C shows the results of a dose-study on primary hAMSCs (FIG. 9A-9B), the cellular viability, and transfection percentage of primary hAMSCs (FIG. 9C).

To synthesize and optimize nanoparticles to facilitate co-expression of two or more genes of interest: Up to approximately 100 plasmids can be encapsulated in each polymeric nanoparticle (Bhise et al, 2012). Multiple plasmids can be co-delivered into the same cells, such as GFP and DsRed plasmids to human IMR90 fibroblasts (FIG. 1A and FIG. 11B). Two or more fluorescent reporter plasmids can be used to determine co-expression levels in hAMSCs contained within patient F.A.T using techniques published previously (Guerrero-Cazares et al, 2014: Tzeng, Guerrero-Cazares et al, 2011). This will allow determination of the maximum number of different plasmids that can be delivered within the same nanoparticles while maintaining maximal expression of each individual gene. It is hypothesized that multiple genes of interest will be able to be co-delivered to the F.A.T.-derived hAMSCs to enable the secretion of multiple differentiation inducing and tumoricidal proteins simultaneously to the tumor site.

To determine optimal method for long-term storage of the particular engineered nanoparticle formulations: Optimal methods for long-term storage of the particular engineered nanoparticle formulations will be determined because stable lyophilized nanoparticles would facilitate efficient and simple clinical administration. It has been shown that nanoparticles lyophilized in a solution of sucrose are capable of long-term storage at −20° C., for over two years and were capable of transfecting primary human GBM cells (FIG. 3; Guerrero-Cazares et al, 2014). To investigate the long-term storage capability in the optimized nanoparticles for delivery to primary human F.A.T., transfection of F.A.T. between freshly-made versus lyophilized nanoparticles with varying concentrations of sugars as cryoprotectants will be compared by measuring expression of a GFP reporter plasmid. FIG. 2 shows a preliminary study of primary human F.A.T transfection with nanoparticles. It was hypothesized that particles can be lyophilized, then resuspended in a dissociated F.A.T. suspension to transfect the hAMSCs contained within the F.A.T. to create a simple and efficient method for future clinical applications and allow for long-term storage prior to administration. Drying the nanoparticles will lead to optimal control of their concentration following resuspension, which will allow for delivery of high doses within small volumes as was performed in petri dishes in cultured cells (Guerrero-Cazares et al, 2014: Tzeng, Guerrero-Cazares et al, 2011).

Summary: Nanoparticle formulations are available that have worked well with commercial hAMSCs (Mangraviti et al, submitted) and which will be used with hAMSCs contained within F.A.T. Nanoparticle formulations will be optimized specifically for hAMSCs contained within F.A.T to perform transfection in suspension. For this, the transfection on F.A.T will be optimized from a sample group of fifteen patients as the next step. This will allow for testing of the efficiency of the nanoparticle formulation for different F.A.T samples, making the technology more translatable and personalized. It is anticipated that a polymeric nanoparticle formulation will be optimized from the existing polymer library, the gene of interest will be efficiently expressed in MSCs contained within the F.A.T., two or more genes of interest will be co-expressed using an optimized nanoparticle formulation, and (4) effective lyophilized nanoparticles will be formed for long-term storage.

It has been found that that exogenous GFP delivery to hAMSCs lasts at least a week (FIG. 12) and that F.A.T. can be successfully transfected with PBAEs (FIG. 2). It is envisioned that F.A.T. will be able to be transfected without prior cell culture or modification.

Example 9

AIM 2: To Determine if Nanoparticle-Modified BMP4-Secreting hAMSCs Retain an Anti-Glioma Effect In Vitro It has been shown that engineering hAMSCs with nanoparticles will not adversely affect the properties that make hAMSCs an effective anti-cancer delivery vehicle, including the ability to migrate toward and track brain tumor initiating cells (BTICs). Nanoparticles have been used to engineer commercial hAMSCs in vitro and now they will be used with primary hAMSCs from patients. It is hypothesized that engineered hAMSCs will decrease GBM proliferation and invasion and drive differentiation of BTICs through secretion of BMP4.

Preliminary data: Even after multi-modal therapy, patients with GBM inevitably experience tumor recurrence. This has been attributed to the presence of BTICs and migratory GBM cells, both which contribute to therapy resistance and evasion. An effective treatment would target both types of cells. While previous studies demonstrate that virally modified hAMSCs track human GBMs in rodents and secrete BMP4 (Li et al, 2014; Pendleton et al, 2013), a primary concern is safety. Previous human studies have demonstrated a potential for oncogenic insertional mutagenesis (Check, 2005) and life-threatening immune responses (Hollon, 2000) with viral gene delivery. Therefore, primary hAMSCS from F.A.T. will be engineered with nanoparticles, as done with commercial hAMSCs, to secrete BMP4 (FIG. 13; Mangraviti et al, submitted). Nanoparticles are already available that have proven to be efficient in commercial (FIG. 1) and primary hAMSCs (FIGS. 2 and 9), and these will be further tested in vitro in cultured primary hAMSCs and newly established hAMSCs from F.A.T. (as summarized in FIG. 21). It is hypothesized that nanoparticle-modified primary BMP4-secreting cultured hAMSCs/hAMSCs harvested from F.A.T. will maintain stem cell characteristics, exhibit tumor-tropism, promote GBM differentiation, inhibit GBM proliferation, and suppress GBM migration via the secretion of BMP4.

Several intraoperatively-obtained human BTIC and hAMSC lines have been established (Tables 1 and 2). Commercial hAMSCs have been modified using viral gene delivery to secrete BMP4 (Li et al, 2014) and it has been found that they promote GBM differentiation, inhibit GBM proliferation, and suppress GBM migration. Furthermore, commercial hAMSCs have been modified using poly-p-amino-ester (PBAE) nanoparticle gene delivery to secrete BMP4 (Mangraviti et al, submitted) (FIG. 13). It has been found that these nanoparticle-modified BMP4-secreting commercial hAMSCs have superior motility (FIG. 14) and GBM tropism in vitro when compared to virally-modified hAMSCs. Primary hAMSCs will now be modified and tested. To assess hAMSC motility, a novel pseudo-3D nanopattern device (FIG. 14) developed by previous efforts was used to analyze speed, direction, and morphologies of migrating cells (Li et al, 2014; Garzon-Muvdi et al, 2012; Smith et al., submitted; Feng et al, submitted; Zhu et al, in press).

TABLE 2

| BTIC lines (GBM) by subclassification (through 2014) | |
| --- | --- |
| Subclassification | ID Nos. |
| Mesenchymal | AQH253, AQH549, AQH567, AQH626, AQH630, AQH911, AQH221, AQH318, AQH499, AQH940, AQH1045 |
| Proneural | AQH276, AQH501, AQH609, AQH612, AQH1049 |
| Classical | AQH965, AQH832, AQH834, AQH963 |

To determine if nanoparticle-modified BMP4-secreting hAMSCs maintain mesenchymal stem cell characteristics in vitro: It has been shown that both viral- and nanoparticle-modified BMP4-secreting hAMSCs maintain their mesenchymal stem cell characteristics in vitro (FIG. 5) and in vivo (FIGS. 4A and 4B; Li et al, 2014; Mangraviti et al, submitted). The ability of hAMSCs to maintain MSC characteristics after nanoparticle modification is important to their utility as vehicles for antitumor agents (Mangraviti et al., submitted). It is known that nanoparticle-modified commercial hAMSCs maintain their MSC characteristics (Mangraviti et al., submitted) but it will be determined whether this is true of hAMSCs from cultured F.A.T. Adipose tissue obtained from human F.A.T. will be dissociated and cultured to harvest hAMSCs and establish hAMSC cultures as published (Pendleton et al, 2013; Smith et al., submitted; Feng et al, submitted). These primary hAMSC cultures will then be nonvirally modified using PBAE nanoparticles to express BMP4. In vitro experiments will determine the stem like characteristics, motility, and proliferation capacity of these primary nanoparticle-modified BMP4-secreting hAMSCs. It is hypothesized that nanoparticle-modified hAMSCs maintain mesenchymal stem cell characteristics and GBM tropism in vitro.

To determine if nanoparticle-modified BMP4-secreting hAMSCs maintain stem cell characteristics in vitro: Naive hAMSCs and nanoparticle-modified BMP4-secreting hAMSCs from F.A.T. will be cultured in MesenPRO media (Invitrogen) and assessed by immunocytochemistry (ICC) for expression of stem cell phenotypic markers (CD105+, CD73+, CD90+, CD45−, CD34−, CD14−) (Li et al, 2014; Pendleton et al, 2013: Dominici et al, 2006). Additionally, these cells will be cultured in differentiation-inducing media and assessed for adipogenic, chondrogenic, and osteogenic differentiation via Oil Red O, Alizarin Red, or Collagen II staining, respectively (Li et al, 2014; Pendleton et al, 2013; Feng et al, submitted).

To determine the effect of nanoparticle-modification on hAMSC proliferative capacity m vitro: Viability of naive hAMSCs and primary nanoparticle-modified BMP4-secreting hAMSCs from F.A.T will be determined by Live/Dead™ Fixable Blue Dead Cell Stain Assay (Invitrogen) and MTS assay (Invitrogen). Cell proliferation will be estimated every 24 hours for 7 days using the alamarBlue assay (Invitrogen) and Click-IT EdU assay (Invitrogen) for the different time points (Li et al, 2014; Smith et al, submitted; Feng et al., submitted).

To determine the effect of nanoparticle-modification on hAMSC migratory capacity towards GBM in vitro: Naive hAMSCs and primary nanoparticle-modified hAMSCs from F.A.T. will be seeded in the top well of a Boyden chamber ($2 \times 10^4$ cells per chamber) with control or GBM conditioned media in the bottom well. After 24 hours, the migrated cells will be stained and counted from 9 random high-powered fields from each membrane. Migration will be expressed as the mean number of migrated cells per microscopic field (Li et al, 2014; Pendleton et al, 2013; Smith et al, submitted; Feng et al, submitted). To evaluate the effect of GBM conditioned media on hAMSC migration and speed, 3D nanopattern assays will be performed as previously described (FIG. 14; Li et al, 2014: Garzon-Muvdi et al, 2012; Smith et al, submitted; Feng et al, submitted; Zhu et al, in press).

To determine the effect of nanoparticle-modified BMP4-secreting hAMSCs on primary BTIC proliferation, migration, and differentiation: It has previously been shown that nanoparticle-modified BMP4-secreting commercial hAMSCs promote differentiation, suppress proliferation, and inhibit migration of BTICs (Mangraviti et al, submitted). It is hypothesized that nanoparticle-modified primary hAMSCs from F.A.T. will inhibit GBM proliferation, suppress GBM migration, promote GBM differentiation via BMP4 secretion.

To determine the effect of nanoparticle-modified primary hAMSCs on the proliferation of BTIC in vitro: BTICs will be cultured on laminin-coated 12 mm coverslips and grown in mitogen-containing media with or without rhBMP4 (100 ng/mL) or conditioned media derived from primary nanoparticle-modified BMP4-secreting hAMSCs. Cell proliferation will be assessed by the alamarBlue assay (Invitrogen) and Click-IT EdU assay (Invitrogen) for the different time points. Cell viability and apoptosis will be assessed by propidium iodide (PI) exclusion with DAPI counterstaining and TUNEL method (Click-iT Tunel Alexa-Fluor Imaging Assay, Invitrogen), respectively (Feng et al, submitted).

To determine the effect of nanoparticle-modifedprimary hAMSCs on the migration of BTIC in vitro: Culture media with or without rhBMP4 (100 ng/mL) or media from primary nanoparticle-modified BMP4-secreting hAMSCs will be used to treat cultured BTICs for different time points. The BTICs' migration will then be assessed using the Boyden migration assay with $2 \times 10^4$ BTICs per chamber. After 24 hours, the migrated cells will be stained and counted from 9 random high-power fields from each membrane. Also, the BTICs will be fixed, stained, and counted as described hereinabove. To evaluate the effect of media from nanoparticle-modified BMP4-secreting hAMSCs on BTIC migration and speed, 3D nanopattern assays will be performed as previously described ((Li et al, 2014; Garzon-Muvdi et al, 2012; Smith et al., submitted; Feng et al, submitted; Zhu et al, in press) using rhBMP4 (100 ng/ml) or media from nanoparticle-modified BMP4-secreting hAMSCs. Cell migration will be quantified with time-lapse microscopy as previously published (Li et al, 2104; Smith et al, submitted; Feng et al, submitted). Long-term observation will be performed with a motorized inverted microscope (Olympus 1X81). Phase-contrast images will be recorded for 15 hrs at 10-20 min intervals with Slidebook 4.1 (Intelligent Imaging, Denver, CO). Cell speed, persistence, and distance-travelled will be calculated based on tracking 50-100 cells per condition with MATLAB (Natick, Mass.).

To determine the effect of nanoparticle-modified primary hAMSCs on the differentiation state of BTICs in vitro: Media from primary nanoparticle-modified BMP4-secreting hAMSCs will be collected. BTICs will be treated with this conditioned media and evaluated by ICC and flow cytometry for differentiation into astrocytic (GFAP), neuronal (Tujl), and/or oligodendroglial (04) lineages as previously reported (Li et al, 2014; Pendleton et al, 2013; Feng et al, submitted).

To determine if nanoparticle-modified primary hAMSCs affect the known molecular subtypes of GBM-derived BTWs in vitro: From cell lines from previous efforts (Table 2), BTICs derived from three different GBM subtypes90 (Classical, Proneural, and Mesenchymal) will be cultured. Culture media with or without rhBMP4 (100 ng/ml) or media derived from primary nanoparticle-modified BMP4-secreting hAMSCs will be used to treat cultured BTICs. Proliferation, migration, and differentiation will be assessed as described hereinabove. This experiment will be performed for each BTIC sample representing the known GBM subtypes (AQH1045, AQH276, AQH965). The experiment will be repeated for each of the three different known GBM subtypes to determine if there is an interaction between the effect of hAMSCs and the type of BTIC treated (Verhaak et al, 2010).

Further experiments: Statistical comparisons will be performed using Kruskal-Wallis ANOVA, Student-Newman-Keuls analysis, and Chi-square Fisher's exact test, as appropriate based on an a=0.05. Based on 20 replicate measurements per hAMSC line, 5 hAMSC lines will need to be analyzed to detect a 20% difference in outcome measures (proportion of measures of differentiation, migration, and proliferation) with a power of 80% and a=0.05.

Experiments also may be performed to see if other physical transfection techniques can be combined with a chemical technique, such as nanoparticle plus mild electroporation. In other experiments, alternative anti-cancer genes of interest can be expressed, such as TRAIL, which has been successfully expressed in AMSCs using genetic modification (Li et al, 2014; Kucerova et al, 2010; Matuskova et al, 2010; Choi et al, 2011) or other genes (Table 3) including metabolic BTICs drivers, such as G6PC-a (Abbadi et al, under revision). Also, experiments can be conducted with multiple intraoperatively obtained BTIC lines (Table 2) (AQH1045, AQH276, and AQH965, representing mesenchymal, proneural, and classical GBM types, respectively). Additional lines are available in case the initial BTICs are unsuccessful. Also, co-culture of BTICs can be tested with nanoparticle-modified hAMSCs.

Summary: It is hypothesized that nanoparticle-modified BMP4-secreting primary hAMSCs will: (1) maintain stem-cell characteristics. (2) maintain their tumor-tropism, (3) inhibit BTIC proliferation and migration, (4) promote BTIC differentiation, and that (5) these effects on BTIC proliferation, migration, and differentiation will be replicable in all types of GBM-derived BTICs in vitro.

TABLE 3

| Mesenchymal stem cell therapies for gliomas | | |
| --- | --- | --- |
| Type of Vehicle | Vehicle | Reference |
| Chemotherapeutic | HSV-thymidine kinase | Mietic et al., 2007 |
| Viral delivery | Adenovirus | Nakamura et a., 2004 |
| Immunotherapeutic | IL-2 | Ryu at al., 2011 |
| | IL-12 | Xu et al., 2008 |
| | IL-18 | Yuan et al., 2006 |
| | IL-23 | Sato et al. 2005 |
| | Interferon-$\alpha$ | Nakamiza et al., 2005 |
| | Interferon-$\beta$ | Nakamura et a., 2004 |
| Apoptosis inducing | TRAIL | Choi et al., 2011; Kim et al., 2012 |
| Differentiation inducing | BMP4 | Li et al., 2014; Mangraviti et al., Submitted. (Non-viral Transfection) |

Example 10

AIM 3: To Determine the Safety and Efficacy of
Nanoparticle-Modified BMP4-Secreting hAMSC
Treatment in Combination with Targeted Radiation
Therapy on Human GBM in an In Vivo Murine
Model Previous efforts have shown that when commercial hAM-
SCs are engineered with nanoparticles in a rodent with a
human tumor, these hAMSCs arrive to their destination and
deliver BMP4. It is hypothesized that mice bearing human
GBM treated with nanoparticle-modified hAMSCs from
patients will survive longer due to hAMSC tumor tracking,
selective BMP4-secretion, and decreased tumor burden.

The goal is to establish whether nanoparticle-modified
hAMSCs can be used as safe and efficient delivery vehicles
of BMP4 to suppress GBM in vivo as summarized in FIGS.
22 and 23. It has been shown that hAMSCs virally modified
to deliver BMP4 suppress cancer progression in a mouse
model of human GBM2. It is hypothesized that mice bearing
human GBM treated with nanoparticle-modified hAMSCs
will survive longer due to hAMSC tumor tracking, BMP4-
secretion, and decreased GBM tumor progression.

For clinical applications, it is important to determine the
safety and efficacy of nanoparticle-modified BMP4-secret-
ing hAMSCs against GBM in vivo and also in the setting of
adjuvant radiotherapy (Shapiro et al, 1989), since it is
currently standard of care for GBM patients. Radiation leads
to an increase in the migration of BM-MSCs and umbilical
MSCs to tumors (colon and glioma), suggesting that radia-
tion can increase the effectiveness of MSCs for cancer
therapy (Zielske et al, 2009; Kim et al. 2010). Furthermore,
radiation causes cells to release cytokines which attracts
MSCs (Zielske et al, 2009). A novel radiation device for
rodents will be used that has been used in the study of neural
stem cells (Ford et al, 2011; Redmond et al, 2011; Capilla-
Gonzalez, 2014) and brain tumors (Zeng et al, 2013). It is
hypothesized that nanoparticle-modified BMP4-secreting
hAMSCs will home to GBM tumor bulk and migratory
GBM cells, inhibit tumor growth and migration, and, when
combined with precise radiation, further increase homing of
stem cells and survival of animals implanted with human
cancer.

Preliminary data: Several intraoperatively-obtained
human hAMSC (Table 1) and BTIC (Table 2) lines have
been established. Specifically, BTIC lines have been estab-
lished that exhibit malignant migration in a xenotransplan-
tation model in vivo (FIGS. 4 and 15); Li et al, 2011: Ying,
Wang et al, 2011: Ying, Sang et al, 2011; Sun et al, 2009:
Tilghman et al, 2014). Commercial hAMSCs have been
successfully modified via viral and nanoparticle-assisted
gene delivery to secrete BMP4 successfully in the brain
(FIGS. 4, 6, and 16; Li et al, 2014; Mangraviti et al.,
submitted). It has been found that virally modified BMP4-
secreting commercial hAMSCs reduce proliferation and
migration and drive differentiation of GBM in vivo (Li et al.,
2014). A single dose of virally modified BMP4-secreting
hAMSCs significantly decreased tumor size (FIG. 16A and
FIG. 16B) and improved the survival of GBM bearing mice
(FIG. 6; Li et al, 2014). Various delivery routes of nanopar-
ticle-modified hAMSCs in mice have been evaluated and it
has been determined that intravenous delivery allows these
nanoparticle-modified hAMSCs to localize to the brain
(FIG. 17A; Li et al., 2014; Mangraviti et al, submitted;
Smith et al, submitted). More specifically, nanoparticle-
modified commercial hAMSCs can be delivered selectively to brain tumors (FIG. 17B), showing the clinical translat-
ability of the presently disclosed subject matter. Previous
efforts have developed the small animal radiation research
platform (SARRP), which delivers focused radiotherapy to
small animals, similarly as is done in humans. The SARRP
has been used to study neurogenesis (Ford et al, 2011;
Redmond et al, 201 t; Capilla-Gonzalez et al., 2014; Achanta
et al, 2012) in the mammalian brain, to assess the effects of
radiotherapy on murine models of various cancers (FIGS.
18A, 18B, 18C, 18D and 18E; Tuli et al., 2014; Wada et al,
2013; Zeng et al., 2013; Tuli et al, 2012), and also it has been
found that SARRP augments the immune response and
improves survival in a murine brain tumor model (Zeng et
al., 2013).

To determine the effect f nanoparticle-modified BMP4-
secreting primary hAMSCs on tumor progression and sur-
vival in a murine human GBM model n vivo: It is hypoth-
esized that nanoparticle-modified BMP4-secreting hAMSCs
will decrease tumor progression and increase survival in
vivo. Athymic nude mice will be stereotactically injected
with $1\times10^6$ td-tomato-expressing BTICs or an equivalent
volume of phosphate-buffered saline (PBS) into the basal
ganglia (coordinates X: 1.5 mm, Y: 1.34 mm, Z: 3.5 mm) as
previously published (Li et al, 2014; Garzon-Muvdi et al,
2012; Smith et al, submitted; Feng et al., submitted). Tumor
establishment and progression will be confirmed via mag-
netic resonance imaging (MRI) in one mouse per group 28
days after tumor implantation (Kim et al, 2011). Then, the
mice will be anesthetized and inoculated with equal numbers
($6\times10^6$ cells) of luciferase-labeled nanoparticle-modified
hAMSCs (naive, empty vector, GFP, or primary BMP4-
secreting) or equal volume of PBS by intravenous injection
(n=7 per group) as previously reported (Mangraviti et al,
submitted; Smith et al, submitted). Two weeks later, the
mice will be sacrificed and stained for human nuclei and
td-tomato to locate tumor bulk, hAMSCs, and BTICs. The
proportion of BTICs immunoreactive to Ki-67 will be used
to assess proliferation. Proportion of Nestin, Tuj 1, and
GFAP positive cells will be used to quantify BTIC differ-
entiation (Li et al, 2014; Feng et al., submitted). GBM cell
migration will be quantified by measuring the distance of
GBM cells from the tumor bulk (Li et al, 2014; Feng et al,
submitted). The total number of hAMSCs and specifically
hAMSCs surrounding nests of GBM cells will be measured.
The ratio of averages in each group will establish the
propensity of hAMSCs to migrate towards GBM nests. Data
will be analyzed using Kruskal-Wallis analysis of variance
with the Student-Newman-Keuls post-hoc analysis.

To determine if multiple treatments of nanoparticle modi-
fied primary hAMSCs in combination with precise radio-
therapy maximizes antiglioma effect in vivo, including sur-
vival: Standard of care for GBM includes the administration
of adjuvant radiotherapy after tumor resection (McGirt et al,
2008; McGirt et al, 2009; Chaichana, Zadnik et al, 2013:
Chaichana et al, 2010; Chaichana et al, 2011). Thus, to more
accurately recapitulate the experience of human GBM, the
antiglioma effects ofhAMSC treatment will be assessed in
the context of radiotherapy. It has been shown that the
administration of a single 10 Gy of radiation via the SARRP
in a murine model of human tumor resulted in an increase in
survival (Zeng et al., 2013). It has also been shown that
hAMSCs were detectable up to 14 days after delivery in a
murine human GBM model in vivo, suggesting they func-
tion for only a short period of time (Li et al, 2014). A
solution for this limitation will be the use of pulsed treat-
ments, with repeated administration of nanoparticle-modi-
fied hAMSCs over time. It is hypothesized that mice bearing human GBM treated with pre-irradiation and weekly pulsed administration of nanoparticle-modified BMP4-secreting hAMSCs will survive longest due to decreased tumor progression.

In terms of experimental design, intracranial gliomas will be established as described hereinabove (FIGS. 22 and 23; Li et al, 2014; Garzon-Muvdi et al, 2012; Smith et al., submitted; Feng et al, submitted). Luciferase-expressing nanoparticle-modified hAMSCs (naive, empty vector. GFP, or primary BMP4-secreting) or equal volume of PBS will be delivered intravenously to athymic nude mice (FIG. 17A) in a weekly pulsed treatment either once or three times total in mice with and without pre-irradiation (10 Gy) using SARRP. Then, the mice will be followed bi-weekly using bioluminescence imaging (BLI) using luciferin administration to monitor hAMSC bio-distribution as previously published (FIG. 17B; Li et al, 2014; Mangraviti et al, submitted; Feng et al, submitted). In some cases, 7 mice will be used per group (7 total groups). Mice will be followed for up to 40 weeks to evaluate survival. At death or sacrifice, mice brains will be stained for td-tomato to determine the tumor progression. Kaplan-Meier survival analysis will be performed, with results reported as median and mean sumival times with a 95% confidence interval. Difference between groups will be determined by Log Rank analysis.

Further experiments: Statistical comparisons will be performed using Knskal-Wallis ANOVA, Student-Newman-Keuls analysis, and Chi-square Fisher's exact test, as appropriate with a=0.05. For in vivo experiments, group sizes (n=7 in each group) were calculated by power-analysis based on a need to detect a 20% treatment effect with 80% power and a=0.05. Experiments also may be performed to test if injection of nanoparticle-modified hAMSCs induces inflammation in the rodent brain and determine the optimal dosage of hAMSCs per injection.

It is hypothesized that nanoparticle-modified BMP4-secreting primary hAMSCs will secrete BMP4 in vivo, decrease proliferation and migration of GBM cells in vivo, induce BTIC differentiation in vivw, increase survival of GBM-bearing mice, and precise radiation will enhance these effects.

Example 11

SUMMARY

Currently, there is a dearth of effective treatments for brain cancer patients. This project will develop such a potential future therapeutic treatment by engineering hAMSCs from human F.A.T. to secrete anti-tumor compounds directly to brain tumor. The successful completion of this study will provide optimization of the method for directly transfecting intraoperatively obtained F.A.T. to secrete anti-tumor compounds using nanoparticles, determination of the anti-tumor characteristics of nanoparticle-modified hAMSCs, and elucidation of the therapeutic potential and application of nanoparticle-modified hAMSCs on intracranial GBM.

By the end of the study, the transfection of F.A.T. and its therapeutic anti-cancer use will be optimized in vivo, maximizing its translational nature, and allowing for human clinical trials. Innovations in this study include, but are not limited to: 1) using freshly extracted adipose tissue, rather than established commercial hAMSC cell lines 2) engineering F.A.T, as well as primary hAMSCs present within the F.A.T. using non-viral modification via PBAE/DNA nanoparticles 3) engineering primary hAMSCs to express two or more therapeutic genes of interest 4) developing optimal methods for long-term storage of nanoparticle formulations in a lyophilized form 5) using primary intraoperatively obtained human BTICs and F.A.T. extract (hAMSCs) to more accurately recapitulate GBM and hAMSC treatment 6) studying hAMSC migration after nanoparticle-modification using nanopattern and microfluidic devices (Chaichana et al, 2006) 7) studying the effect of nanoparticle-modified hAMSC on BTIC migration using nanopattern and microfluidics 8) using SARRP to study radiation effects on hAMSC (SARRP delivers precise radiation beams (<0.5 mm), analogous to conformal beam radiation in humans; Redmond et al, 2011. Achanta et al, 2012; Zeng et al, 2013: Zeng et al, 2011), and 9) using multiple treatments of the nanoparticle-modified hAMSCs from F.A.T. with the therapeutic gene of interest in combination with SARRP radiotherapy to fully recapitulate GBM and hAMSC treatment as it would occur in humans.

It is envisioned that the presently disclosed subject matter will allow the development of a medical field which will engineer hAMSCs to have secretion of therapeutic proteins and will use these nanoparticle-modified hAMSCs as an effective treatment for other types of primary and metastatic brain tumors, such as medulloblastoma, ependymoma, lung cancer, breast cancer, and melanoma, amongst others.

The successful completion of these aims will provide (1) optimization of an ideal nanoparticle formulation, in addition to existing nanoparticle candidates, to non-virally genetically engineer primary hAMSC from F.A.T. to secrete anti-tumor proteins, (2) characterization of the nanoparticle-modified hAMSCs and their tumor suppressive characteristics, and (3) the application of nanoparticle-modified hAMSCs on intracranial human GBM. For future clinical application, the nanoparticles could be administered to F.A.T. and the resulting engineered hAMSCs could be re-administered within a few hours.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein Although the foregoing subject matter has been described in some detail by way of illustration and example for purposes of clarity of understanding, it will be understood by those skilled in the art that certain changes and modifications can be practiced within the scope of the appended claims.

Abbadi, S.; Rodarte, J. J.; Abutaleb, A.; Lavell, E.; Smith, C. L.; Ruff, W.; Schiller. J.; Olivi, A.; Levchenko, A.; Guerrero-Cazares, H.; Quinones-Hinojosa, A. Identification of Glucose-6-phosphatase alpha as a key metabolic regulator for glioblastoma cell invasion. *Mol. Cancer Res*. Under Revision.

Aboody, K. S.; Najbauer, J.; Metz, M. Z.; D'Apuzzo, M.; Gutova, M.; Annala, A. J.; Synold, T. W.; Couture, L. A.; Blanchard, S.; Moats, R. A.; Garcia, E.; Aramburo, S.; Valenzuela, V. V.; Frank, R T.; Barish, M. E.; Brown, C. E.; Kim, S. U.; Badie, B.; Portnow, J. Neural stem cell-mediated enzyme/prodrug therapy for glioma: precinical studies. *Sci. Transl. Med* 2013; 5(184):184ra59.

Achanta. P.; Capilla-Gonzalez, V.; Purger, D.; Reyes, J.; Sailor. K.; Song, H.; Garcia-Verdugo, J. M.; Gonzalez-Perez, O.; Ford, E.; Quinones-Hinojosa. A. Subventricular Zone Localized Irradiation Affects the Generation of Proliferating Neural Precursor Cells and the Migration of Neuroblasts. *Stem Cells*. 2012; 30(11): 2548-60.

Ahmed, A. U.; Thaci, B.; Alexiades, N. G.; Han, Y.; Qian, S.; Liu, F.; Balyasnikova, I. V.; Ulasov, I. Y.; Aboody, K S.; Lesniak, M. S. Neural stem cell-based cell carriers enhance therapeutic efficacy of an oncolytic adenovirus in an orthotopic mouse model of human glioblastoma. *Mol Ther*. 2011; 19(9): 17 14-26.

Attenello. F.; Mukherjee, D.; Datoo. G.; McGirt, M.; Bohan, E.; Weingart, J.; Olivi, A.; Quinones-Hinojosa, A.; Brem, H. Use of Gliadel (BCNU) Wafer in the Surgical Treatment of Malignant Glioma; A 10-Year Institutional Experience. *Ann. Surg. Oncol*. 2008:15 (10):2887-93.

Bao, S.; Wu, Q.; McLendon, R. E.; Hao, Y.; Shi, Q.; Hjelmeland, A. B.; Dewhirst, M. W.; Bigner, D. D.; Rich, J. N. Glioma stem cells promote radioresistance by preferential activation of the DNA damage response. *Nature*. 2006:444(7120):756-60.

Bhise, N. S.; Gray, R. S.; Sunshine, J. C.; Htet, S.; Ewald, A. J.; Green, J. J. The relationship between terminal functionalization and molecular weight of a gene delivery polymer and transfection efficacy in mammary epithelial 2-D cultures and 3-D organotypic cultures. *Biomaterials,* 2010; 31(31):8088-96.

Bhise, N. S.; Shmueli, R. B.; Gonzalez. J.; Green, J. J. A novel assay for quantifying the number of plasmids encapsulated by polymer nanoparticles. *Small,* 2012; 8(3):367-73.

Bhise. N. S.; Wahlin, K. J.; Zack, D. J.; Green, J. J. Evaluating the potential of poly (beta-amino ester) nanoparticles for reprogramming human fibroblasts to become induced pluripotent stem cells. *Int. J. Nanomedicine*. 2013; 8:4641-58.

Bleau, A. M.; Hambardzumyan, D.; Ozawa, T.; Fomchenko, E. I.; Huse, J. T.; Brennan. C. W.; Holland. E. C. PTEN/P 3K/Akt pathway regulates the side population phenotype and ABCG2 activity in glioma tumor stemlike cells. *Cell Stem Cell*. 2009:4(3):226-35.

Capilla-Gonzalez, V.; Guerrero-Cazares, H.; Bonsu, J. M.; Gonzalez-Perez, O.; Achanta, P.; Wong, J.; Garcia-Verdugo, J. M.; Quinones-Hinojosa, A. The Subventricular Zone Is Able to Respond to a Demyelinating Lesion After Localized Radiation. *Stem Cells*. 2014; 32(1):59-69.

CBTRUS: Central Brain Tumor Registry of the United States. CBTRUS Statistical Report Tables.

Chaichana, K. L.; Garzon-Muvdi, T.; Parker, S.; Weingart, J. D.; Olivi. A.; Bennett, R.; Brem, H.; Quinones-Hinojosa, A. Supratentorial glioblastoma multiforme: the role of surgical resection versus biopsy among older patients. *Ann. Surg. Oncol*. 2011:18(1):239-45.

Chaichana, K. L.; Guerrero-Cazares, H.; Capilla-Gonzalez, V.; Zamora-Berridi, G.; Achanta, P.; Gonzalez-Perez, O.; Jallo, G. I.; Garcia-Verdugo, J. M.; Quinones-Hinojosa, A. Intra-operatively obtained human tissue: protocols and techniques for the study of neural stem cells. *J. Neurosci. Methods*. 2009; 180(1):116-25.

Chaichana, K. L.; Jusue-Torres, I.; Navarro-Ramirez, R.; Raza, S. M.; Pascual-Gallego, M.; Ibrahim, A.; Hernandez-Hermann, M.; Gomez, L.; Ye, X.; Weingart, J. D.; Olivi, A.; Blakeley, J.; Gallia, G. L.; Lim, M.; Brem, H.; Quinones-Hinojosa, A. Establishing percent resection and residual volume thresholds affecting survival and recurrence for patients with newly diagnosed intracranial glioblastoma. *Neuro. Oncol*. 2014; 16(1): 113-22.

Chaichana, K. L.; McGirt, M. J.; Laterra, J.; Olivi, A.; Quinones-Hinojosa, A. Recurrence and malignant degeneration after resection of adult hemispheric low-grade gliomas. *J. Neurosurg*. 2010; 112(1): 10-7.

Chaichana, K. L.; Quinones-Hinojosa, A. Neuro-oncology: Paediatric brain tumours-when to operate? *Nat. Rev. Neurol*. 2013; 9(7):362-4.

Chaichana, K. L.; Zadnik, P.; Weingart, J. D.; Olivi. A.; Gallia, G. L.; Blakeley, J.; Lim. M.; Brem, H.; Quinones-Hinojosa, A. Multiple resections for patients with glioblastoma: prolonging survival. *J. Neurosurg*. 2013; 118(4):812-20.

Chaichana, K.; Zamora-Berridi, G.; Camara-*Quintana*. J.; Quinones-Hinojosa, A. Neurosphere assays: growth factors and hormone differences in tumor and nontumor studies. *Stem Cells*. 2006; 24(12):2851-7.

Check, E. Gene therapy put on hold as third child develops cancer. *Nature*. 2005; 433(7026):561.

Chen, L.; Guerrero-Cazares, H.; Ye, X.; Ford, E.; McNutt, T.; Kleinberg, L.; Lim, M.; Chaichana, K.; Quinones-Hinojosa, A.; Redmond, K. Increased Subventricular Zone Radiation Dose Correlates With Survival in Glioblastoma Patients After Gross Total Resection. *Int. J. Radiat. Oncol. Biol. Phys*. 2013; 86(4):616-22.

Chesler, D. A.; Berger, M. S.; Quinones-Hinojosa, A. The potential origin of glioblastoma initiating cells. *Front Biosci*. (Schol Ed), 2012; 4:190-205.

Choi, S. A.; Hwang, S. K.; Wang, K. C.; Cho, B. K.; Phi, J. H.; Lee, J. Y.; Jung, H. W.; Lee, D. H.; Kim, S. K. Therapeutic efficacy and safety of TRAIL-producing human adipose tissue-derived mesenchymal stem cells against experimental brainstem glioma. *Neuro. Oncol*. 2011; 13(1):61-9.

Dominici, M.; Le Blanc, K.; Mueller. I.; Slaper-Cortenbach. I.; Marini, F. Krause, D.; Deans, R.; Keating, A.; Prockop, D.; Horwitz. E. Minimal criteria for defining multipotent mesenchymal stromal cells. The International Society for Cellular Therapy position statement. *Cytotherapy*. 2006; 8(4):315-7.

Eramo. A.; Ricci-Vitiani, L.; Zeuner, A.; Pallini, R.; *Lotti*, F.; Sette, G.; Pilozzi, E.; Larocca, L. M.; Peschle, C; De Maria, R. Chemotherapy resistance of glioblastoma stem cells. *Cell Death Differ*. 2006:13(7): 1238-41.

Feng, Y.; Zhu, M.; Dangelmajer, S.; Wijesekera, O.; Castellanos, C. X.; Lee, Y. M.; Denduluri, A.; Chaichana, K. L.; Li. Q.; Zhang, H.; Levchenko, A.; Guerrero-Cazares, H.; Quinones-Hinojosa, A. Hypoxia-cultured human adipose derived mesenchymal stem cells are nononcogenic and have enhanced viability, motility, and tropism to brain cancer. Submitted.

Ford, E. C.; Achanta, P.; Purger. D.; Armour, M.; Reyes, J.; Fong, J.; Kleinberg, L.; Redmond, K.; Wong, J.;

US 12,642,817 B2

39

Jang, M. H.; Jun, F L; Song, H. J.; Quinones-Hinojosa, A. Localized C T-Guided Irradiation Inhibits Neurogenesis in Specific Regions of the Adult Mouse Brain. *Radiat. Res.* 2011;175(6):774-83.

Frank, R. T.; Najbauer, J.; Aboody, K. S. Concise review: stem cells as an emerging platform for antibody therapy of cancer. *Stem Cells.* 2010; 28(11):2084-7.

Galli, R.; Binda, E.; Orfanelli, U.; Cipelletti, B.; Gritti, A.; De *Vitis*, S.; Fiocco, R.; Foroni, C; Dimeco, F.; Vescovi, A. Isolation and Characterization of Tumorigenic, Stem-like Neural Precursors from Human Glioblastoma. *Cancer Res.* 2004; 64(19):7011-21.

Garzon-Muvdi, T.; Quinones-Hinojosa, A. Neural Stem Cell Niches and Homing: Recruitment and Integration into Functional Tissues. *ILAR J.* 2010; 51(1):3-23.

Garzon-Muvdi, T.; Schiapparelli, P.; ap Rhys, C; Guerrero-Cazares, H.; Smith, C; Kim, D. H.; Kone, L.; Farber, H.; Lee, D. Y.; An, S. S.; Levchenko, A.; Quinones-Hinojosa, A. Regulation of brain tumor dispersal by NKCCl through a novel role in focal adhesion regulation. *PLoS Biol.* 2012; 10(5): e1001320.

Green, J. J, 2011 Rita Schaffer Lecture: Nanoparticles for Intracellular Nucleic Acid Delivery. *Ann. Biomed. Eng.* 2012 July; 40(7): 1408-18.

Green, J. J.; Chiu. E., Leshchiner, E. S., Shi. J., Langer, R., Anderson, D. G. Electrostatic ligand coatings of nanoparticles enable ligand-specific gene delivery to human primary cells. *Nano Lett.* 2007; 7(4):874-9.

Green, J. J.; Shi, J.; Chiu, E.; Leshchiner, E. S.; Langer, R.; Anderson, D. G. Biodegradable polymeric vectors for gene delivery to human endothelial cells. *Bioconjug. Chem.* 2006; 17:1162-9.

Green, J. J.; Zhou, B. Y.; Mitalipova, M. M.; Beard, C; Langer, R.; Jaenisch, R.; Anderson, D. G. Nanoparticles for gene transfer to human embryonic stem cell colonies. *Nano Lett.* 2008:8(10):3126-30.

Green, J. J.; Zugates, G. T.; Langer, R.; Anderson, D. G. Poly(beta-amino esters): procedures for synthesis and gene delivery. *Methods Mol. Biol.* 2009; 480:53-63.

Green, J. J.; Zugates, G. T.; Tedford, N. C.; Huang, Y.; Griffith, L. G.; Lauffenburger, D. A.; Sawicki. J. A.; Langer. R.; Anderson. D. G. Combinatorial modification of degradable polymers enables transfection of human cells comparable to adenovirus. *Advanced Materials.* 2007; 19(19):2836-42.

Guerrero-Cazares, H.; Chaichana, K. L.; Quinones-Hinojosa, A. Neurosphere culture and human organotypic model to evaluate brain tumor stem cells. *Methods Mol. Biol.* 2009:568:73-83.

Guerrero-Cazares, H.; Chen, L.; Quinones-Hinojosa, A. Glioblastoma heterogeneity and more accurate representation in research models. *World Neurosurg.* 2012; 78(6):594-6.

Guerrero-Cazares, H.; Tzeng, S. Y.; Young, N. P.; Abutaleb, A. O.; Quinones-Hinojosa. A.; Green, J. J., Biodegradable polymeric nanoparticles show high efficacy and specificity at DNA delivery to human glioblastoma in vitro and in vivo. *ACS Nano.* 2014; 8(5):5 141-53.

Harris, T. J.; Green, J. J.; Fung, P. W.; Langer. R.; Anderson. D. G.; Bhatia, S. N. Tissue-specific gene delivery via nanoparticle coating. *Biomaterials.* 2010; 31(5):998-1006.

Hollon, T. Researchers and regulators reflect on first gene therapy death. *Nat. Med.* 2000 January; 6(1):6.

Huang, Y. H.; Zugates, G. T.; Peng, W.; Holtz, D.; Dunton, C; Green. J. J.; Hossain, N.; Chernick, M. R.; Padera,

R. F. Jr.; Langer, R.; Anderson, D. G.; Sawicki, J. A. *Cancer Res.* 2009; 69(15):6184-91.

Kim, T.; Momin, E.; Choi, J.; Yuan, K.; Zaidi, H.; Kim, J.; Park, M.; Lee, N.; McMahon, M. T.; Quinones-Hinojosa, A.; Bulte, J. W.; Hyeon, T.; Gilad, A. A. Mesoporous silica-coated hollow manganese oxide nanoparticles as positive T I contrast agents for labeling and MRJ tracking of adipose-derived mesenchymal stem cells. *J. Am. Chem. Soc.* 2011; 133(9):2955-61.

Kim, S. M.; Oh, J. H.; Park, S. A.; Ryu, C. H.; Lim, J. Y.; Kim, D-S.; Chang, J. W.; Oh, W.; Jeun, S-S. Irradiation Enhances the Tumor Tropism and Therapeutic Potential of Tumor Necrosis Factor-Related Apoptosis-Inducing Ligand-Secreting Human Umbilical Cord Blood-Derived Mesenchymal Stem Cells in Glioma Therapy. *Stem Cells.* 2010; 28(12):22 17-28.

Kim, J.; Sunshine, J. C.; Green, J. J. Differential Polymer Structure Tunes Mechanism of Cellular Uptake and Transfection Routes of Poly(p-amino ester) Polyplexes in Human Breast Cancer Cells. *Bioconjug. Chem.* 2013; 25(1):43-51.

Kostowski, T. A.; Zaidi. H. A.; Quinones-Hinojosa. A. Applications of Neural and Mesenchymal Stem Cells in the Treatment of Gliomas. *Expert Rev. Anticancer Ther.,* 2009; 9(5):597-612.

Kozielski, K. L.; Tzeng, S. Y.; Green, J. J. Bioengineered nanoparticles for siRNA delivery. WileyInterdiscip. Rev. *Nanomed. Nanobiotechnol.* 2013:5(5):449-68.

Kozielski, K. L.; Tzeng, S. Y.; Hurtado De Mendoza, B. A.; Green, J. J. Bioreducible cationic polymer-based nanoparticles for efficient and environmentally triggered siRNA delivery to primary human brain cancer cells. *ACS Nano.* 2014; 22; 8(4):3232-41.

Kucerova, L.; Matuskova, M.; Hlubinova. K.; Altanerova, V.; Altaner. C. Tumor cell behaviour modulation by mesenchymal stromal cells. *Mol. Cancer.* 2010; 9:129.

Lee. J. S.; Green, J. J.; Love, K. T.; Sunshine, J.; Langer, R.; Anderson. D. G. Gold, poly(beta-amino ester) nanoparticles for small interfering RNA delivery. *Nano Lett.* 2009; 9(6):2402-6.

Lee, J.; Kotliarova, S.; Kotliarov. Y.; Li. A.; Su. Q.; Donin. N. M.; Pastorino, S.; Purow, B. W.; Christopher, N.; Zhang, W.; Park, J. K.; Fine, H A. Tumor stem cells derived from glioblastomas cultured in bFGF and EGF more closely mirror the phenotype and genotype of primary tumors than do serum-cultured cell lines. *Cancer Cell.* 2006; 9(5):391-403.

Li, Y.; Li, A.; Glas, M.; Lai, B.; Ying, M.; Sang, Y.; Xia, S.; Trageser. D.; Guerrero-Cazares, H.; Eberhart, C. G.; Quinones-Hinojosa, A.; Schefflier, B.; Laterra, J, c-Met signaling induces a reprogramming network and supports the glioblastoma stem-like phenotype. *Proc. Natl. Acad. Sci. USA.* 2011; 108(24):9951-6.

Li, Q.; Wijeseekera, O.; Salas, S. J.; Wang, J. Y.; Zhu, M.; Aprhys, C; Chaichana, K. L.; Chesler, D. A.; Zhang, H.; Smith, C. L.; Guerrero-Cazares, H.; Levchenko, A.; Quinones-Hinojosa, A., Mesenchymal stem cells from human fat engineered to secrete BMP4 Are nononcogenic, suppress brain cancer, and prolong survival. *Clin. Cancer Res.* 2014; 20(9):2375-87.

Mangraviti, A.; Tzeng, S. Y.; Seng, M.; Abbadi, S.; Kozielski, K.; Schiapparelli, P.; Wijesekera. O.; Sarabia-Estrada. R.; Brem. H.; Tyler. B.; Olivi, A.; Green, J. J.; Quinones-Hinojosa, A. Adipose Stem Cells Engineered With Nanoparticles to secrete BMP4: A Non-Viral Therapy For Glioblastoma. Submitted The 19th

41

Annual Scientific Meeting and Education Day of the Society for Neuro-Oncology; Nov. 13-16, 2014; Miami. Fla.

Mangraviti, A.; Tzeng, S.; Seng, M.; Abbadi, S.; Kozielski, K.; Schiapparelli, P.; Wijesekera, O.; Sarabia-Estrada, R.; Brem, H.; Tyler, B.; Olivi. A.; Green, J. J.; Quinones-Hinojosa, A. BMP4-Secreting hAdMSCs Engineered with Nanoparticles: A Non-Viral MSC-Based Therapy for Brain Cancer. Submitted.

Matuskova. M.; Hlubinova, K.; Pastorakova, A.; Hunakova, L.; Altanerova, V.; Altaner, C; Kucerova, L. HSV-tk expressing mesenchymal stem cells exert bystander effect on human glioblastoma cells. *Cancer Lett.* 2010:290(1):58-67.

McGirt, M. J.; Chaichana, K. L.; Attenello, F. J.; Weingart. J. D.; Than. K.; Burger, P. C.; Olivi, A.; Brem, H.; Quinones-Hinojosa, A. Extent of surgical resection is independently associated with survival in patients with hemispheric infiltrating low-grade gliomas. *Neurosurgery,* 2008; 63(4):700-7.

McGirt, M. J.; Chaichana, K. L.; Gathinji, M.; Attenello, F. J.; Than. K.; Olivi, A.; Weingart, J. D.; Brem. H.; Quinones-Hinojosa, A. Independent association of extent of resection with survival in patients with malignant brain astrocytoma. *J. Neurosurg.* 2009; 110(1): 156-62.

McGirt, M. J.; Mukherjee, D.; Chaichana, K. L.; Than, K. D.; Weingart, J. D.; Quinones-Hinojosa, A. Association of surgically acquired motor and language deficits on overall surcical after resetion of glioblastoma multiforme. *Neurosurgery,* 2009; 65(3):463-70.

McGirt, M. J.; Than. K. D.; Weingart, J. D.; Chaichana, K. L.; Attenello, F. J.; Olivi, A.; Laterra. J.; Kleinberg, L. R.; Grossman, S. A.; Brem, H.; Quinones-Hinojosa, A. Gliadel (BCNU) wafer plus concomitant temozolomide therapy after primary resection of glioblastoma multiforme. *J. Neurosurg.* 2009; 110(3):583-8.

Momin, E. N.; Mohyeldin, A.; Zaidi, H. A.; Vela, G.; Quinones-Hinojosa, A. Mesenchymal stem cells: new approaches for the treatment of neurological diseases. *Curr. Stem. Cell Res. Ther.* 2010; 5(4):326-44.

Murat A, Migliavacca E, Gorlia T, Lambiv W L, Shay T. Hamou M F, de Tribolet N, Regli L. Wick W. Kouwenhoven M C, Hainfellner J A, Heppner F L, Dietrich P Y, Zimmer Y, Cairncross J G, Janzer R C, Domany E, Delorenzi M, Stupp R, Hegi M E. Stem cell-related "self-renewal" signature and high epidermal growth factor receptor expression associated with resistance to concomitant chemoradiotherapy in glioblastoma. *J. Clin Oncol.* 2008; 26(18):3015-24.

Nguyen D N, Green J J, Chan J M, Langer R. Anderson D G. Polymeric Materials for Gene Delivery and DNA Vaccination. *Adv. Mater.* 2009; 21(8):847-67.

Pendleton, C; Li, Q.; Chesler, D. A.; Yuan, K.; Guerrero-Cazares, F L; Quinones-Hinojosa, A., Mesenchymal stem cells derived from adipose tissue vs. bone marrow: in vitro comparison of their tropism towards gliomas. *PLoS One.* 2013; 8(3): e58198.

Piccirillo S G, Reynolds B A, Zanetti N, Lamorte G, Binda E. Broggi G, Brem H. Olivi A, Dimeco F, Vescovi A L. Bone morphogenetic proteins inhibit the tumorigenic potential of human brain tumour-initiating cells. *Nature.* 2006; 444(7120):761-5.

Quinones-Hinojosa A, Chaichana K. The human subventricular zone: a source of new cells and a potential source of brain tumors. *Exp Neurol.* 2007; 205(2):3 13-24.

Redmond K J. Achanta P. Grossman S A. Armour M. Reyes J. Kleinberg L, Tryggestad E. Quinones-Hinojosa A. Ford E C. A radiotherapy technique to limit dose to neural progenitor cell niches without compromising tumor coverage. *J. Neurooncol.* 2011; 104(2):579-87.

Rich J N. Cancer stem cells in radiation resistance. *Cancer Res.* 2007; 67(19):8980-4.

Sakariassen P O, Immervoll H, Chekenya M. Cancer stem cells as mediators of treatment resistance in brain tumors: status and controversies. *Neoplasia,* 2007; 9(11):882-92.

Sanai N. Tramontin A D. Quinones-Hinojosa A, Barbaro N M, Gupta N. Kunwar S, Lawton M T, McDermott M W, Parsa A T, Manuel-Garcia Verdugo J. Berger M S, Alvarez-Buylla A. Unique astrocyte ribbon in adult human brain contains neural stem cells but lacks chain migration. *Nature.* 2004:427(6976):740-4.

Shapiro W R, Green S B, Burger P C, Mahaley M S, Selker R G, VanGilder J C, Robertson J T, Ransohoff J, Mealey J, Strike T A, Pistenmaa D A, Randomized trial of three chemotherapy regimens and two radiotherapy regimens in postoperative treatment of malignant glioma. *J. Neurosurg.* 1989:71(1): 1-9.

Shmueli R B, Ohnaka M, Miki A, Pandey N B, Lima e Silva R, Koskimaki J E, Kim J, Popel A S, Campochiaro P A, Green J J. Long-term suppression of ocular neovascularization by intraocular injection of biodegradable polymeric particles containing a serpin-derived peptide. *Biomaterials,* 2013; 34(30):7544-51.

Shmucli R B, Sunshine J C, Xu Z. Duh E J, Green J J. Gene delivery nanoparticles specific for human microvasculature and macrovasculature. *Nanomedicine,* 2012 October; 8(7): 1200-7.

Showalter S L. Huang Y H, Witkiewicz A, Costantino C L, Yeo C J, Green J J, Langer R, Anderson D G, Sawicki J A, Brody J R. Nanoparticulate delivery of diphtheria toxin DNA effectively kills Mesothelin expressing pancreatic cancer cells. *Cancer Biol. Ther.* 2008; 7(10): 1584-90.

Siegel R. Naishadham D, Jemal A. Cancer statistics, 2013. *C A; A Cancer Journalfor Clinicians.* 2013; 63(1):11-30.

Singh S K, Hawkins C. Clarke I D, Squire J A, Bayani J, Hide T, Henkelman R M, Cusimano M D. Dirks P B. Identification ofhuman brain tumour initiating cells. *Nature.* 2004; 432(7015):396-401.

Smith, C. L.; Chaichana, K. L.; Lin. B.; O'Donnell. T.; Gupta, S.; Shah, S.; Wang, J.; Wijesekera. O.; Delannoy, M.; Levchenko, A.; Quinones-Hinojosa, A. Prime Time for Mesenchymal Stem Cell Therapy: Enhancing their Homing to Brain Tumors. Submitted.

Stupp R, Mason W P, van den Bent M J, Weller M. Fisher B, Taphoorn M J, Belanger K. Brandes A A, Marosi C. Bogdahn U. Curschmann J, Janzer R C, Ludwin S K. Gorlia T. Allgeier A, Lacombe D. Cairncross J G, Eisenhauer E. Mirimanoff R O. Radiotherapy plus concomitant and adjuvant temozolomide for glioblastoma. *N. Engl. J. Med.* 2004; 352(10):987-96.

Sun P, Xia S, Lai B. Eberhart C G, Quinones-Hinojosa A, Maciaczyk J, Matsui W. Dimeco F, Piccirillo S M, Vescovi A L, Laterra J. DNER, an epigenetically modulated gene, regulates glioblastoma-derived neurosphere cell differentiation and tumor propagation. *Stem Cells.* 2009:27(7): 1473-86.

Sunshine J C, Akanda M I, Li D, Kozielski K L, Green J J, Effects of base polymer hydrophobicity and end-group modification on polymeric gene delivery. *Biomacromolecules.* 2011; 12(10):3592-600.

Sunshine J, Bhise N, Green J J. Degradable polymers for gene delivery. *Conf. Proc. IEEE Eng. Med Biol. Soc.* 2009; 1:2412-5.

Thomas C E, Ehrhardt A, Kay M A. Progress and problems with the use ofviral vectors for gene therapy. *Nat. Rev. Genet.* 2003 May; 4(5):346-58.

Tilghman J, Wu H. Sang Y, Shi X, Guerrero-Cazares H. Quinones-Hinojosa A, Eberhart C G, Laterra J. Ying M. HMMR Maintains the Sternness and Tumorigenicity of Glioblastoma Stem-like Cells. *Cancer Res.* 2014:74 (11):3168-79.

Tuli R, Surmak A J, Reyes J. Armour M, Hacker-Prietz A, Wong J. DeWeese T L, Herman J M. Radiosensitization of Pancreatic Cancer Cells In Vitro and In Vivo through Poly (ADP-ribose) Polymerase Inhibition with ABT-888. *Transl. Oncol.* 2014; Epub ahead of print.

Tuli R, Surmak A, Reyes J. Hacker-Prietz A, Armour M, Leubner A, Blackford A. Tryggestad E, Jaffee E M, Wong J. DeWeese T L, Herman J M. Development of a Novel Preclinical Pancreatic Cancer Research Model; Bioluminescence Image-Guided Focal Irradiation and Tumor Monitoring of Orthotopic Xenografts. *Transl. Oncol.* 2012; 5(2):77-84.

Tzeng, S. Y.; Guerrero-Cazares, H.; Martinez, E. E.; Sunshine. J. C.; Quinones-Hinojosa, A.; Green, J. J., Non-viral gene delivery nanoparticles based on poly (p-amino esters) for the treatment of glioblastoma. *Biomaterials* 2011; 32(23):5402-10.

Tzeng, S. Y.; Green, J. J. Subtle changes to polymer structure and degradation mechanism enable highly effective nanoparticles for siRNA and DNA delivery to human brain cancer. *Adv. Healthc. Mater.* 2013; 2(3): 468-80.

Tzeng S Y, Higgins L J, Pomper M G, Green J J. Student award winner in the Ph.D, category for the 2013 society for biomaterials annual meeting and exposition, april 10-13, 2013, Boston, Mass.: biomaterial-mediated cancer-specific DNA delivery to liver cell cultures using synthetic poly(beta-amino ester)s. *J. Biomed Mater. Res. A.* 2013 July; 101(7): 1837-45, doi: 10.1002/jbm.a.34616. Epub 2013 Apr. 5

Tzeng, S. Y.; Hung, B. P.; Grayson, W. L.; Green. J. J. Cystamine-terminated poly(beta-amino ester)s for siRNA delivery to human mesenchymal stem cells and enhancement of osteogenic differentiation. *Biomaterials.* 2012; 33(32):8142-51.

Tzeng S Y, Yang P H. Grayson W L, Green J J. Synthetic poly(ester amine) and poly(amido amine) nanoparticles for efficient DNA and siRNA delivery to human endothelial cells. *Int. J. Nanomedicine.* 2011; 6:3309-22.

van Valen F, Kentrup-Lardong V, Truckenbrod B, Rube C, Winkelmann W, Jurgens W W. Regulation of the release of tumour necrosis factor (TNF)alpha and soluble TNF receptor by gamma irradiation and interferon gamma in Ewing's sarcoma/peripheral primitive neuroectodermal tumour cells. *J. Cancer. Res. Clin. Oncol.* 1997:123(5):245-52.

Verhaak R G, Hoadley K A, Purdom E. Wang V, Qi Y. Wilkerson M D, Miller C R, Ding L. Golub T, Mesirov J P, Alexe G. Lawrence M, O'Kelly M. Tamayo P, Weir B A, Gabriel S, Winckler W, Gupta S, Jakkula L, Feiler H S, Hodgson J G, James C D, Sarkaria J N, Brennan C, Kahn A, Spellman P T, Wilson R K, Speed T P, Gray J W, Meyerson M. Getz G, Perou C M, Hayes D N.

Integrated genomic analysis identifies clinically relevant subtypes of glioblastoma characterized by abnormalities in PDGFRA, IDHI, EGFR, and NFI. *Cancer Cell.* 2010; 17(1):98-110.

Vilalta M, Degano I R. Bago J, Gould D, Santos M. Garcia-Arranz M, Ayats R, Fuster C, Chernajovsky Y, Garcia-Olmo D, Rubio N, Blanco J. Biodistribution, long-term survival, and safety ofhuman adipose tissue derived mesenchymal stem cells transplanted in nude mice by high sensitivity non-invasive bioluminescence imaging. *Stem Cells Dev.* 2008; 17(5):993-1003.

Wada, S.; Harris, T. J.; Tryggestad, E.; Yoshimura, K.; Zeng, J.; Yen. H-R.; Getnet. D.; Grosso, J. F.; Bruno, T. C.; De Marzo. A. M.; Netto, G. J.; Pardoll, D. M.; DeWeese, T. L.; Wong, J.; Drake, C. G. Combined Treatment Effects ofRadiation and Immunotherapy: Studies in an Autochthonous Prostate Cancer Model. *Int. J. Radial. Oncol. Biol. Phvs.* 2013; 87(4):769-76.

Wei, J.; Barr, J.; Kong. L. Y.; Wang, Y.; Wu. A.; Sharma, A. K.; Gumin, J.; Henry, V.; Colman, H.; Sawaya, R.; Lang, F. F.; Heimberger, A. B. Glioma-associated cancer-initiating cells induce immunosuppression. *Clin. Cancer Res.* 2010; 16(2):461-73.

Xie, T. X.; Aldape. K. D.; Gong. W.; Kanzawa, T.; Suki, D.; Kondo, S.; Lang. F.; Ali-Osman, F.; Sawaya, R.; Huang, S. Aberrant N F-kappaB activity is critical in focal necrosis formation ofhuman glioblastoma by regulation of the expression of tissue factor. *Int. J. Oncol.* 208:33(1):5-15.

Yang, F.; Cho, S. W.; Son, S. M.; Bogatyrev, S. R.; Singh, D.; Green, J. J.; Mei, Y.; Park, S.; Bhang, S. H.; Kim, B. S.; Langer, R.; Anderson, D. G. Genetic engineering of human stem cells for enhanced angiogenesis using biodegradable polymeric nanoparticles. *Proc. Natl. Acad Sci USA.* 2010; 107(8):33 17-22.

Yang, F.; Green, J. J.; Dinio, T.; Keung, L.; Cho, S. W.; Park, H.; Langer, R., Anderson. D. G. Gene delivery to human adult and embryonic cell-derived stem cells using biodegradable nanoparticulate polymeric vectors. *Gene Ther.* 2009; 16(4):533-46.

Ying, M.; Sang, Y.; Li. Y.; Guerrero-Cazares, H.; Quinones-Hinojosa, A.; Vescovi, A. L.; Eberhart, C. G.; Xia, S.; Laterra, J. Kruppel-like family of transcription factor 9, a differentiation-associated transcription factor, suppresses Notch 1 signaling and inhibits glioblastoma-initiating stem cells. *Stem Cells.* 2011; 29(1):20-31.

Ying, M.; Wang, S.; Sang, Y.; Sun, P.; Lai, B.; Goodwin, C. R.; Guerrero-Cazares, F L; Quinones-Hinojosa, A.; Laterra, J.; Xia, S. Regulation of glioblastoma stem cells by retinoic acid: role for Notch pathway inhibition. *Oncogene.* 2011; 30(31):3454-67.

Zaidi, H. A.; Kosztowski, T.; DiMeco, F.; Quinones-Hinojosa, A. Origins and clinical implications of the brain tumor stem cell hypothesis. *J. Neurooncol.* 2009; 93(1):49-60.

Zeng, J.; Aziz, K.; Chettiar, S. T.; Aftab, B. T.; Armour. M.; Gajula, R.; Gandhi, N.; Salih, T.; Herman, J. M.; Wong, J.; Rudin, C M.; Tran, P. T.; Hales, R. K. Hedgehog Pathway Inhibition Radiosensitiaes Non-Small Cell Lung Cancers. *Int. J. Radiat. Oncol. Biol. Phys.* 2013; 86(1): 143-9.

Zeng, J.; See, A. P.; Aziz, K.; Thiyagarajan, S.; Salih, T.; Gajula, R. P.; Armour, M.; Phallen, J.; Terezakis, S.; Kleinberg, L.; Redmond, K.; Hales, R. K.; Salvatori, R.; Quinones-Hinojosa, A.; Tran, P. T.; Lim, M. Nelfinavir induces radiation sensitization in pituitary adenoma cells. *Cancer Biol. Ther.* 2011:12(7):657-63.

Zeng, J.; See, A. P.; Phallen, J.; Jackson. C M.; Belcaid, Z.; Ruzevick, J.; Durham, N.; Meyer, C; Harris, T. J.; Albesiano, E.; Pradilla, G.; Ford, E.; Wong, J.; Hammers, H-J.; Mathios, D.; Tyler. B.; Brem. H.; Tran, P. T.; Pardoll, D.; Drake, C. G.; Lim, M. Anti-PD-1 Blockade and Stereotactic Radiation Produce Long-Term Survival in Mice With Intracranial Gliomas. *Int. J. Radial. Oncol. Biol. Phys.* 2013; 86(2):343-9.

Zhu, M.; Feng, Y.; Dangelmajer. S.; Guerrero-Cazares, H.; Chaichana. K. L.; Smith, C. L.; Levchenko, A.; Lei. T.; Quinones-Hinojosa, A. Human cerebrospinal fluid regulates proliferation and migration of stem cells through insulin-like growth factor 1. *Stem Cells Dev.* In Press.

Zielske, S. P.; Livant, D. L.; Lawrence, T. S. Radiation increases invasion of gene-modified mesenchymal stem cells into tumors. *Int. J. Radiat. Oncol. Biol. Phys.* 2009; 75(3):843-53.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a brain tumor in a patient in need thereof, the method comprising:

administering to the patient, nanoparticle-modified, adipose-derived mesenchymal stem cells (AMSCs) comprising AMSCs containing a nanoparticle formulation comprising biodegradable polymers self-assembled with nucleic acid molecules, wherein the biodegradable polymer is selected from the group consisting of 2-(3-aminopropylamino)ethanol end-modified poly(1, 4-butanediol diacrylate-co-4-amino-1-butanol), (1-(3-aminopropyl)-4-methylpiperazine end-modified poly(1,4-butanediol diacrylate-co-4-amino-1-butanol), 2-(3-aminopropylamino)ethanol end-modified poly(1,4-butanediol diacrylateco-5-amino-1-pentanol), (1-(3-aminopropyl)-4-methylpiperazine end-modified poly(1,4-butanediol diacrylate-co-5-amino-1-pentanol), 2-(3-aminopropylamino)ethanol end-modified poly(1,5 pentanediol diacrylate-co-3-amino-1-propanol), and (1-(3-aminopropyl)-4-methylpiperazine-end-modified poly(1,5 pentanediol diacrylate-co-3-amino-1-propanol), wherein the nanoparticle formulation has a polymer to nucleic acid weight ratio of 25 to 75 weight polymer: weight nucleic acid, wherein the nucleic acid molecules encode one or more anti-cancer agents selected from the group consisting of bone morphogenic protein 4 (BMP4), TNF related apoptosis-inducing ligand (TRAIL), HSV-thymidine kinase, an oncolytic adenovirus, interleukin-2 (IL-2), interleukin-12 (IL-12), interleukin-18 (IL-18), interleukin-23 (IL-23), Interferon-α, and Interferon-β.

2. The method of claim 1, wherein the nanoparticle-modified, adipose-derived mesenchymal stem cells are administered to the patient systemically.

3. The method of claim 1, wherein the nanoparticle-modified, adipose-derived mesenchymal stem cells are administered to the patient intracranially.

4. The method of claim 1, comprising lyophilizing the nanoparticle formulation prior to combining with the adipose-derived mesenchymal stem cells.

5. The method of claim 1, comprising administering to the patient one or both of: a radiotherapy and a chemotherapeutic agent concurrently with the administration of the nanoparticle-modified, adipose-derived mesenchymal stem cells.

6. A method for treating a brain tumor in a patient in need thereof, the method comprising:

(a) transfecting adipose-derived mesenchymal stem cells (AMSCs), wherein transfecting comprises combining the AMSCs with a nanoparticle formulation to form a suspension, wherein the nanoparticle formulation comprises biodegradable poly-β-amino-ester polymers self-assembled with nucleic acid molecules, wherein the nucleic acid molecules encode one or more anti-cancer agents selected from the group consisting of bone morphogenic protein 4 (BMP4), TNF related apoptosis-inducing ligand (TRAIL), HSV-thymidine kinase, an oncolytic adenovirus, interleukin-2 (IL-2), interleukin-12 (IL-12), interleukin-18 (IL-18), interleukin-23 (IL-23), Interferon-α, and Interferon-β;

(b) extracting a cellular fraction from the suspension, wherein the cellular fraction comprises AMSCs transfected with the nucleic acid molecules; and (c) administering the AMSCs transfected with the nucleic acid molecules to the patient.

7. The method of claim 6, wherein the nanoparticle formulation comprises biodegradable polymers self-assembled with nucleic acid molecules, wherein the biodegradable polymer is selected from the group consisting of 2-(3-aminopropylamino)ethanol end-modified poly(1, 4-butanediol diacrylate-co-4-amino-1-butanol), (1-(3-aminopropyl)-4-methylpiperazine end-modified poly(1,4-butanediol diacrylate-co-4-amino-1-butanol), 2-(3-aminopropylamino)ethanol end-modified poly(1,4-butanediol diacrylateco-5-amino-1-pentanol), (1-(3-aminopropyl)-4-methylpiperazine end-modified poly(1,4-butanediol diacrylate-co-5-amino-1-pentanol), 2-(3-aminopropylamino)ethanol end-modified poly(1,5 pentanediol diacrylate-co-3-amino-1-propanol), and (1-(3-aminopropyl)-4-methylpiperazine-end-modified poly(1,5 pentanediol diacrylate-co-3-amino-1-propanol), and wherein the nanoparticle formulation has a polymer to nucleic acid weight ratio of 25 to 75 weight polymer: weight nucleic acid.

8. The method of claim 7, wherein the adipose-derived mesenchymal stem cells transfected with the nucleic acid molecules are administered to the patient systemically.

9. The method of claim 7, wherein the adipose-derived mesenchymal stem cells transfected with the nucleic acid molecules are administered to the patient intracranially.

10. The method of claim 7, comprising lyophilizing the nanoparticle formulation to combining with the adipose-derived mesenchymal stem cells to form a suspension.

11. An adipose-derived mesenchymal stem cell (AMSC) comprising at least one nanoparticle, wherein the nanoparticle comprises a biodegradable polymer self-assembled with a nucleic acid molecule encoding one or more anti-cancer agents selected from the group consisting of bone morphogenic protein 4 (BMP4), TNF related apoptosis-inducing ligand (TRAIL), HSV-thymidine kinase, an oncolytic adenovirus, interleukin-2 (IL-2), interleukin-12 (IL-12), interleukin-18 (IL-18), interleukin-23 (IL-23), Interferon-α, and Interferon-β, and wherein the biodegradable polymer is selected from the group consisting of 2-(3-aminopropylamino)ethanol end-modified poly(1, 4-butanediol diacrylate-co-4- amino-1-butanol), (1-(3-aminopropyl)-4-methylpipera-zine end-modified poly(1,4-butanediol diacrylate-co-4-amino-1-butanol), 2-(3-aminopropylamino)ethanol end-modified poly(1,4-butanediol diacrylateco-5-amino-1-pentanol), (1-(3-aminopropyl)-4-methylpiperazine end-modified poly(1,4-butanediol diacrylate-co-5-amino-1-pentanol), 2-(3-aminopropylamino) ethanol end-modified poly(1,5 pentanediol diacrylate-co-3-amino-1-propanol), and (1-(3-aminopropyl)-4-methylpiperazine-end-modified poly(1,5 pentanediol diacrylate-co-3-amino-1-propanol).

12. The adipose-derived mesenchymal stem cell of claim 11, wherein the biodegradable polymer has a polymer to nucleic acid weight ratio of 25 to 75 weight polymer:weight nucleic acid.

13. The adipose-derived mesenchymal stem cell of claim 12, wherein the one or more bioactive molecules are func-tional in the treatment of a brain tumor.

14. The adipose-derived mesenchymal stem cell of claim 11, wherein the adipose-derived mesenchymal stem cell is a human adipose-derived mesenchymal stem cell.

\* \* \* \* \*